US009365649B2

(12) United States Patent
Lundgren-Åkerlund

(10) Patent No.: US 9,365,649 B2
(45) Date of Patent: Jun. 14, 2016

(54) MONOCLONAL ANTIBODY CAPABLE OF BINDING INTEGRIN ALPHA 10 BETA 1

(71) Applicant: Xintela AB, Bjarred (SE)

(72) Inventor: Evy Lundgren-Åkerlund, Bjarred (SE)

(73) Assignee: Xintela AB, Lund (SE)

( * ) Notice: Subject to any disclaimer, the term of this patent is extended or adjusted under 35 U.S.C. 154(b) by 110 days.

(21) Appl. No.: 14/032,900

(22) Filed: Sep. 20, 2013

(65) Prior Publication Data

US 2014/0099716 A1    Apr. 10, 2014

Related U.S. Application Data

(60) Division of application No. 13/193,293, filed on Jul. 28, 2011, now Pat. No. 8,563,255, which is a continuation of application No. 12/285,587, filed on Oct. 9, 2008, now Pat. No. 8,012,696, which is a continuation of application No. 10/553,226, filed as application No. PCT/SE2004/000580 on Apr. 14, 2004, now Pat. No. 7,452,677.

(60) Provisional application No. 60/320,112, filed on Apr. 16, 2003.

(30) Foreign Application Priority Data

Apr. 14, 2003  (SE) ...................... 0301087

(51) Int. Cl.
| | | |
|---|---|---|
| *G01N 33/53* | (2006.01) | |
| *C07K 16/28* | (2006.01) | |
| *G01N 33/569* | (2006.01) | |

(52) U.S. Cl.
CPC ......... *C07K 16/2842* (2013.01); *C07K 16/2839* (2013.01); *G01N 33/56966* (2013.01); *G01N 2333/7055* (2013.01); *Y10S 435/81* (2013.01); *Y10S 435/975* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 5,225,539 | A | 7/1993 | Winter |
| 5,514,548 | A | 5/1996 | Krebber et al. |
| 5,565,332 | A | 10/1996 | Hoogenboom et al. |
| 5,585,089 | A | 12/1996 | Queen et al. |
| 5,686,059 | A | 11/1997 | Goetinck et al. |
| 5,698,761 | A | 12/1997 | Pohl et al. |
| 5,698,762 | A | 12/1997 | Dauerman |
| 5,843,436 | A | 12/1998 | Loike et al. |
| 5,853,987 | A | 12/1998 | Guo et al. |
| 5,928,945 | A | 7/1999 | Seliktar |
| 5,945,292 | A | 8/1999 | Brizzard |
| 6,096,873 | A | 8/2000 | Schaefer et al. |
| 7,029,858 | B1 | 4/2006 | Lundgren-Akerlund |
| 2003/0039966 | A1 | 2/2003 | Hering et al. |
| 2003/0055231 | A1 | 3/2003 | Ni et al. |
| 2003/0129685 | A1 | 7/2003 | Ni et al. |
| 2005/0260702 | A1 | 11/2005 | Pan |
| 2006/0099622 | A1 | 5/2006 | Ni et al. |
| 2006/0122373 | A1 | 6/2006 | McCarthy et al. |
| 2006/0123495 | A1 | 6/2006 | Gullberg et al. |
| 2006/0178503 | A1 | 8/2006 | Lundgren-Akerlund |
| 2006/0275287 | A1 | 12/2006 | St Croix et al. |
| 2007/0037206 | A1 | 2/2007 | Rosen |

FOREIGN PATENT DOCUMENTS

| | | |
|---|---|---|
| CA | 2 324 381 A1 | 10/1999 |
| CA | 2 440 974 A1 | 9/2002 |
| EP | 0120694 | 10/1984 |
| EP | 0125023 | 11/1984 |
| EP | 0239400 | 9/1987 |
| EP | 0330506 | 8/1989 |
| JP | 2001-354699 | 12/2001 |
| WO | WO 86/01533 | 3/1986 |
| WO | WO 92/19647 | 11/1992 |
| WO | WO 94/25487 | 11/1994 |
| WO | WO 97/31653 | 9/1997 |
| WO | WO 99/51639 | 10/1999 |
| WO | WO 00/51639 A2 | 9/2000 |
| WO | WO 02/072030 | 11/2002 |
| WO | WO 03/101497 | 12/2003 |
| WO | WO 03/105492 | 12/2003 |

OTHER PUBLICATIONS

Bengtsson et al. Loss of α10β1 integrin expression leads to moderate dysfunction of growth plate chondrocytes. Journal of Cell Science 118 (5):929-936.*

(Continued)

*Primary Examiner* — Maher Haddad
(74) *Attorney, Agent, or Firm* — Finnegan, Henderson, Farabow, Garrett & Dunner LLP.

(57) ABSTRACT

The present invention provides a monoclonal antibody or a fragment thereof binding to the extracellular I-domain of integrin alpha10beta1 and a hybridoma cell line deposited at the Deutsche Sammlung von Microorganismen and Zellkulturen GmbH under the accession number DSM ACC2583. Furthermore, the present invention also provides a monoclonal antibody or a fragment thereof binding to the extracellular I-domain of integrin alpha10beta1 produced by the hybridoma cell line deposited. Methods and uses of said antibody or a fragment thereof in identifying and selecting cells of a chondrogenic nature for treatment purposes, in particular for the identification and isolation of chondrocytes, mesenchymal progenitor cells and embryonic stem cells for tissue engineering of cartilage, or for identifying diagnostic and therapeutic tools in studying the biological role and the structural/functional relationships of the integrin alpha10beta1 with its various extracellular matrix ligands are also included.

6 Claims, 14 Drawing Sheets

(56) References Cited

OTHER PUBLICATIONS

Richard F. Loeser. Integrins and chondrocyte—matrix interactions in articular cartilage. Matrix Biology 39 (2014) 11-16.*
Popova et al. α11β1 Integrin-Dependent Regulation of Periodontal Ligament Function in the Erupting Mouse Incisor. Mol Cell Biol. Jun. 2007; 27(12): 4306-4316.*
Armulik, "Studies on the transmembrane signaling of betel integrins," Acta Universitatis Upsaliensis. Comprehensive summaries of Uppsala dissertations from the faculty of medicine 963, pp. 1-92, 2000.
Barry et al., "Biotinylated gene therapy vectors," Expert Opin Biol Ther., vol. 3, pp. 925-940, Sep. 2003.
Bird et al., "Single-chain antigen-binding proteins," Science, vol. 242, pp. 423-426, Oct. 21, 1988.
Boudreau et al., "Extracellular matrix and integrin signalling: the shape of things to come," Biochem J., vol. 339, pp. 481-485, May 1, 1999.
Boulianne et al., "Production of functional chimaeric mouse/human antibody," Nature, vol. 312, pp. 643-646, Dec. 13, 1984.
Brittberg et al., "Treatment of deep cartilage defects in the knee with autologous chondrocyte transplantation," N Engl J Med., vol. 331, pp. 889-895, Oct. 6, 1994.
Brittberg, "Autologous chondrocyte transplantation," Clin Orthop Relat Res., vol. 367 Suppl, pp. S147-S155, Oct. 1999.
Bruder et al., "Growth kinetics, self-renewal, and the osteogenic potential of purified human mesenchymal stem cells during extensive subcultivation and following cryopreservation," J Cell Biochem., vol. 64, pp. 278-294, Feb. 1995.
Camper et al., "Distribution of the collagen-binding integrin alpha10beta1 during mouse development," Cell Tissue Res., vol. 306, pp. 107-116, Oct. 2001.
Camper et al., "Integrin alpha2beta1 is a receptor for the cartilage matrix protein chondroadherin," J. Cell Biol., vol. 138. pp. 1159-1167, Sep. 8, 1997.
Camper et al., "Isolation, cloning, and sequence analysis of the integrin subunit alpha10, a beta1-associated collagen binding integrin expressed on chondrocytes," J. Biol. Chem., vol. 273, pp. 20383-20389, Aug. 7, 1998.
Caplan et al., "Mesenchymal stem cells: building blocks for molecular medicine in the 21st century," Trends Mol Med., vol. 7, pp. 259-264, Jun. 2001.
Conrad et al., "GATA transcription in a small rhodamine 123(low)CD34(+) subpopulation of a peripheral blood-derived CD34(-)CD105(+) mesenchymal cell line," Exp Hernatol., vol. 30, pp. 887-895, Aug. 2002.
Daugherty et al., "Polymerase chain reaction facilitates the cloning, CDR-grafting, and rapid expression of a murine monoclonal antibody directed against the CD18 component of leukocyte integrins," Nucleic Acids Res., vol. 19. pp. 2471-2476, May 11, 1991.
David et al., "Protein iodination with solid state lactoperoxidase," Biochemistry, vol. 13, pp. 1014-1021, Feb. 26, 1974.
Diamond et al., "The I domain is a major recognition site on the leukocyte integrin Mac-1 (CD11b/CD18) for four distinct adhesion ligands," J Cell Biol., vol. 120, pp. 1031-1043, Feb. 1993.
Emsley et al., "Structural basis of collagen recognition by integrin alpha2beta1," Cell, vol. 101, pp. 47-56, Mar. 31, 2000.
Fong et al., "Comparison of human blastulation rates and total cell number in sequential culture media with and without co-culture," Hum Reprod., vol. 14, pp. 774-781, Mar. 1998.
Fong et al., "Ongoing normal pregnancy after transfer of zone-free blastocysts: implications for embryo transfer in the human," Hum Reprod., vol. 12, pp. 557-560, Mar. 1997.
Funaro et al., "Monoclonal antibodies in clinical applications," J Biol Regul Homeost Agents, vol. 10, pp. 72-82, Oct. 1996.
Gough et al., "Rapid and quantitative preparation of cytoplasmic RNA from small numbers of cells," Anal Biochem., vol. 173, pp. 93-95, Aug. 15, 1988.
Gullberg et al., "Collagen-binding I domain integrins—what do they do?," Prog Histochem Cytochem., vol. 37, pp. 3-54, 2002.
Haukanes et al., "Application of magnetic beads in bioassays," Biotechnology , vol. 11, pp. 60-63, Jan. 1993.
Heino, "The collagen receptor integrins have distinct ligand recognition and signaling functions," Matrix Biol., vol. 19, pp. 319-323, Aug. 2000.
Hering, "Regulation of chondrocyte gene expression," Front Biosci., vol. 4, pp. 743-761, Oct. 15, 1999.
Hillier et al., Genebank Accession No. N72734, 1996.
Holmvall et al., "Chondrocyte and chondrosarcoma cell integrins with affinity for collagen type II and their response to mechanical stress," Exp. Cell Res., vol. 221, pp. 496-503, 1995.
Jarrin et al., "Sequencing of antibodies," Methods Mol Biol., vol. 96, pp. 21-28, 1999.
Jobanputra et al., "Effectiveness of autologous chondrocyte transplantation for hyaline cartilage defects in knees: a rapid and systematic review," Health Technol Assess., vol. 5, pp. 1-57, 2001.
Johnstone et al., "Mesenchymal cell transfer for articular cartilage repair," Expert Opin Biol Ther., vol. 1, pp. 915-921, Nov. 2001.
Jones et al., "Replacing the complementarity-determining regions in a human antibody with those from a mouse," Nature, vol. 321, pp. 522-525, May 29, 1986.
Jorgensen et al., "Stem cells for repair of cartilage and bone: the next challenge in osteoarthritis and rheumatoid arthritis," Ann Rheum Dis., vol. 60, pp. 305-309, Apr. 2001.
Kammann et al., "Rapid insertional mutagenesis of DNA by polymerase chain reaction (PCR)," Nucleic Acids Res., vol. 17, pp. 5404, Jul. 11, 1989.
Kirschstein et al., "Stem cells: scientific progress and future research directions," National Institutes of Health Report, Jun. 2001.
Lehnert et al., "The integrin alpha10 subunit: expression pattern, petal gene structure, and chromosomal localization," Cytogenet. Cell Genet., vol. 87, pp. 238-244, 1999.
Lewis et al., "Immunoglobulin complementarity-deterrnining region grafting by recombinant polymerase chain reaction to generate humanised monoclonal antibodies," Gene, vol. 101, pp. 297-302, May 30, 1991.
Luyten et al., "Skeletal tissue engineering: opportunities and challenges," Best Pract Res Clin Rheumatol., vol. 15, pp. 759-770, Dec. 2001.
Male, Immunology, An illustrated outline, $2^{nd}$ edition, Gower Medical Publishing, London, New York, 1991, p. 119.
Morrison et al., "Chimeric human antibody molecules: mouse antigen-binding domains with human constant region domains," Proc Natl Acad Sci U S A., vol. 81, pp. 6851-6855, Nov. 1984.
Neuberger et al., "A hapten-specific chimaeric IgE antibody with human physiological effector function," Nature, vol. 314, pp. 268-270, Mar. 21, 1985.
Newman et al., "'Primatization' of recombinant antibodies for immunotherapy of human diseases: a macaque/human chimeric antibody against human CD4," Biotechnology, vol. 10, pp. 1455-1460. Nov. 1992.
Nishimura et al., "Chondroprogenitor cells of synovial tissue," Arthritis Rheum., vol. 42, pp. 2631-2637, Dec. 1999.
Nygren, "Conjugation of horseradish peroxidase to Fab fragments with different hornebifunctionsi and heterofunctional cross-linking reagents. A comparative study," J Histochem CytoChem., vol. 30, pp. 407-412, May 1982.
Owens et al., "The genetic engineering of monoclonal antibodies." J Immunol Methods, vol. 168, pp. 149-165, 1994.
Pain et al., "Preparation of protein A-peroxidase monoconjugate using a heterobifunctional reagent, and its use in enzyme immunoassays," J Immunol Methods, vol. 40, pp. 219-230, 1981.
Parrott et al., "Metabolically biotinylated adenovirus for cell targeting, ligand screening, and vector purification," Mol Ther., vol. 8, pp. 688-700, Oct. 2003.
Pera et al., "Human embryonic stem cells," J Cell Sci., vol. 113, pp. 5-10, Jan. 2000.
Pittenger et al., "Multilineage potential of adult human mesenchymal stem cells," Science, vol. 284, pp. 143-147, Apr. 2, 1999.
Plow et al., "Ligand binding to integrins," J Biol Chem., vol. 275, pp. 21785-21788, Jul. 21, 2000.

(56) References Cited

OTHER PUBLICATIONS

Qurici et al., "Isolation of bone marrow mesenchymal stem cells by anti-nerve growth factor receptor antibodies," Exp Hematol., vol. 30, pp. 783-791, Jul. 2002.

Reyes et al., "Purification and ex vivo expansion of postnatal human marrow mesodermal progenitor cells.," Blood, vol. 98, pp. 2615-2625. Nov. 1, 2001.

Riechmann et al., "Reshaping human antibodies for therapy," Nature, vol. 332, pp. 323-327, Mar. 24, 1988.

Sato et al., "Reshaping a human antibody to inhibit the interleukin 6-dependent tumor cell growth," Cancer Res., vol. 53, pp. 851-856, Feb. 15, 1993.

Scouten, "A survey of enzyme coupling techniques," Methods Enzymol., vol. 135, pp. 30-65, 1987.

Scutt et al., "A semiautomated, 96-well plate assay for collagen synthesis," Anal Biochem., vol. 203, pp. 295-294, Jun. 1992.

Shimaoka et al., "Therapeutic antagonists and conformational regulation of integrin function," Nat Rev Drug Discov., vol. 2, pp. 703-716, Sep. 2003.

Solter et al., "Immunosurgery of mouse blastocyst," Proc Natl Acad Sci U S A., vol. 72, pp. 5099-5102, Dec. 1975.

Takada et al., "Molecular cloning and expression of the cDNA for alpha 3 subunit of human alpha 3 beta 1 (VLA-3), an integrin receptor for fibronectin, laminin and collagen," J. Cell Biol., vol. 115, pp. 257-266, Oct. 1991.

Takada et al., "The primary structure of the alpha 4 subunit of VLA-4: homology to other integrins and a possible cell-cell adhesion function," EMBO J., vol. 8, pp. 1361-1368, May 1989.

Tallheden et al., "Phenotypic plasticity of human articular chondrocytes," J Bone Joint Surg Am., vol. 85-A, Suppl. 2, pp. 93-100, 2003.

Talts et al., "Integrin gene targeting," Methods Mol Biol., vol. 129, pp. 153-187, 1999.

Tulla et al., "Selective binding of collagen subtypes by integrin alpha 1I, alpha 2I, and alpha 10I domains," J Biol Chem., vol. 276, pp. 48206-48212, Dec. 21, 2001.

Vaughan et al., "Human antibodies by design," Nat Biotechnol., vol. 16, pp. 535-539, Jun. 1998.

Velling et al., "cDNA cloning and chromosomal localization of human alpha(11) integrin. A collagen-binding, I domain-containing, beta(1)-associated integrin alpha-chain present in muscle tissues," J Biol Chem., vol. 274, pp. 25735-25742, Sep. 3, 1999.

Verhoeyen et al., "Reshaping human antibodies: grafting an antilysozyme activity," Science, vol. 239, pp. 1534-1536, Mar. 25, 1988.

Woessner, "Determination of hydroxyproline in connective tissues," The Methodology of Connective Tissue Research. $1^{st}$ Ed., Joynson-Bruvvers Ltd, Publisher, 1976.

Written Opinion of the International Searching Authority for Application No. PCT/SE2004/000580, Jul. 14, 2004.

Yednock et al., "Alpha 4 beta 1 integrin-dependent cell adhesion is regulated by a low affinity receptor pool that is conformationally responsive to ligand," J. Biol Chem., vol. 270, pp. 28740-28750, Dec. 1995.

Yoo et al., "The chondrogenic potential of human bone-marrow-derived mesenchymal progenitor cells," J Bone Joint Surg Am., vol. 80-A, pp. 1745-1757, Dec. 1998.

International Preliminary Examination Report for Application No. PCT/SE99/00544, Jun. 15, 2000.

International Preliminary Report on Patentability for Application No. PCT/SE2004/000580, Jul. 15, 2005.

International Search Report for Application No. PCT/SE2004/000580, Jul. 14, 2004.

International Search Report for Application No. PCT/SE99/00544, Jul. 30, 1999.

Weissman, I., "Stem Cells: Units of Development, Units of Regeneration, and Units in Evolution," Cell 100: 157-168 (2000).

Office Action dated Nov. 2, 2010, in Canadian Patent Application No. 2,522,645.

Bengtsson at al., "Characterization of the Mouse Integrin Subunit α 10 Gene and Comparison with its Human Homologue. Genomic Structure, Chromosomal Localization and Identification of Splice Variants," Matrix Biology 20:565-578 (2001).

"Poletics® Human Mesenchymal Stem Cells, Instructions for Use," LONZA, Lonza Waikersville, Inc., pp. 1-6 (2008).

Office Action dated May 6, 2010, in Australian Patent Application No. 2004228605.

* cited by examiner

74yr old knee cartilage

α10 (mAb)

αmouse Cy3

```
                        SEQUENCE LISTING

<160> NUMBER OF SEQ ID NOS: 4

<210> SEQ ID NO 1
<211> LENGTH: 18
<212> TYPE: DNA
<213> ORGANISM: Human

<400> SEQUENCE: 1
gcttccctgg tcttcctg                                                 18

<210> SEQ ID NO 2
<211> LENGTH: 18
<212> TYPE: DNA
<213> ORGANISM: Human

<400> SEQUENCE: 2
tctcaccacg gtcaccct                                                 18

<210> SEQ ID NO 3
<211> LENGTH: 18
<212> TYPE: DNA
<213> ORGANISM: Human
```

```
<400> SEQUENCE: 3 cagggggtgaa cgaggttt                                          18

<210> SEQ ID NO 4
<211> LENGTH: 21
<212> TYPE: DNA
<213> ORGANISM: Human

<400> SEQUENCE: 4
gaggtccaac ttctcccttc t                                       21
```

MONOCLONAL ANTIBODY CAPABLE OF BINDING INTEGRIN ALPHA 10 BETA 1

This application is a divisional of U.S. application Ser. No. 13/193,293, filed Jul. 28, 2011, which is a continuation of U.S. application Ser. No. 12/285,587, filed Oct. 9, 2008, now U.S. Pat. No. 8,012,696, which is a continuation of U.S. application Ser. No. 10/553,226, filed Feb. 6, 2006, now U.S. Pat. No. 7,452,677, which is the National Stage of International Application No. PCT/SE2004/000580, filed Apr. 14, 2004, which claims the benefit of priority of Swedish Application No. 0301087-3, filed Apr. 14, 2003, and U.S. Provisional Application No. 60/320,112, filed Apr. 16, 2003. All of the above applications are incorporated herein by reference in their entirety.

TECHNICAL FIELD

The invention relates to the generation of novel monoclonal antibodies or fragments thereof to the I-domain of the integrin alpha10 chain (α10), and a hybridoma cell-line expressing one such antibody as well as methods for using antibodies or fragments thereof for diagnostic, analytical and therapeutic purposes.

BACKGROUND OF THE INVENTION

Integrins

Integrins are glycoprotein heterodimers that contain a covalently associated alpha and beta subunit. The integrin subunits are transmembrane proteins possessing an extracellular domain for interacting with an extracellular matrix or cellular component, a transmembrane domain spanning the cell membrane, and a cytoplasmic domain for interacting with one or more skeletal components. To date, there are eighteen known alpha subunits that can combine with eight known beta subunits (Gullberg and Lundgren-Åkerlund, 2002), resulting in at least twenty-four different integrin molecules. Integrins can be grouped into subfamilies depending on which beta subunit they contain or alternatively the grouping can be based upon shared structural features of the alpha chain i.e. those integrins characterised by the presence of an additional region known as the I (inserted)-domain. This group includes nine members and thus represents half of the currently known integrin alpha chains (yelling 1999).

Integrin Alpha10Beta1

Recently we discovered a new collagen-binding integrin heterodimer (Camper et al 1998) that contains a novel alpha chain, designated alpha10. This alpha chain is associated with a beta1 subunit (alpha10beta1) and is a member of the I-domain containing integrins. Currently 4 collagen-binding I-domain containing integrins are known, alpha1beta 1, alpha2beta1, alpha10beta1 and alpha11beta1 (Gullberg and Lundgren-Åkerlund 2002).

Sequence analysis shows that alpha10 has the highest identity with alpha11 (43%) and an identity of 33% with alpha1 and 31% with alpha2.

Expression of Integrin Alpha10Beta1

Integrin alpha10beta1 is mainly expressed on chondrocytes in articular cartilage, in the vertebral column, in trachea and in the cartilage supporting the bronchi (Camper et al 2001). The integrin is also found in specialized fibrous tissues such as the fascia of skeletal muscle and tendon, in the ossification groove of Ranvier and in the aortic and atrioventricular valves of the heart (Camper et al 2001).

Function of Integrin Alpha10Beta1 in Cartilage

Chondrocytes are the only cell type in articular cartilage and are responsible for the coordinated synthesis and turnover of the extracellular matrix (ECM) components of the tissue. The two main components of the ECM, apart from water, are different types of collagen and the large aggregating proteoglycan aggrecan. The integrin alpha10beta1 on the chondrocyte cell surface mediates the binding of collagen to the chondrocyte and, like other integrin-extracellular matrix protein interactions (Heino 2000, Boudreau and Jones 1999, Hering 1999), is likely to be responsible for signalling the dynamic state of the surrounding matrix to the cell. Although collagen type II is likely to be an important ligand for alpha10beta1, it is not a prerequisite for alpha10beta1 expression since alpha10beta1 is also present in tissues that lack collagen type II. This implies that alpha10beta1 in vivo can bind to other important extracellular matrix ligands such as chondroadherin and other collagen types e.g. type I and type VI (Tulla et al. 2001).

Identifying tools for studying the biological role and the structural/functional relationships of this integrin with its various extracellular matrix ligands is therefore of great value. Such tools may be of a diagnostic nature for the detection of the presence of alpha10beta1, or maybe of therapeutic value in blocking or stimulating the activity of alpha10beta1.

Antibodies to Integrin Alpha10

Camper et al. (1998) describes the generation of polyclonal antibodies to the cytoplasmic domain of integrin alpha10beta1. The cytoplasmic domain consists of a 16 amino acid (Armulik 2000) sequence extending from the transmembrane domain. This domain is therefore is an ideal immunogen and production of polyclonal antibodies to this domain by immunisation with a peptide, whose sequence corresponds to a region within the cytoplasmic domain, is therefore a relatively simple, straightforward procedure routinely carried out to produce antibodies. (Harlow and Lane 1988). The polyclonal antibodies of Camper et al. (1998) generated in rabbit are of limited use since they are unable to be used on living cells due to their inability to penetrate cells.

General Structure of Naturally Occurring Antibodies

Naturally occurring antibodies comprise of two heavy chains linked together by disulphide bonds and two light chains, one light chain being linked to each heavy chain by disulphide bonds. Each heavy chain has at one end a variable domain ($V_H$) followed by a number of constant domains. Each light chain has a variable domain ($V_L$) at one end and a constant domain at its other end.

It is the variable domains of each pair of light and heavy chains that are directly involved in binding the antibody to the antigen (Harlow and Lane (1999)). The domains of the natural light and heavy chains have the same general structure and each domain comprises of four framework (Fr) regions, whose sequences are somewhat conserved, connected by three hyper-variable or complementarity determining regions (CDRs).

Monoclonal Antibodies of Non-Human Origin in Therapeutic Applications

Murine-derived monoclonal antibodies may cause an immunogenic response in human patients, reducing their therapeutic applicability. To circumvent this problem, humanised antibodies have therefore been developed in which the murine antigen binding variable domain is coupled to a human constant domain. (Morrison et al (1984), Boulianne et al (1984), Neuberger et al (1985)).

In a further effort to resolve antigen-binding functions of antibodies and to minimise the use of heterologous sequences in human antibodies, the CDRs or CDR sequences of murine antibodies are grafted onto the human variable region framework (Jones et al 1986, Riechmann et al 1988, Verhoeyen et al 1988). The therapeutic efficacy of this approach has been demonstrated previously (Reichmann et al (1988) and Hale et al (1989)).

Monoclonal Antibodies in Joint Diseases

Mature articular cartilage has no blood vessels, it is not innervated and normal mechanisms of tissue repair, involving the recruitment of cells to the site of damage does not occur. This means that cartilage has a very poor reparative response to injury and its irreparable breakdown is a common feature of degenerative joint diseases. Repair of such injuries has focused upon different tissue engineering strategies that involve the delivery or in situ mobilisation of cells capable of restoring the pathologically altered architecture and function of the tissue. Tissue engineering approaches for cartilage currently use isolated autologous cells derived from biopsies from healthy sites within the cartilage (autologous chondrocyte transplantation—ACT) (Brittberg 1999). Critical to ACT is the quality of the cells that are implanted back into the joint i.e. the cells should be chondrocytes capable of producing a hyaline-like cartilage (Jobanputra et al 2001).

An alternative strategy to the use of autologous chondrocytes is the use of stem cells with a chondrogenic differentiation capacity such as mesenchymal stem cells (FIG. 1) that can be used in vivo to repair or generate new cartilage (Jorgensen et al 2001, Johnstone and Yoo 2001). Whilst it is well documented that MSCs have the inherent potential to differentiate into osteogenic, chondrogenic, adipogenic and myocardiac cell lineages, there is currently no means of identifying the progenitor cell that will lead to these different lineages. Markers exist to indicate whether the cell is capable of expressing a cartilage phenotype i.e. collagen II and aggrecan, but these proteins are expressed extracellularly after synthesis, and cannot be used for isolation of a chondrogenic cell type.

Antibodies against extracellular integrin epitopes, in contrast to intracellular integrin epitopes, are in general difficult to generate due to a low or absent immunogenic capacity. Normally, this problem is solved by the skilled artisan by administering an adjuvant in parallel with the antigen of interest. Different adjuvants exist and by using one or another, or a combination thereof, a more or less general activation of the host's immune system is generated. Still, as of today's date and with the known accumulated knowledge of adjuvants, no monoclonal antibodies against the extracellular parts of integrin alpha10beta1 have been generated. Thus, an antibody useful in therapy, diagnosis and in situ studies of joint diseases is currently lacking due to the difficulty identified in generating such antibodies.

The one distinguishable feature common to the primary collagen binding integrins receptors is the existence of an I ("inserted") domain at the N-terminal of the alpha subunit. Only four collagen-binding integrins exist that contain an I-domain (integrin alpha1beta1, alpha2beta1, alpha10beta1 and alpha 11beta1). The I-domains still only show an overall identity of maximum of 60%. The I-domain of the integrin alpha10 is of particular interest since this domain contains unique structural differences compared to the I-domains of the other collagen-binding integrins. These differences include the number of cysteine residues, the high degree of positive amino acids and the recognition of distinct collagen subtypes (Gullberg and Lundgren-Åkerlund 2002, Tulla et al 2001). The I-domain thus comprises a unique ligand binding part and it is thus highly desirable to generate monoclonal antibodies against the I-domain of integrin alpha10, and integrin alpha10beta1.

It is further highly desirable to provide a tool that could identify and select cells of a chondrogenic nature for treatment purposes, in particular for the isolation of chondrocytes, mesenchymal progenitor cells and embryonic stem cells for tissue engineering of cartilage.

It is further highly desirable in the light of aforementioned problems to develop means and methods for identifying diagnostic and therapeutic tools in studying the biological role and the structural/functional relationships of the integrin alpha10beta1 with its various extracellular matrix ligands. Further, there is an unmet need to identifying blocking or neutralizing and stimulatory agents, particularly for chondrocytes, mesenchymal stem cells and other cells expressing the integrin alpha10beta1. In this respect, the present invention addresses these needs and interest.

SUMMARY OF THE INVENTION

In view of the foregoing disadvantages known in the art when identifying and selecting cells of a chondrogenic nature for treatment purposes, in particular for the identification and isolation of chondrocytes, mesenchymal progenitor cells and embryonic stem cells for tissue engineering of cartilage, or for identifying diagnostic and therapeutic tools in studying the biological role and the structural/functional relationships of the integrin alpha10beta1 with its various extracellular matrix ligands, the present invention provides a monoclonal antibody or fragments thereof, specific for the I-domain of the integrin alpha10beta1, a cell line producing said monoclonal antibody and as well as methods and uses for different diseases related to joints, cartilage and atherosclerosis.

One object with the present invention is to provide a highly specific antibody for binding to the extracellular I-domain of integrin alpha10beta1.

Thus, the present invention provides a monoclonal antibody or a fragment thereof binding to the extracellular I-domain of integrin alpha10beta1.

Also, the present invention provides a hybridoma cell line deposited at the Deutsche Sammlung von Microorganismen und Zellkulturen GmbH under the accession number DSM ACC2583.

Furthermore, the present invention also provides a monoclonal antibody or a fragment thereof binding to the extracellular I-domain of integrin alpha10beta1 produced by the hybridoma cell line deposited at the Deutsche Sammlung von Microorganismen und Zellkulturen GmbH under the accession number DSM ACC2583.

Still furthermore, the invention provides a method for isolating a population of mammalian mesenchymal stem cells. The method comprises the steps of
  a) providing a cell suspension comprising mammalian mesenchymal stem cells,
  b) contacting the cell suspension in a) with a monoclonal antibody or a fragment thereof binding to the extracellular I-domain of integrin alpha10beta1, under conditions wherein said monoclonal antibody or a fragment thereof forms an antibody-antigen complex with the extracellular domain of integrin alpha10beta1,
  c) separating cells binding to the monoclonal antibody or a fragment thereof in b), and optionally
  d) recovering cells binding to the monoclonal antibody or a fragment thereof in c) from said antibody or a fragment thereof,
thereby producing a population of mammalian mesenchymal stem cells, optionally free from said antibody or a fragment thereof.

Similarly, the invention provides a method for isolating a population of mammalian chondrocytes. The method comprises the steps of
  a) providing a cell suspension comprising chondrocytes,
  b) contacting the cell suspension in a) with a monoclonal antibody or a fragment thereof binding to the extracellular domain of integrin alpha10beta1, under conditions wherein said monoclonal antibody or a fragment thereof forms an antibody-antigen complex with the extracellular I-domain of integrin alpha10beta1,
  c) separating cells binding to the monoclonal antibody or a fragment thereof in b), and optionally
  d) recovering cells binding to the monoclonal antibody or a fragment thereof in c) from said antibody or a fragment thereof,
thereby producing a population of chondrocytes, optionally free from said antibody or a fragment thereof.

Similarly, the invention provides a method for isolating a sub-population of mammalian ES cells; the method comprises the steps of
  a) providing a cell suspension comprising ES cells,
  b) contacting the cell suspension in a) with a monoclonal antibody or a fragment thereof binding to the extracellular domain of integrin alpha10beta1, under conditions wherein said monoclonal antibody or a fragment thereof forms an antibody-antigen complex with the extracellular I-domain of integrin alpha10beta1,
  c) separating cells binding to the monoclonal antibody or a fragment thereof in b), and optionally
  d) recovering cells binding to the monoclonal antibody or a fragment thereof in c) from said antibody or a fragment thereof,
thereby producing a sub-population of mammalian ES cells, optionally free from said antibody or a fragment thereof.

Further embodiments of the methods above is wherein the monoclonal antibody or a fragment thereof binding to the extracellular domain of integrin alpha10beta1 is a monoclonal antibody or a fragment thereof binding to the extracellular I-domain of integrin alpha10beta1 produced by the hybridoma cell line deposited at the Deutsche Sammlung von Mikroorganismen and Zellkulturen GmbH under the accession number DSM ACC2583.

Further embodiments of the methods are wherein the monoclonal antibody or a fragment thereof is linked to a solid phase.

The invention also provides a population of mammalian mesenchymal stem cells, a population of mammalian chondrocytes, and a sub-population of mammalian embryonic stem cells obtainable by the methods described above.

The invention also provides uses of a monoclonal antibody or a fragment thereof binding to the extracellular I-domain of integrin alpha10beta1, for the preparation of a pharmaceutical composition for the treatment of a joint disease or atherosclerosis.

Further methods and uses are also provided and described in detail below.

SHORT DESCRIPTION OF DRAWINGS

FIG. 1 shows a schedule of lineage differentiation of totipotent embryonic stem (ES) cells to pluripotent adult stem cells capable of forming neural, haematopoietic, epithelial and mesenchymal stem cells (MSCs). Differentiation from ES cells to MSCs and further to chondrocytes shows the pathway of cells capable of expressing the integrin alpha10beta1.

FIG. 2 shows immunoprecipitation using the antibody 365 and the I-domain of integrin alpha10beta1. The antibody 365 is able to immunoprecipitate the whole integrin alpha10beta1 expressed on the surface of the alpha10-transfected C2C12 cells (lane 3); cytoplasmic polyclonal alpha10 antibody was used as a positive control (lane 1) and cytoplasmic polyclonal alpha11 antibody was used as a negative control (lane 2). The antibody 365 was specific for the alpha10beta1 integrin since it did not immunoprecipitate integrin alpha11beta1 from alpha11-transfected C2C12 cells (lane 6). Polyclonal serum against the cytoplasmic domain of integrin alpha11 subunit (lane 5) was used a positive control and cytoplasmic polyclonal alpha10 antibody was used as a negative control (lane4).

FIG. 3 shows a specificity test of the antibody 365 for alpha10 in ELISA. No binding to alpha1 or alpha11 is observed. The absorbance of the colorimetric change was determined at 492 nm.

FIG. 4 shows results from a cell adhesion assay. mAb365 modulates the binding of $\alpha10\beta1$ integrin to type II collagen under defined conditions. a) mAb365 inhibits binding of $\alpha10\beta1$-expressing C2C12 cells to collagen II in the presence of 1 mM $Mg^{2+}$ and 1 mM $Ca^{2+}$. Control (no Ab) and 1B4 (isotype control) showed no inhibition of binding. b) Binding of $\alpha11\beta1$-expressing C2C12 cells to type II collagen is not inhibited by mAb365. Control (no Ab) and 1B4 (isotype control) showed no inhibition of binding.

FIG. 5 shows identification of cells expressing alpha10 integrin by FACS-analysis. The antibody 365 bound to C2C12 cells transfected with human alpha10 integrin-subunit (upper middle panel). This was seen as a displacement in the FACS histogram to the right. The antibody 365 did not bind to C2C12 cells transfected with human alpha11 integrin-subunit (upper right panel) or untransfected C2C12 cells (upper left panel). The lower panels represent secondary antibody alone, which did not bind to any of the cells tested.

FIG. 6 shows the results of positive selection by MACS® of alpha10-expressing cells determined by flow cytometry analysis, FACS. Cells before selection, flow through and eluted cells were incubated with 365, and stained with PE labelled goat-anti-mouse IgG. Alpha10 positive populations are shifted to the right as displayed in histograms 5B.

FIG. 7 shows identification of a population of integrin alpha10-expressing hMNCs using the antibody 365 in MACS® analysis (lower panel). The upper panel shows MACS analysis in the absence of the antibody 365.

FIG. 8 shows detection of alpha10 in human articular cartilage using the antibody 365. Human articular cartilage sections were immunolocalised with the antibody 365 detected using a donkey anti-mouse secondary antibody labelled with Cy3 (FIG. 8a). Integrin alpha10beta1 expression on human chondrocytes is clearly show clear of the when using the antibody 365. Control (secondary antibody only) does not bind to the integrin alpha10beta1 (FIG. 8b).

FIG. 9 shows percentage of alpha10$^+$- and alpha10$^-$-cells detected with mAb365 in FACS-analysis. Cells were analyzed on day 1, or after 1, 2, and 6 weeks.

FIG. 10 shows Collagen type II and Collagen type I mRNA levels in human chondrocytes, separated upon the basis of their expression of alpha10, i.e. alpha10 +ve or alpha10 −ve, using mAb365 and magnetic cell sorting.

FIG. 11 shows that Mab365 recognises the alpha10 integrin expression on mouse chondrocytes. The histogram demonstrates the level of alpha10 and beta 1 integrin on mouse chondrocytes. Dotted line represents the cells stained with isotype control antibody, filled histogram the alpha10 stained with mAb365 and the solid line illustrates the beta1.

FIG. 12 shows the alpha10 integrin expression on human MSC. The histogram shows the level of alpha10 and beta 1 on hMSC. Dotted line represents the cells stained with isotype control antibody, filled histogram the cells stained with mAb365 expressing alpha10, and the solid line illustrates the integrin beta1 subunit.

DETAILED DESCRIPTION OF THE INVENTION

Definitions

Figure 1:
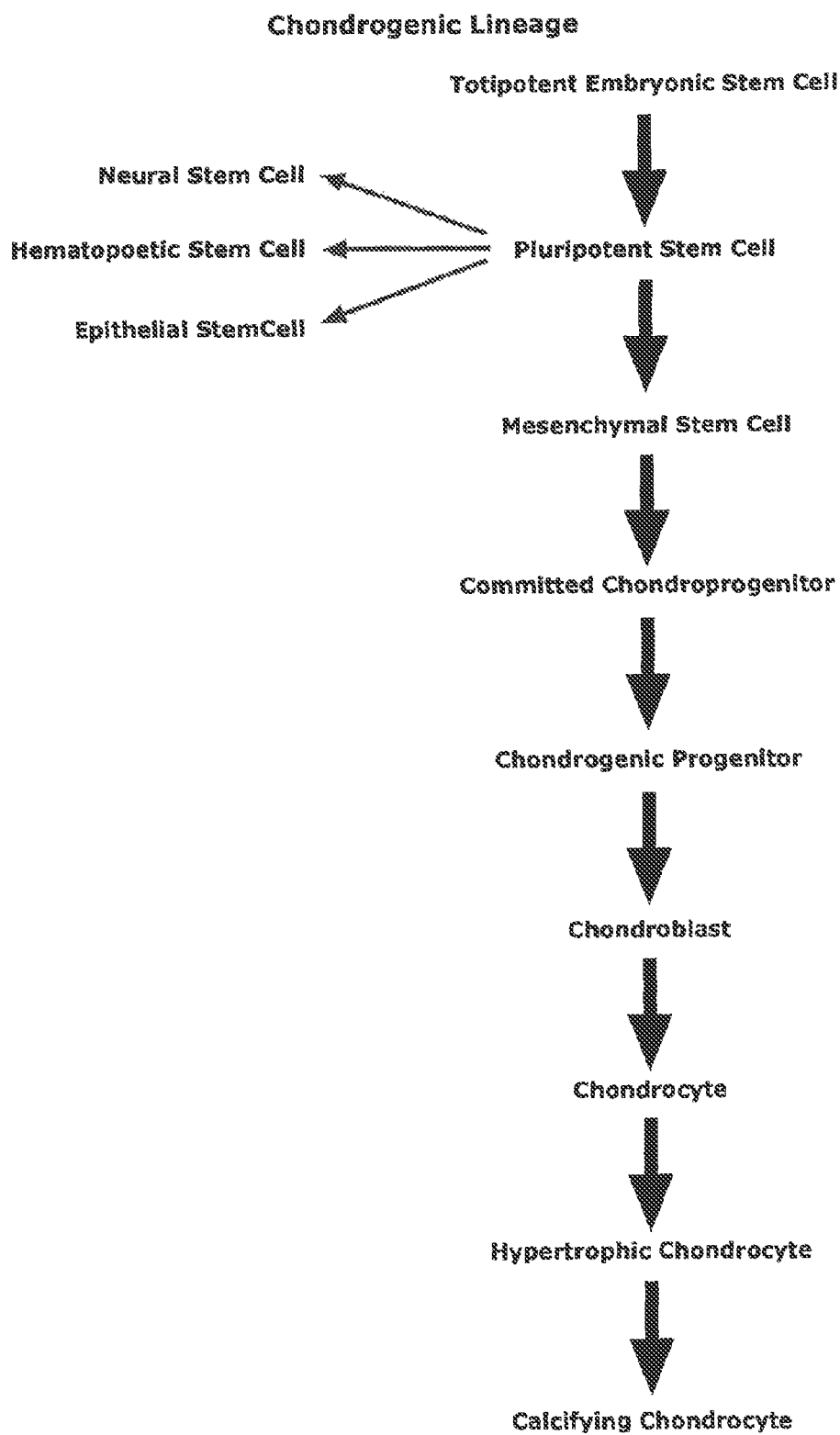

As used herein, the term "Mesenchymal stem cells" refers to cells that can differentiate into a variety of differentiated cell types, including cells forming bone, cartilage, muscle, tendons and ligaments, adipose tissue, and connective tissues.

As used herein, the term "Chondrocyte" refers to cells that comprise cartilage.

As used herein, the term "Chondrogenic" refers to those cells that have the potential to become chondrocytes.

As used herein, "pharmaceutical composition" means therapeutically effective composition according to the invention.

A "therapeutically effective amount", or "effective amount", or "therapeutically effective", as used herein, refers to that amount which provides a therapeutic effect for a given condition and administration regimen. This is a predetermined quantity of active material calculated to produce a desired therapeutic effect in association with the required additive and diluent; i.e., a carrier, or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent; i.e., carrier, or additive. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

As used herein, the term "to modulate" is intended to mean a capacity to affect a cell signalling effect directly or indirectly. To modulate thus means to act as an antagonist, i.e. partially or fully inhibit, reduce, alleviate, block or prevent; or to increase or stimulate, i.e. to act as an agonist. The modulation may be direct or indirect. By "indirect modulation" the effect is not via a natural ligand binding site but via another site on the same molecule or via another second molecule. This is in contrast to "direct modulation" acting via a natural ligand binding site.

A Hybridoma Cell Line

As revealed above, the present invention relates to antibodies, and hybridomas producing such antibodies, specific for the extracellular ligand-binding domains of integrin alpha10beta1.

More specifically the present invention relates to one generated hybridoma cell line producing an antibody specific for the extracellular ligand-binding I-domain of integrin alpha10beta1. Thus, a hybridoma cell line deposited at the Deutsche Sammlung von Microorganismen and Zellkulturen GmbH under the accession number DSM ACC2583 is disclosed.

A monoclonal antibody (mAb) or fragments thereof with specificity for the extracellular ligand-binding I-domain of alpha10beta1 is of great value in understanding the development, function, signalling, and differentiation of cells expressing this integrin, particularly mesenchymal stem cells, cells of a chondrogenic nature, chondrocytes, fibroblasts, tenocytes, myoblasts, osteoblasts, monocytes or macrophages.

FIG. 1 shows a schedule of lineage differentiation of totipotent embryonic stem (ES) cells to pluripotent adult stem cells capable of forming neural, haematopoietic, epithelial and mesenchymal stem cells (MSCs). Differentiation from ES cells to MSCs and further to chondrocytes shows the pathway of cells capable of expressing the integrin alpha10beta1.

Accordingly, the antibodies specific to the I-domain of the integrin subunit alpha10, such as the antibody 365 produced by the hybridoma cell line mAb 365 with deposit number DSM ACC2583, of the present invention may also be used to modulate receptor function in research and therapeutic applications. For instance, the antibodies described herein may act as antagonist to inhibit, i.e. reduce or prevent, or act as agonist, i.e. increase or stimulate, (a) binding e.g., of a ligand to the receptor, (b) a receptor signalling function, and/or (c) a stimulatory function. Antibodies that may act as agonists or antagonists of receptor function may block ligand binding directly or indirectly e.g., by causing a conformational change. For example, antibodies may inhibit receptor function by inhibiting binding of a ligand, or by desensitization, with or without inhibition of binding of a ligand. Antibodies which bind receptor may also act as agonists of receptor function, triggering or stimulating a receptor function, such as a signalling and/or a stimulatory function of a receptor e.g., modulating extracellular matrix (ECM) turnover, stimulating ECM synthesis.

Even more importantly, a modulatory, e.g. stimulatory, blocking or inhibitory, mAb that binds to cells expressing the integrin alpha10beta1 have a great potential as a therapeutic agent.

Furthermore, a mAb specific to the I-domain of integrin alpha10beta1 may be used as a drug delivery vehicle, or in combination with known drug delivery vehicles.

Furthermore, a mAb specific to the I-domain of integrin alpha10beta1 may be used to target the cell surface of cells expressing the integrin alpha10beta1 in gene therapy.

Generation of a mAb Specific for the I-Domain of the Integrin Alpha10 Subunit

Due to problems in generating monoclonal antibodies specific for the I-domain of integrin alpha10 subunit, a specific protocol for generating monoclonal antibodies has been generated and evaluated. The protocol is exemplified below by generation of a cell line mAb 365 producing the antibody 365.

For the generation of the hybridoma cell line mAb 365, producing an antibody binding to the extracellular alpha10beta1 I-domain, a gene knockout mouse of the integrin alpha10beta1 was used. The knockout mouse is described in SE Application no 0201130-2 filed on 12 Apr. 2002, included herein by reference.

After immunisation and boosting, spleen cells were fused with NSO cells and the resulting hybridoma cells cloned. Clone mAb 365 secreted a monoclonal antibody, 365, with specificity for alpha10beta1. As far as specificity is concerned, the monoclonal antibody binds to alpha10beta1 of both human and murine origin.

Example 1 gives a more detailed description of the generation of the cell line mAb 365.

According to the invention, a monoclonal antibody or fragments thereof against an extracellular region of the integrin alpha10beta1 produced by the hybridoma cell line mAb 365 described above with the accession number DSM ACC2583 is disclosed.

Monoclonal Antibody 365

The integrin alpha10beta1 is one of a member of 4 collagen binding I-domain containing integrins. Like the other I-domain-containing collagen binding integrins, the α10 I-domain contains a so-called MIDAS (metal ion-dependent adhesion site) motif. This motif is believed to have an important role in ligand binding to the I-domain. Upon ligand binding the conformation of the I-domain is altered and extensive changes occur in the secondary and tertiary structure of the domain (Emsley et al 2000).

Molecular modelling of the α10 I-domain, based on the α2 I-domain crystal structure, has revealed a higher degree of positively charged amino acids in the vicinity of the MIDAS motif when compared to the other I-domains (Tulla et al 2001, Plow et al 2000). This cluster, which appears not to be present in the other binding integrin I-domains, may provide α10 with specific functional characteristics thus making alpha10beta1 unique. The I-domain of alpha10beta1 is therefore a very interesting target for antibody generation.

Monoclonal antibodies or fragments thereof according to the invention may, thus, be used for identifying, isolating, enumerating, localizing, modulating, i.e., inhibiting or stimulating, mammalian cells, e.g. of human or murine origin. The cells may be e.g. mesenchymal stem cells, cells of a chondrogenic nature, chondrocytes, fibroblasts, tenocytes, myoblasts, osteoblasts, muscle cells, adipocytes, monocytes or macrophages.

Monoclonal antibodies or fragments thereof according to the invention, such as antibody 365 or fragments thereof, may be employed in any known analytical or diagnostic assay or methods, e.g. different immunomethods known to the skilled man in the art. Examples are immunoprecipitation, immunoaffinity purification, immunoblotting, immunolocalisation, competitive binding assays, direct and indirect sandwich assays and immunofluorescence. More examples are given in Zola 1987, and Sites et al 1982 incorporated herein by reference.

Further, the monoclonal antibody or fragments thereof may be used for various pharmaceutical products and for therapeutic use in mammals in the need thereof. Such pharmaceutical products include conjugation of monoclonal antibodies or fragments thereof according to the invention, such as antibody 365 or fragments thereof, to different drugs known in the art to affect, e.g. prevent, treat or alleviate, joint diseases. Examples are anti-inflammatory drugs such as non steroidal anti-inflammatory drugs (NSAIDS) for the treatment of joint diseases e.g. osteoarthritis, rheumatoid arthritis; conjugation to local anaesthetics for use post-operatively following orthopaedic surgery for the treatment of pain management; conjugation to hypolipidemic drugs for treatment of atherosclerotic plaque to produce a pharmaceutical product for therapeutic use; or factors, such as growth factors, for modulating matrix synthesis.

As used herein, the term "fragments thereof" of a monoclonal antibody includes a functional portion thereof e.g., antigen binding fragment such as including, but not limited to, Fv, Fab, Fab', F(ab')$_2$ fragments, single chain antibodies, and chimeric, humanized or primatized (CDR-grafted) antibodies, as well as chimeric or CDR-grafted single chain antibodies, and the like, comprising portions derived from different species, are also encompassed by the present invention and the term "antibody and fragments thereof". Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH.sub.1 domain and hinge region of the heavy chain. The various portions of these antibodies can be joined together chemically by conventional techniques, or can be prepared as a contiguous protein using genetic engineering techniques.

Murine-derived monoclonal antibodies may cause an immunogenic response in human patients, reducing their therapeutic efficacy. To circumvent this problem, humanised antibodies have therefore been developed in which the murine antigen binding variable domain is coupled to a human constant domain. (Morrison et al (1984), Boulianne et al (1984), Neuberger et al (1985)).

To minimise the use of heterologous sequences in human antibodies that may cause an immunological response in a human, the CDRs or CDR sequences of murine antibodies are grafted onto the human variable region framework (Fr) see e.g. Jones et al 1986, Riechmann et al 1988, Verhoeyen et al 1988 incorporated herein by reference. The therapeutic efficacy of this approach has been demonstrated previously by e.g. Reichmann et al (1988) and Hale et al (1989), both incorporated herein by reference.

The term "humanized immunoglobulin" as used herein refers to an immunoglobulin comprising portions of immunoglobulins of different origin, wherein at least one portion is of human origin. Efficient procedures for constructing humanized antibodies have been developed—see Funaro et al 1996, Vaughan et al 1998, both incorporated herein by reference. Accordingly, the present invention relates to a humanized immunoglobulin which binds the I-domain of mammalian integrin alpha10beta1, said immunoglobulin comprising an antigen-binding region of non-human origin, e.g., rodent such as murine, and at least a portion of an immunoglobulin of human origin e.g., a human framework region, a human constant region or portion thereof. For example, the humanized antibody can comprise portions derived from an immunoglobulin of non-human origin with the requisite specificity, such as a mouse, and from immunoglobulin sequences of human origin e.g., a chimeric immunoglobulin, joined together chemically by conventional techniques, e.g., synthetic, or prepared as a contiguous polypeptide using genetic engineering techniques, e.g., DNA encoding the protein portions of the chimeric antibody can be expressed to produce a contiguous polypeptide chain.

Another example of a humanized immunoglobulin of the present invention is an immunoglobulin containing one or more immunoglobulin chains comprising a CDR of non-human origin e.g., one or more CDRs derived from an antibody of non-human origin, and a framework region derived from a light and/or heavy chain of human origin, e.g., CDR-grafted antibodies with or without framework changes. In one embodiment, the antigen-binding region of the humanized immunoglobulin is derived from the antibody 365, disclosed in the present invention comprising CDR1, CDR2 and CDR3 of the heavy and light chain of a human antibody. Chimeric or CDR-grafted single chain antibodies are also encompassed by the term humanized immunoglobulin.

Humanized immunoglobulins can be produced using synthetic and/or recombinant nucleic acids to prepare genes, e.g., cDNA, encoding the desired humanized chain. For example, nucleic acid, e.g., DNA, sequences coding for humanized variable regions can be constructed using PCR mutagenesis methods to alter DNA sequences encoding a human or humanized chain, such as a DNA template from a previously humanized variable region—see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991) all incorporated herein by reference. Using these or other suitable methods, variants can also be readily produced. In one embodiment, cloned variable regions can be mutagenized, and sequences encoding variants with the desired specificity can be selected, e.g., from a phage library; see e.g., Krebber et al., U.S. Pat. No. 5,514,548; Hoogenboom et al., WO 93/06213, published Apr. 1, 1993) all incorporated herein by reference.

Nucleic acids encoding a chimeric or humanized chain can be expressed to produce a contiguous protein. See, e.g., Cabilly et al., U.S. Pat. No. 4,816,567; Cabilly et al, European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; and Queen et al., U.S. Pat. Nos. 5,585,089, 5,698,761 and 5,698,762. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies, all incorporated herein by reference.

In one embodiment of this invention the framework regions or CDRs or CDR sequences encoding fragments of antibodies according to the invention, such as antibody 365, are substituted into a suitable human antibody.

In addition, functional fragments, i.e. antigen binding fragments of antibodies, including fragments of chimeric, humanized, primatized or single chain antibodies, can also be produced. Functional fragments of the foregoing antibodies retain at least one binding function and/or modulation function of the full-length antibody from which they are derived. Preferred functional fragments retain an antigen-binding function of a corresponding full-length antibody, i.e., the ability to bind the I-domain of mammalian integrin alpha10 or integrin alpha10beta1. Particularly preferred functional fragments retain the ability to inhibit one or more functions characteristic of the I-domain of mammalian integrin alpha10 or integrin alpha10beta1, such as a binding activity, a signalling activity, and/or stimulation of a cellular response. For example, in one embodiment, a functional fragment may modulate, i.e. inhibit or stimulate, the interaction of the I-domain of mammalian integrin alpha10 or integrin alpha10beta1 with one or more of its ligands e.g., a cell matrix ligand such as an extracellular matrix molecule, e.g. collagen types I-VI, IX, X, XI and/or other extracellular matrix proteins such as chondroadherin and other leucine-rich repeat proteins (LRR proteins), matrilin, laminin, and tenascin and/or can modulate one or more receptor-mediated functions, such as regulation of collagen turnover, regulation of matrix metalloproteinase expression, regulation of ECM molecule turnover.

Humanisation of the mouse monoclonal antibodies or fragments thereof according to the invention, such as antibody 365 or fragments thereof, may, for example, be performed in the following manner:
1) RNA is harvested from mouse hybridoma clone of the present invention.
2) PCR primers that hybridise to the 5' ends of the mouse leader sequences and to the 5' prime ends of the mouse constant regions are designed for cloning the kappa light chain variable regions and heavy chain variable regions.
3) Complementary DNA (cDNA) is synthesised from total RNA, followed by PCR amplification with light and heavy chain specific primers.
4) Positive bacterial colonies containing mouse monoclonal antibody variable regions are screened.
5) Cloned mouse monoclonal antibody leader-variable regions are modified at the 5'- and 3'-ends, using PCR primers to create restriction enzyme sites for insertion into expression vectors to incorporate sequences for efficient eukaryotic translation, and to incorporate splice-donor sites for RNA splicing of the variable and constant regions.
6) The adapted mouse monoclonal antibody light and heavy chain leader-variable regions are inserted into vectors containing, for example, human cytomegalovirus enhancer and promoter for transcription, a human light or heavy chain constant region, a neomycin gene for selection of transformed cells, and the simian virus 40 origin of replication in COS cells.

Said vectors are designed to express chimeric or reshaped human light and heavy chains in mammalian cells. The design and construction of an engineered human antibody requires analysis of the primary amino acid sequences of the mouse monoclonal antibody variable regions further described below to identify the residues most critical in forming the antigen-binding site.

The mouse CDRs are then joined to the FRs from selected human variable regions to form a humanised antibody.

The Primary Amino Acid Sequence of Monoclonal Antibody

The design and construction of an engineered human antibody or fragments thereof requires analysis of the primary amino acid sequences. Deriving the DNA sequence, and thereby the primary amino acid sequence, of an antibody produced by a hybridoma is as of today easily done for the skilled artisan. The information retrieved from the mouse monoclonal antibody variable regions, such as the antibody 365, is used to identify the residues most critical in forming the antigen-binding site of said antibody.

Thus, nucleic acids encoding the heavy and/or light chains of the antibodies or portions thereof can be obtained and used in accordance with recombinant DNA techniques for the production of the specific immunoglobulin, immunoglobulin chain, or variants thereof, e.g., humanized immunoglobulins, in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors, e.g., expression vectors, and introduced into a suitable host cell by an appropriate method, e.g., transformation, transfection, electroporation, infection, such that the nucleic acid is operably linked to one or more expression control elements, e.g., in the vector or integrated into the host cell genome.

As used herein "recombinant expression vector", or "expression vector" refers to a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product For production, host cells can be maintained under conditions suitable for expression e.g., in the presence of inducer, suitable media supplemented with appropriate salts, growth factors, antibiotic, nutritional supplements, etc., whereby the encoded polypeptide is produced. If desired, the encoded protein can be recovered and/or isolated, e.g., from the host cells, or medium, or milk. It will be appreciated that the method of production encompasses expression, transient or constantly, in a host cell of a transgenic animal.

The following is an example of a method for sequencing a mouse monoclonal antibody, such as the antibody 365, further described by Jarrin and Andrieux (1999) incorporated herein by reference. Briefly:

1) RNA is extracted from the hybridoma cell line of the present invention by standard methods, for example the method of Gough (1988) incorporated herein by reference.
2) Reverse transcriptase is performed by incubating RNA with oligonucleotide primers capable of binding specifically to each of the immunoglobulin heavy and light chains of murine antibodies, or by general oligo d(T)-primers.
3) PCR is performed to amplify the cDNA and the amplification products analysed on an agarose gel.
4) PCR products corresponding to the variable region of each of the immunoglobulin chains are digested with restriction enzymes such as BmaH1/EcoR1 for the light chains and Pst1/Cla1 for the heavy chains.
5) A vector, for example pBlueScript, is digested with restriction enzymes corresponding to those necessary for cloning of each chain of the mouse monoclonal antibody.
6) Digested immunoglobulin chains are incubated with digested vector and ligation performed.
7) Electrocompetent bacteria, such as DH5alpha bacteria, are transformed with the ligation product by electroporation.
8) Bacteria are selected on LB agar plates containing, for example, ampicillin, X-Gal and IPTG. Only efficiently transformed bacteria plus vector insert result in white colonies.
9) Plasmid DNA is purified is sequencing performed using an appropriate kit. Amino acid sequences of both the heavy and light variable regions of the antibody can thus be deduced from the nucleotide sequences determined above.

Modulation of Cells Using Antibody or Fragment Thereof

The monoclonal antibody or fragment thereof according to the invention, such as the antibody 365, may be used to modulate the activity of cells expressing alpha10beta1, as described in the paragraphs above. By "modulate activity of cells" it is further intended to mean activating the function or biological activity of alpha10beta1, or inhibiting by e.g. partial or complete blocking or neutralizing, thereby substantially inhibiting the function or biological activity of alpha10beta1. Typically a blocking or neutralizing antibody or fragments thereof will inhibit the binding of alpha10beta1 to a cell matrix ligand such as collagen types I-VI, IX, X, XI and/or other extracellular matrix molecules such as chondroadherin and other leucine-rich repeat proteins (LRR proteins), matrilin, laminin, and tenascin.

Cells to be modulated are cells expressing the integrin alpha10beta1 and may be, but are not limited to, mesenchymal stem cells, embryonic stem (ES) cells, chondrocytes, fibroblasts, adipocytes, muscle cells, tenocytes, myoblasts, osteoblasts, monocytes and macrophages.

In inhibiting the binding of extracellular matrix molecules the monoclonal antibody may induce the cell to which it binds to stimulate the expression and/or synthesis of one or more factors such as growth factors, cytokines, transcription factors, and/or ECM molecules.

Modulation is generally achieved by incubating the cell of interest, in vivo or in vitro, with a monoclonal antibody, such as antibody 365, in empirically determined amounts. The effect is then assayed or determined in a suitable way. In vitro a typical concentration can range from 0.1 µg/ml-100 µg/ml, however, other concentration regimens may be useful and are not excluded. In vivo, depending on the type and severity of the disease in question, about 0.015 to 15 mg of antibody or a fragment thereof/Kg of patient weight is an initial candidate dosage for administration to the patient.

Use of Antibody or a Fragment Thereof in ELISA Assay

Competitive binding assays rely on the ability of a labelled standard, which may be alpha10beta1 or an immunologically reactive portion thereof such as the I-domain, to compete with the test sample analyte, i.e. alpha10beta1 or alpha10, for binding of a limited amount of antibody. The amount of alpha10 or alpha10beta1 in the test sample e.g. human blood, human synovial fluid, fluid surrounding the tendon, i.e. tenosynovial fluid, is then assayed as inversely proportional to the amount of standard that becomes bound to the antibodies.

Sandwich assays involve the use of two antibodies, each capable of binding to a different immunogenic portion or epitope, of the protein to be detected. In a sandwich assay, the test sample analyte is bound by a first antibody or fragments thereof which is immobilised on a solid support, and thereafter a second antibody or fragments thereof bind to the analyte, thus forming an insoluble three-part complex. The second antibody or fragments thereof may itself be labelled with a detectable moiety in a direct sandwich assay, or may be measured using an anti-immunoglobulin antibody or fragments thereof that is labelled with a detectable moiety in an indirect sandwich assay. For example, one type of sandwich assay is an ELISA (enzyme-linked immunosorbent assay), in which case the detectable moiety is an enzyme.

A monoclonal antibody or fragment thereof according to the invention may be used in such assays. One example of monoclonal antibody according to the invention to be used is the antibody 365.

Use of MSCs Isolated Using an Antibody Binding to the Extracellular Part of the I-Domain of Integrin Alpha10Beta1 or a Fragment Thereof In an additional aspect, the present invention is directed to various methods and uses of utilizing ES cells, MSCs, MSCs with a chondrogenic nature or chondrocytes, or other progenitor cells expressing alpha10beta1 of mammalian, such as murine or human, origin and a monoclonal antibody binding to the extracellular part of the I-domain of integrin alpha10beta1 or a fragment thereof, such as e.g. the antibody 365 or a fragment thereof, produced by the present invention for therapeutic and/or diagnostic purposes. For example, human MSCs or progenitor cells may find use in:
1) regenerating mesenchymal tissues that have been damaged through acute injury, abnormal genetic expression or acquired disease.
2) treating a host with damaged mesenchymal tissue by removal of small aliquots of e.g. bone marrow or any other tissue including MSC, isolation of their MSCs and treatment of the damaged tissue with MSCs combined with a biocompatible carrier suitable for delivering the MSCs to the damaged tissue site(s).

Compositions according to the present invention, which contain MSCs, or MSCs with a chondrogenic nature, or chondrocytes, are especially useful for facilitating repair, reconstruction and/or regeneration of a connective tissue defect. Connective tissue, as used herein, includes cartilage, bone, ligament, tendon, stroma and muscle. Connective tissue defects include any damage or irregularity compared to normal connective tissue, which may occur due to trauma, disease, age, birth defect, surgical intervention etc. The use of antibodies according to the invention disclosed herein, such as e.g. the antibody 365, are especially suitable for use in orthopaedic surgical procedures.

Use of Chondrocytes Isolated Using a Monoclonal Antibody Binding to the Extracellular Part of the I-Domain of Integrin Alpha10Beta1 or a Fragment Thereof In an additional aspect, the present invention is directed to various methods of utilizing the chondrocytes and the monoclonal antibody binding to the extracellular part of the I-domain of integrin alpha10beta1 or a fragment thereof produced for therapeutic and/or diagnostic purposes. For example, human chondrocytes may find use in:
1) regenerating cartilage that has been damaged through acute injury, abnormal genetic expression or acquired disease.
2) treating a host with damaged chondrocytes by removal of small cartilage biopsies, isolation of the chondrocytes, culture of the chondrocytes in vitro and reintroduction of the expanded chondrocytes into the human patient at the site(s) of cartilage damage.

Cartilage defects include any damage or irregularity compared to normal cartilage tissue, which may occur due to trauma, mechanical loading, disease, age, birth defect, surgical intervention etc. The use of a monoclonal antibody binding to the extracellular part of the I-domain of integrin alpha10beta1 or a fragment thereof, such as the antibody 365 or fragments thereof, herein is especially suitable for use in orthopaedic surgical procedures.

Use of Embryonic Stem Cells Isolated Using Antibody Binding to the Extracellular Part of the I-Domain of Integrin Alpha10Beta1 or a Fragment Thereof In an additional aspect, the present invention is directed to various methods of utilizing the ES cells and the monoclonal antibody binding to the extracellular part of the I-domain of integrin alpha10beta1 or a fragment thereof or fragments thereof produced for therapeutic and/or diagnostic purposes. For example, human ES cells may find use in e.g.
a) regenerating mesenchymal tissues that have been damaged through acute injury, abnormal genetic expression or acquired disease, and/or
b) treating a host with damaged mesenchymal tissues by isolation of ES cells from the inner cell mass (ICM) of the blastocyst of a 4-6 day old human embryo and culturing these cells in vitro on mouse embryonic fibroblast feeder cells to allow the cells to proliferate. Removal of growth factors or fibroblast growth factor-2 (FGF-2) from the medium causes the cells to differentiate at which point the population of cells expressing the integrin alpha10beta1 can be identified by using the antibody 365. Such cells can be combined with a biocompatible carrier and surgically inserted into the damaged tissue site(s).

A Method for Isolating a Population of Mammalian Mesenchymal Stem Cells

According to the invention a method for isolating a population of mammalian mesenchymal stem cells (MSCs), is disclosed. The method comprises the steps of:
a) providing a cell suspension comprising mammalian mesenchymal stem cells,
b) contacting the cell suspension in a) with a monoclonal antibody or fragments thereof according to the invention binding to the extracellular domain of integrin alpha10beta1, under conditions wherein said monoclonal antibody or fragments thereof form an antibody-antigen complex with the extracellular domain of integrin alpha10beta1,
c) separating cells binding to the monoclonal antibody or fragments thereof in b), and optionally
d) recovering the cells binding to the monoclonal antibody or fragments thereof in c) from said antibody or fragments thereof, thereby producing a population of mammalian mesenchymal stem cells, optionally free from said antibody or fragments thereof.

The cell suspension provided in a) above, comprising mammalian MSCs may be isolated from bone marrow, peripheral blood, cord blood, liver, bone, cartilage, muscle, perichondrium, periosteum, synovial tissue, fat or any tissue comprising MSCs. The cell suspension may further be isolated from mammalian iliac crest, femora, tibiae, spine, rib or other medullary spaces. Other sources of human MSCs include embryonic yolk sac, placenta, and umbilical cord.

If the population of cells is collected from BM, only 0.01-0.001% of the starting population, or "crude population", are MSCs. Though, this may vary between different donors.

In one further embodiment, the mammalian MSCs are human MSCs.

In one further embodiment, the mammalian MSCs are murine MSCs.

In one further embodiment the monoclonal antibody or fragment thereof is the antibody 365 according to the invention.

In one further embodiment, the culture above is a culture for 2-4 weeks.

In one embodiment, the method for isolating a population of MSCs further comprises the steps of
a) collecting bone marrow aspirate (5-30 ml) from a human patient into a syringe containing 6000 units of e.g. heparin to prevent clotting,
b) washing the marrow sample with e.g. Dulbecco's phosphate-buffered saline (DPBS) or any similar saline solution, and recovering the cells after centrifugation at 900 g, and repeating this procedure once more.
c) loading the cells onto 25 ml of Percoll of a density of 1.073 g/ml in a 50-ml conical tube and separating the cells by centrifugation at 1100 g for 30 min at 20° C.,
d) collecting the nucleated cells from the interface, diluting with two volumes of DPBS, and collecting by centrifugation at 900 g. Resuspending the cells counting the cells, and plating out the cells at the required density, suitable 200,000-cells/cm$^2$,
e) culturing the cells in Dulbecco's modified Eagle's medium (DMEM) or any other suitable medium (low glucose) containing 10% foetal bovine serum (FBS). Replacing the medium at 24 and 72 hours and every third or fourth day thereafter, and f) subculturing the hMSCs that grow as symmetric colonies at 10 to 14 days by treatment with 0.05% trypsin and 0.53 mM EDTA for 5 min, rinsed from the substrate with serum-containing medium, collected by centrifugation at 800 g for 5 min, and seeded into fresh flasks at 5000 to 6000 cells/cm$^2$.

The separation of MSCs is a selection and isolation step for separating the identified MSCs. Various techniques known to the skilled artisan may be employed to separate the cells by initially removing cells dedicated to other lineages than MSCs.

The antibody or fragments thereof according to the invention may be attached to a solid support to allow for a highly specific separation. The particular procedure for separation employed, e.g. centrifugation, mechanical separation, such as columns, membranes or magnetic separation, should maximize the viability of the fraction to be collected. Various techniques of different efficacy may be employed known to a person skilled in the art. The particular technique employed will depend upon efficiency of separation, cytotoxicity of the methodology, ease and speed of performance, and necessity for sophisticated equipment and/or technical skill.

Procedures for separation of MSCs from a cell suspension aided by the antibody or fragments thereof according to the invention may include magnetic separation, using e.g. antibody-coated magnetic beads, affinity chromatography based on the antibody or fragments thereof according to the invention, and "panning" with said antibody or fragments thereof attached to a solid matrix, e.g., a plate, or other convenient techniques. Magnetic cell sorting are well known to a person skilled in the art and is described in, for example, Haukanes and Kvam (1993) Biotechnology 11(1):60-63, and Quirici et al (2002) Exp. Hematol 30:783-791.

Techniques providing accurate separation include fluorescence activated cell sorters by the use of the antibody or fragments thereof according to the invention, which can have varying degrees of sophistication, e.g., a plurality of colour channels, light scattering detecting channels, impedance channels, etc. known to the skilled man in the art.

In one embodiment, a first enrichment step of MSCs in the provided cell population is made. This first selection may be a negative selection of the MSCs, i.e. other lineage-committed cells are depleted, or removed, from the initial population of cells.

In still a further embodiment, the first enrichment is a positive selection of MSCs that may be repeated until the desired purity of the MSCs is achieved.

Alternatively, MSC cells may be isolated from bone marrow. Stem cells may be isolated from human bone marrow by standard methods (Quirici et al (2002) Exp. Hematol 30(7): 783-791). Alternatively, commercial MSC may be used (Poietics).

If isolated from bone marrow, bone marrow may be taken from healthy allogeneic bone marrow transplantation donors, collected in heparinized tubes and layered onto Lymphoprep™ (density 1.077 g/ml, Nycomed, Norway) according to the manufactures' description. The low-density mononuclear cells (LD-MNC) are then isolated from the human bone marrow cells by centrifugation. The LD-MNCs are washed twice in PBS and resuspended in MSCGM (mesenchymal stem cell growth medium) (Poetics, Cambrex Bio Science Walkersville, Inc.).

Mesenchymal Stem Cells may then be purified from LD-MNCs by the following standard methods: by adhesion to plastic (Pittenger et al (1999) Science 184:143), CD45$^-$/alpha-glycophorin A$^-$ (Reyes et al (2001) Blood. 98(9):2615-25), CD105$^+$ (Conrad et al. (2002). Exp Hematol. 30(8):887-95) and NGFR$^+$ isolation (Quirici et al. (2002) Exp Hematol. 30(7):783-91).

A Method for Isolating a Population of Mammalian Chondrocytes

According to the invention a method for isolating a population of mammalian chondrocytes is disclosed. The method comprises the steps of a) providing a cell suspension comprising chondrocytes, b) contacting the cell suspension in a) with a monoclonal antibody or a fragment thereof according to the invention, binding to the extracellular domain of integrin alpha10beta1, under conditions wherein said monoclonal antibody or a fragment thereof forms an antibody-antigen complex with the extracellular I-domain of integrin alpha10beta1, c) separating cells binding to the monoclonal antibody or a fragment thereof in b), and optionally d) recovering cells binding to the monoclonal antibody or a fragment thereof in c) from said antibody or a fragment thereof, thereby producing a population of mammalian chondrocytes, optionally free from said antibody or a fragment thereof.

The cell suspension provided in a) above, comprising mammalian chondrocytes may be isolated from cartilage.

In one further embodiment, the monoclonal antibody or fragment thereof is the antibody 365 or a fragment thereof.

In one further embodiment, the mammalian chondrocytes are human chondrocytes.

In one further embodiment, the mammalian chondrocytes are murine chondrocytes.

In one further embodiment, the method for isolating a population of chondrocytes comprises the steps of 1) harvesting healthy cartilage from e.g. the femoral chondyle and/or tibial plateau of a human specimen.

2) enzymatically digesting the cartilage with enzymes such as pronase or hyaluronidase for 1 hour at 37° C. in cell medium (Dulbecco's modified Eagles medium (DMEM) containing foetal calf serum (FCS), penicillin/streptomycin and L-glutamine.)

3) discarding the supernatant after pronase or hyaluronidase digestion and further digesting the cartilage with collagenase in DMEM for 3 hrs at 37° C.

4) allowing the digest to settle, removing the supernatant from the digest and filtering through a 75 μM filter.

5) centrifuging the supernatant for 8 minutes at 1800 g and washing the supernatant with PBS (Ca$^{2+}$ and Mg$^{2+}$ free) containing 5% FCS.

6) resuspending the washed cells in DMEM and incubating at 37° C. under an atmosphere of 5% CO$_2$.

7) redigesting the remaining tissue with collagenase in DMEM until all the tissue has digested.

8) repeating step 5, pooling all chondrocytes obtained from digestion, centrifuging and resuspending in DMEM for cell counting.

9) culturing the chondrocytes in DMEM medium supplemented accordingly.

The separation of chondrocytes is a selection and isolation step for separating the identified chondrocytes. Various techniques may be employed to separate the cells by initially removing cells other than chondrocytes which do not express the other known chondrocyte markers aggrecan and collagen II.

The antibody or fragments thereof according to the invention may be attached to a solid support to allow for a highly specific separation, similar to that described in the method for isolation of MSCs above. The particular procedure for separation employed, e.g. centrifugation, mechanical separation, such as columns, membranes or magnetic separation, should maximize the viability of the cell fraction to be collected. Various techniques of different efficacy may be employed known to a person skilled in the art. The particular technique employed will depend upon efficiency of separation, cytotoxicity of the methodology, ease and speed of performance, and necessity for sophisticated equipment and/or technical skill.

In one embodiment, a first enrichment step of chondrocytes in the provided cell population is made. This first selection may be a negative selection of the chondrocytes, i.e. other cells not being chondrocytes cells are depleted, or removed, from the initial population of cells.

In still a further embodiment, the first enrichment is a positive selection of chondrocytes that may be repeated until the desired purity of the chondrocytes is achieved.

Alternatively, isolation of an integrin alpha10 positive cell population for differentiation to chondrocytes may be performed.

Integrin alpha10 positive cells can be isolated by the following methods: Cells are labelled with 10 µg/ml mAb365 (alpha10 integrin receptor) for 20 minutes at 4° C., washed and labelled with goat anti-mouse IgG micro beads (Miltenyi Biotec, Germany) for 20 minutes in 4° C. The alpha10 positive cells were isolated by positive selection with an LS midiMACS column (Miltenyi Biotec, Germany). This procedure is performed according to the manufacturers' instructions.

In still another method LD-MNCs are taken and a CD45/alpha-glycophorin A depletion kit (Miltenyi Biotec, Germany) is used. The negative (unmarked) cells are then labelled with 10 µg/ml mAb365 (alpha10 integrin receptor) for 20 minutes at 4° C., washed and labelled with goat anti-mouse IgG micro beads (Miltenyi Biotec, Germany) for 20 minutes in 4° C. The alpha10 positive cells are then isolated by positive selection with an LS midiMACS column (Miltenyi Biotec, Germany).

In still another method CD105 (Miltenyi Biotec, Germany) micro beads are used, expand the cells and labelled with 10 µg/ml mAb365 (alpha10 integrin receptor) for 20 minutes at 4° C., washed and labelled with goat anti-mouse IgG micro beads (Miltenyi Biotec, Germany) for 20 minutes in 4° C. The alpha10 positive cells are then isolated by positive selection with an LS midiMACS column (Miltenyi Biotec, Germany).)

In still another embodiment, a population of human chondrocytes are provided by extraction from human articular cartilage. One way of extracting a chondrocyte enriched population is described by Brittberg et al (1994) in N. Engl. J. Med. (331:889-895). MAb365 may then be used for further enrichment of an alpha10-positive chondrocytic according to the method for isolating a population of mammalian chondrocytes as disclosed above.

Chondrocytes may be identified in further by measuring mRNA production of collagen type II, or by measuring the actual collagen type II production. mRNA may be measured by general protocols known to the skilled man in the art for RT-PCR (reverse transcriptase polymerase reaction). Specific primers for collagen type II are For measurements of collagen content, either the total amount of collagen can be determined using the hydroxyproline assay (Woessner J. F 1976 In: The Methodology of Connective Tissue Research. Ed: Hall D pp 227-233) or collagen synthesis can be measured by radiolabelling with $^3$H Proline (Scutt et al (1992) Anal. Biochem 203:290-294). Other similar methods known to a person skilled in the art may also be used.

As an example, measurement of hydroxyproline content may be performed in the following manner: Samples containing collagen (typically collagen type II) are hydrolysed in 6.0 M HCl for 16 hours at 110° C. to liberate hydroxyproline.

After neutralization each sample is diluted at least 15 times to prevent the salt concentration from influencing the assay. The samples are then dried under vacuum.

Example of one method that may be used:

a. Samples (1-5 µg of hydroxyproline) are made up to 2.0 ml with assay buffer.

b. Add 1.0 ml of Chloramine-T reagent and stand for 20 minutes at room temperature.

c. Add 1.0 ml of freshly prepared dimethylaminobenzaldehyde reagent and mix thoroughly.

d. Incubate the tubes at 60° C. for 15 minutes and cool in tap water for 5 minutes.

e. Measure the absorbance at 550 nm within 45 minutes.

Note: The hydrolysate may be passed over short columns of Dowex—50-x-8 (H+ form, 200-400 mesh) to remove coloured material and impurities if necessary.

Reagents:

1. Stock buffer contains 50 g of citric acid ($H_2O$), 12 ml of glacial acetic acid, 120 g of sodium acetate, $3H_2O$ and 34 g of NaOH in 1.0 liter of solution. A few drops of toluene are added as preservative.

2. Assay buffer: The stock buffer solution is diluted tenfold with $H_2O$.

3. Chloramine-T reagent. 1.41 g of chloramine-T is dissolved in 20.7 ml of $H_2O$ and mixed with 26 ml of n-propanol and 53.3 ml of stock buffer. (This reagent is stable at 4° C. for 2 weeks)

4. Dimethylaminobenzaldehyde reagent. 15 g of p-dimethylaminobenzaldehyde is suspended in 60 ml of n-propanol and 26 ml of perchloric acid (60%) is added slowly (N.B. Use a fume hood with protective goggles.) This reagent must be freshly prepared.

Differentiation of Integrin Alpha10 Positive Cells

Articular cartilage has little or no capacity for self repair. The reason for this low repair potential is unknown, but the lack of blood supply, low cell mobility due to the surrounding matrix and limited number of progenitor cells could be contributing factors. Tissue engineering approaches for cartilage have so far focused upon the use of stem cells with a chondrogenic differentiation capacity such as mesenchymal stem cells that can be used in vivo to repair or generate new cartilage (Jorgensen et al (2001) Ann Rheum Dis. 60(4):305-309; Johnstone and Yoo (2001) Expert Opin Biol Ther. 2001 1(6): 915-21). Whilst it is well documented that MSCs have the inherent potential to differentiate into osteogenic, chondrogenic, adipogenic and myocardiac cell lineages, there is currently no means of identifying the progenitor cell that will lead to these different lineages. Markers exist to indicate whether the cell is capable of expressing a cartilage phenotype i.e. collagen II and aggrecan, but these proteins are expressed extracellularly after synthesis, and cannot be used for isolation of a chondrogenic cell type.

After identification of an alpha10 positive cell population by any of the above methods, it would be highly desirable to be able to differentiate these cells to a chondrogenic phenotype and be able to distinguish between the other known phenotypes (Yoo et al (1998) J. Bone J. Surgery Am 80:1745-1757).

The following methods, known to the skilled man in the art, (Tallheden et al J. Bone. J. Surgery 85A (Suppl2):93-100) can therefore be used to determine if the alpha10 positive cells identified using the mAb365 antibody can be differentiated to a chondrocytes phenotype. Other differentiation conditions may be used as a control.

Chondrogenic Differentiation

The cells are cultured as pellet mass in DMEM (Gibco-BRL, Paisley, UK), insulin transferrin sodium selenite (Sigma, Sweden), 0.1 µM dexamethasone (Sigma, Sweden), 80 µM ascorbic acid-2-phosphate (Sigma, Sweden), 1 mg/ml linoleic acid-bovine serum albumin (Sigma, Sweden), 100 U/ml Penicillin, 100 µg/ml Streptomycin (GibcoBRL, Paisley, UK) and 10 ng/ml TGF-β3 (R&D Systems Europe Ltd., United Kingdom). To determine the chondrogenic differentiation the pellet cultures are tested for collagen type I and II, aggrecan and versican expression using Q-PCR.

Osteogenic Differentiation

To induce osteogenic differentiation the cells are cultured in DMEM-LG (GibcoBRL, Paisley, UK), 10% FCS (Sigma, St. Louis, Mo.), 50 µM ascorbic acid-2-phosphate (Sigma, Sweden), 0.10 µM dexamethasone (Sigma, Sweden), 100 U/ml Penicillin and 100 µg/ml Streptomycin (GibcoBRL, Paisley, UK). At day 11, 2 mM beta-glycerophosphate (Sigma, Sweden) is added to the culture. The control cells are cultured without dexamethasone and beta-glycerophosphate. The medium is changed every fourth day, during the 21 or 28 days of culture. The mineralization potential of the osteogenic differentiated cells are visualised by Von Kossa staining Adipogenic Differentiation To induce adipogenic differentiation the cells are cultured in DMEM-LG (GibcoBRL, Paisley, UK), 10% FCS (Sigma, St. Louis, Mo.), 1 µM dexamethasone (Sigma, Sweden), 60 µM indomethacin (Sigma, Sweden), 0.5 mM 3-isobutyl-methyl-xanthine (Sigma, Sweden), 5 µg/ml insulin (Sigma, Sweden), 100 U/ml Penicillin and 100 µg/ml Streptomycin (Gibco, Invitrogen). Every fourth day the cells are cultured during one day in DMEM-LG, 10% FCS (Sigma, St. Louis, Mo.), 100 U/ml Penicillin, 100 µg/ml Streptomycin (GibcoBRL, Paisley, UK) and 5 µg/ml insulin (Sigma, Sweden). The negative control cells are cultured in DMEM-LG (GibcoBRL, Paisley, UK) 10% FCS, 100 U/ml Penicillin and 100 µg/ml streptomycin (GibcoBRL, Paisley, UK). The cells are cultured for 14 days in differentiation media, the differentiated cells contain lipid vacuoles that can visualised with Oil Red 0 staining.

A Method for Isolating a Sub-Population of Mammalian ES Cells

According to the invention a method for isolating a sub-population of mammalian ES cells is disclosed. The method comprises the steps of
 a) providing a cell suspension comprising ES cells,
 b) contacting the cell suspension in a) with a monoclonal antibody or a fragment thereof according to the invention, binding to the extracellular I-domain of integrin alpha10beta1, under conditions wherein said monoclonal antibody or a fragment thereof forms an antibody-antigen complex with the extracellular I-domain of integrin alpha10beta1,
 c) separating cells binding to the monoclonal antibody or a fragment thereof in b), and optionally
 d) recovering cells binding to the monoclonal antibody or a fragment thereof in c) from said antibody or a fragment thereof,
thereby producing a sub-population of mammalian ES cells, optionally free from said antibody or a fragment thereof.

The cell suspension provided in a) above, comprising mammalian ES cells may be isolated from the inner cell mass (ICM) of the blastocyst of a 4-6 day old human embryo. Further ways of preparing ES cells are described by Talts et al. (1999)

In one further embodiment, the monoclonal antibody or fragment thereof is the antibody 365.

In one further embodiment, the mammalian ES cells are human ES cells.

In one further embodiment, the mammalian ES cells are murine ES cells.

In one embodiment, the method for isolating a sub-population of mammalian ES cells further comprises the steps of derivation and propagation of ES cells.

Derivation and propagation of ES cells may be performed by the procedure described below. Additional information can be found in Fong C. Y., and Bongso A. (1999), Fong C. Y., et al., (1997), and in Solter, D. and Knowles, B. (1975) all incorporated herein by reference.

In brief, fertilised oocytes are cultured to the blastocyst stage (day 6 after insemination), in sequential media, according to a standard co-culture free protocol (Fong and Bongso 1999). The zona pellucida is digested by e.g. pronase (Sigma, St. Louis, Mo.) (Fong et al 1997). The inner cell mass (ICM) is isolated by e.g. immunosurgery using anti-human serum antibody (Sigma) followed by lysis with complement (Life Technologies, Gaithersburg, Md.) (Solter, D and Knowles, B 1975).

The ICM may then be cultured on a mitomycin C mitotically inactivated mouse embryonic fibroblast feeder layer (75,000 cells/cm2) in gelatine-coated tissue culture dishes. The culture medium may consist of DMEM (Gibco, without sodium pyruvate, glucose 4500 mg/L) supplemented with 20% foetal bovine serum (Hyclone, Logan, Utah), 0.1 mM beta-mercaptoethanol, 1% non-essential amino acids, 2 mM glutamine, 50 U/ml penicillin and 50 pg/ml streptomycin (Life Technologies). During the isolation and early stages of ES cell cultivation, the medium may be supplemented with human recombinant leukaemia inhibitory factor hL1F at 2000 U/ml (Amrad, Melbourne, Australia).

After 6-8 days initial plating, ICM-like clumps may be removed mechanically by a micropipette from differentiated cell outgrowths and replated on fresh feeder layer. The resulting colonies may be further propagated in clumps of about 100 stem cell-like cells on a mouse feeder layer approximately every 7 days. The clumps are either dissociated mechanically, or with a combined approach of 5 mechanical slicing followed by exposure to dispase (10 mg/ml, Life Technologies).

The isolated clumps may be replated on a fresh human/mouse fibroblast feeder layer.

In the absence of feeder cells, a colony with the typical morphology of primate pluripotent stem cells may be developed after 2 weeks in culture.

A Monoclonal Antibody Binding to the Extracellular Part of the I-Domain of Integrin Alpha10Beta1 or a Fragment for Positive Selection of MSCs, ES Cells or Chondrocytes According to the invention, a monoclonal antibody or fragments thereof disclosed is used to identify the extracellular I-domain of the integrin alpha10 chain in the molecule comprising alpha10beta1.

In one embodiment, the antibody or fragment thereof is the monoclonal antibody 365 produced by a cell line named mAb 365 deposited at the Deutche Sammlung von Microorganismen and Zellkulturen under the accession number DSM ACC2583. A monoclonal antibody or fragments thereof according to the invention has a number of advantages over a polyclonal antibody. Monoclonal antibodies are available in an unlimited supply and high-affinity monoclonal antibodies can bind to a large proportion of the available antigen. Because all the antibodies are identical and bind to the same epitope, all of the antigen interactions can be broken under similar conditions. Polyclonal antibodies usually bind to numerous sites on an antigen and therefore bind with high avidity. If a polyclonal antibody or fragments thereof is coupled to a column for use in a separation procedure, the high avidity means that the antigen can be difficult to elute. The harsh conditions required to elute the antigen may damage the column or at least partially denature the antigen. Use of the monoclonal antibody or fragments thereof according to the invention, such as the antibody 365, therefore circumvents these problems.

The positive selection, e.g. a purification, may be achieved by conjugation of the monoclonal antibody according to the invention or fragments thereof to a suitable solid-phase matrix such as Protein A or Protein G, or by coupling to beads, such as magnetic beads or agarose beads. Conjugation means for separation are known to the skilled artisan. Protocols are described in e.g. Harlow and Lane 1999, incorporated herein by reference.

Furthermore the monoclonal antibody the antibody 365 or a fragment thereof may be coupled to magnetic beads in suspension; biotinylated with biotin and coupled to an avidin or streptavidin and/or coupled to a suitable support; or labelled with a fluorescent marker for use in a fluorescent activated cell sorter (FACS) to allow for ease of separation of the cell type in question. Any technique may be employed which is not unduly detrimental to the viability of MSCs, ES cells or chondrocytes.

In one embodiment separation is for mammalian MSCs. The separation, including identification and selection, may be performed by fluorescent cell sorting, by using e.g. a fluorescence activated cell sorter (FACS®) or any other methodology having high specificity. Multi-colour analyses may be employed with the FACS, which is particularly convenient. MSCs may be separated on the basis of the level of staining for the particular antigens. In a first separation, antibodies for other markers may be used labelled with one fluorochrome, while the antibody or a fragment thereof according to the invention may be conjugated to different fluorochrome(s). Other markers to be used may in further embodiments be SH-2, SH-3, CD29, CD44, CD71, CD90, CD106, CD120a, CD124, CD105, and Stro-1 that MSCs may express. Markers that are not expressed on MSCs are CD14, CD34 and CD45 and their expression, or lack of, may in further embodiments also be evaluated together with the antibody according to the invention or a fragment thereof binding to the I-domain of integrin alpha10beta1.

If further lineages or cell populations not being MSCs are to be removed in one step, various antibodies to such lineage-specific markers may be included. Fluorochromes, which may find use in a multi-colour analysis, include phycobiliproteins, e.g., phycoerythrin and allophycocyanins, fluorescein, Texas red, etc. well known to the skilled man in the art.

The MSCs may be selected against dead cells, by employing dyes associated with dead cells (propidium iodide, LDS). The cells may be collected in a medium comprising foetal calf serum.

MSCs may as well be selected based on light-scatter properties and their expression of various cell surface antigens, in combination with the identification using the antibody according to the invention or a fragment thereof.

In one embodiment separation is for mammalian chondrocytes.

The separation, including identification and selection, is performed by fluorescent cell sorting, by using e.g. a fluorescence activated cell sorter (FACS®) or any other methodology having high specificity. Multi-colour analyses may be employed with the FACS. Chondrocytes may be separated on the basis of the level of staining for alpha10beta1 expression. In a first separation, antibodies for other markers expressed on non-chondrogenic cells may be used as a negative selection step for chondrocytes. The antibody or a fragment thereof according to the invention may be conjugated to different fluorochrome(s) to be used in a positive selection step.

If further lineages or cell populations not being chondrocytes are to be removed in one step, various antibodies to such lineage specific markers may be included. Fluorochromes, which may find use in a multi-colour analysis, include phycobiliproteins, e.g., phycoerythrin and allophycocyanins, fluorescein, Texas red, etc. well known to a person skilled in the art.

The chondrocytes may be selected against dead cells, by employing dyes associated with dead cells (propidium iodide, LDS) or other non-chondrocytic cells, such as dedifferentiated cells. The chondrocytes may be collected in a medium comprising foetal calf serum.

In one embodiment separation is for a sub-population of mammalian ES cells expressing alpha10beta1.

The separation of such ES cells, including identification and selection, may be performed by fluorescent cell sorting, by using e.g. a fluorescence activated cell sorter (FACS®) or any other methodology having high specificity. Multi-colour analyses may be employed with the FACS. human ES cell markers include Stage-specific Embryonic Antigen-3 (SSEA-3), SSEA-4, GCTM-2, alkaline phosphatase, TRA-1-60, TRA-1-81 (reference Pera et al (2000); www.nih.gov/news/stemcell/scireport.htm)

Other techniques for positive or negative selection of MSCs, ES cells and chondrocytes may be employed. The techniques used should permit accurate separation, such as affinity columns, magnetic beads, or other types of beads readily conjugated with an antibody binding to the I-domain such as the antibody according to the invention, or similar types of techniques.

While it is believed that the particular order of separation is not critical to this invention, the order indicated in the embodiment below is one particular embodiment.

One embodiment for positive selection of MSCs, ES cells or chondrocytes includes that the cells in a provided cell suspension are initially separated by a crude separation, such as a centrifugation, a negative selection, or both, followed by a fine separation. The fine separation is a positive selection, using a monoclonal antibody or fragment thereof according to the invention, such as the antibody 365 or a fragment thereof, binding to the I-domain of integrin alpha10beta1 on MSCs, ES cells or chondrocytes. Further, a negative selection for markers associated with cells committed to other lineages, and other stem cell populations not being MSCs, ES cells or chondrocytes may be included.

The isolated cell population(s) is/are further described below.

In one embodiment, the monoclonal antibody or a fragment thereof according to the invention, such as the antibody 365 or a fragment thereof, used in the positive selection is linked to a solid phase. Examples of solid phases to be used are Protein A or Protein G, activated beads such as agarose beads, cross-linked agarose beads, polyacrylamide beads, copolymers of polyacrylamide and agarose beads or polyacrylic beads.

In one embodiment the solid phase is a bead. Examples of beads are beads comprising Protein A or Protein G, activated beads such as agarose beads, cross-linked agarose beads, polyacrylamide beads, copolymers of polyacrylamide and agarose beads or polyacrylic beads. Beads are activated with, for example Carbonyldiimadazole, Cyanogen bromide and by other similar methods well known to a skilled man in the art and further exemplified by Harlow and Lane, 1988, included herein by reference.

In one embodiment the solid phase is a bead such as magnetic bead. Cells can then be sorted using magnetic cell sorting, such as the MACS® system.

In still a further embodiment, the selected and isolated mammalian mesenchymal stem cells, ES cells or chondrocytes are human cells.

In still a further embodiment, the selected and isolated mammalian mesenchymal stem cells, ES cells or chondrocytes are murine cells.

Optionally, cells binding to the monoclonal antibody or a fragment thereof according to the invention, e.g. the antibody 365 or a fragment thereof, may be recovered. By "recovering" it is herein intended to mean that the selected cells are released from the monoclonal antibody or a fragment thereof to which they are bound, thereby producing a population of cells, e.g. MSCs, ES cells or chondrocytes, free from said antibody or a fragment thereof.

Thus, a monoclonal antibody binding to the extracellular part of the I-domain of integrin alpha10beta1 or a fragment thereof, such as e.g. the antibody 365 or a fragment thereof, will be highly valuable for further evaluation and enrichment of the chondrocytes, ES cells or MSC population.

Other Markers on MSCs

In further embodiments of the invention, the identification of MSCs may be combined with other markers known to be expressed by MSCs. Such other markers are SH-2, SH-3, CD29, CD44, CD71, CD90, CD106, CD120a, CD124, CD105, and Stro-1 that MSCs may express. Markers that are not expressed on MSCs are CD14, CD34 and CD45 and their expression may in further embodiments also be evaluated together with the binding of the antibody according to the invention or a fragment thereof.

Other Markers of Cartilage

As of today, no other cell surface markers for chondrocytes exist, aside from the integrin alpha10beta1. Antibodies according to the invention, reactive to the I-domain of alpha10, e.g. the antibody 365 disclosed in the present invention, are thus unique. Markers on cartilage matrix may still be used in combination with an antibody according to the invention. Examples of markers of cartilage matrix are aggrecan, collagen type II and the markers disclosed in US2003/0039966 by Hering and Johnstone incorporated herein by reference.

Other Markers on ES Cells

In further embodiments of the invention, the identification of human ES cells may be combined with other markers known to be expressed by human ES cells. Such other markers on human ES cells include Stage-specific Embryonic Antigen-3 (SSEA-3), SSEA-4, GCTM-2, alkaline phosphatase, TRA-1-60, TRA-1-81 (reference Pera et al (2000); www.nih.gov/news/stemcell/scireport.htm).

A Population of Mammalian Mesenchymal Stem Cells

A population of mammalian mesenchymal stem cells are obtainable by the method according to the invention. The population is characterised by mesenchymal stem cells that binds to a monoclonal antibody binding to the extracellular part of the I-domain of integrin alpha10beta1 or a fragment thereof, such as e.g. the antibody 365 or a fragment thereof.

In one embodiment, the mammalian stem cells are human mesenchymal stem cells.

In one further embodiment, the mammalian stem cells are murine mesenchymal stem cells.

In order to obtain human mesenchymal stem cells, it is necessary to isolate rare pluripotential mesenchymal stem cells, e.g. only one MSCs per 100 000 nucleated cells—see Bruder et al 1997 incorporated herein by reference—from other cells in the bone marrow or other MSCs sources, such as ES cells. Mammalian MSCs may be isolated from bone marrow, peripheral blood, cord blood, liver, bone, cartilage, muscle, perichondrium, periosteum, fat or any tissue comprising MSCs. The cell suspension may further be isolated from mammalian iliac crest, femora, tibiae, spine, rib or other medullary spaces. Other sources of human MSCs include embryonic yolk sac, placenta, umbilical cord, foetal and adolescent skin.

Said mesenchymal stem cells are the formative pluripotential blast cells that are capable of differentiating into any of the specific types of mesenchymal or connective tissues, i.e. the tissues of the body that support specialised elements; particularly bone, cartilage, muscle, tendon, ligament, marrow stroma, fat.

Use of an Isolated MSCs Population

A population of MSCs specifically isolated using a monoclonal antibody binding to the extracellular part of the I-domain of integrin alpha10beta1 or a fragment thereof, such as e.g. the antibody 365 or a fragment thereof, can be used for tissue repair and regeneration of cartilage, but also for the repair of bone, muscle, tendon, and ligament, either alone or immobilized to a biomaterial scaffold which acts as a support a guidance template.

Types of scaffold include, bioresorbable poly(α-hydroxy esters) scaffolds such as polylactic acid (PLLA), polyglycolic acid (PGA) and copolymer (PLGA).

Further embodiments include scaffolds derived from polymeric gels such as hyaluronic acid, collagen, alginate and chitosan.

Further embodiments include scaffolds derived from porous carriers, such as tricalcium phosphate and/or hydroxyapatite ceramic block (Luyten et al 2001)

Various procedures for transferring and immobilising the MSCs including injecting the isolated cells into the site of skeletal defect, incubating isolated cells optionally with the antibody 365 to hold the cells in place in suitable gel and implanting, incubating with bioresorbable scaffold etc. Thus, one embodiment is the conjugation of the antibody 365 to a bioresorbable scaffold allowing immobilisation of the cells before implantation into the damaged or defect site, e.g. into the site of a skeletal defect. The scaffold allows 3D immobilization of MSCs. Suitable biomaterial scaffolds are exemplified above. The examples given are not limiting the use of other suitable scaffolds obvious to a skilled artisan to choose if more suitable for the particular application.

MSCs isolated with monoclonal antibodies according to the invention or fragments thereof, such as the antibody 365, may also be directly injected back into the damaged site of the skeletal defect.

In still a further embodiment, injected cells are after injection captured and immobilized in a biomaterial scaffold conjugated to a monoclonal antibody according to the invention and further placed into the damaged area. The cells are thus captured and held in place at a correct position in a damaged site.

A Population of Mammalian Chondrocytes

The expression of alpha10beta1 on the cell surface of chondrocytes provides a useful tool for the identification and isolation of chondrocytes. Thus, the monoclonal antibody according to the invention or a fragment thereof is of great value in identifying chondrocytes or other cells expressing the integrin alpha10beta1 on their surface for treatment purposes in particular for the isolation of chondrocytes and chondrogenic cells e.g. synovial cells from the synovial lining of a patient (Nishimura et al 1999) for tissue engineering.

In one embodiment, the monoclonal antibody or fragment thereof is the antibody 365 or a fragment thereof.

Using a monoclonal antibody binding to the extracellular part of the I-domain of integrin alpha10beta1 or a fragment thereof, such as e.g. the antibody 365 or a fragment thereof for isolation of chondrocytes one may use autologous cells in procedures whereby diseased or damaged cartilage is to be repaired.

Mature articular cartilage has a poor reparative response to injury and its irreparable breakdown is a common feature of degenerative joint diseases, such as e.g. arthritis including osteoarthritis and rheumatoid arthritis. Repair of such injuries has focused upon different tissue engineering strategies, including the use of cell transplantation using autologous chondrocyte. Critical to these techniques is the identification and/or isolation of chondrocytes producing a hyaline cartilage.

Thus, antibodies according to the invention may be used for isolation of chondrocytes as well as identification of a cell with a chondrocyte phenotype i.e. chondrocytes producing a hyaline cartilage, and thus the antibody or fragment thereof can be used as a quality control, before in vivo implantation, to guarantee that only hyaline cartilage-producing cells are replaced into the diseased or damaged area.

Uses of Isolated Chondrocytes

Specifically, a monoclonal antibody binding to the extracellular part of the I-domain of integrin alpha10beta1 or a fragment thereof, such as e.g. the antibody 365 or a fragment thereof may be used to identify and isolate cells with a chondrogenic cell phenotype, particularly chondrocytes. Such a population of cells specifically isolated using the antibody 365 or fragments thereof may be used for autologous tissue repair and regeneration of cartilage either alone or in combination with any tissue scaffolds, such as a biomaterial scaffold, as a support.

Scaffolds to be used are mentioned in the paragraphs above.

A method for autologous tissue repair using chondrocytes isolated with a monoclonal antibody binding to the extracellular part of the I-domain of integrin alpha10beta1 or a fragment thereof, such as e.g. 365 or a fragment thereof, for autologous chondrocyte transplantation is disclosed. Further methods are described by Brittberg et al. incorporated herein by reference. Further embodiments of the method comprises the steps of
a) harvesting a biopsy comprising cartilage of healthy cartilage from a human subject, e.g. a patient, whilst undergoing an arthroscopic procedure,
b) enzymatically digesting the cartilage firstly with enzymes, such as pronase or hyaluronidase, and subsequently with collagenases to extract a cell population comprising chondrocytes,
c) culturing the cell population comprising chondrocytes in a suitable medium, for example, DMEM, F12 etc for 2-4 weeks,
d) purifying the chondrocytes from the cell population after culturing for about 2-4 weeks using an antibody according to the invention or a fragment thereof, either by FACS, mechanical purification such as beads, e.g. magnetic beads, or by use of a kit further described below,
e) performing surgery of a human patient to expose the damaged cartilage and at the same time remove periosteum from the medial tibia of the same human patient. Suture the periosteal flap over the injured or damaged cartilage area,
f) implanting the chondrocytes purified with the antibody or a fragment thereof, into the joint of the same human patient. Purified chondrocytes are injected under the periosteal flap, or in an alternative approach,
g) implanting the chondrocytes in combination with a biomaterial support (examples given previously) in which the monoclonal antibody or fragment thereof, is coupled/conjugated in order to immobilize the cells.

A Population of Embryonic Stem Cells

A population of mammalian embryonic stem (ES) cells are obtainable by the method according to the invention. The population is characterised by differentiated ES cells that bind to a monoclonal antibody binding to the extracellular part of the I-domain of integrin alpha10beta1 or a fragment thereof, such as e.g. the antibody 365 or a fragment thereof.

In one embodiment, the ES cells are human ES cells.

In one further embodiment, the mammalian stem cells are murine ES cells. Human ES cells may be derived from the inner cell mass (ICM) of the blastocyst of a 4-6 day old human embryo and may further be cultured in vitro on e.g. mouse embryonic fibroblast feeder cells to allow the cells to proliferate. Removal of growth factors or fibroblast growth factor-2 (FGF-2) from the medium causes the cells to differentiate at which point the population of cells expressing the integrin alpha10beta1 can be identified by using the antibody 365.

Uses of ES Cells

Specifically, a monoclonal antibody binding to the extracellular part of the I-domain of integrin alpha10beta1 or a fragment thereof, such as e.g. the antibody 365 or a fragment thereof may be used to identify and isolate differentiated ES cells. Such a population of cells specifically isolated using the antibody 365 or fragments thereof may be used for autologous tissue repair and regeneration of mesenchymally-derived tissues e.g. cartilage either alone or in combination with any tissue scaffolds, such as a biomaterial scaffold, as a support.

Scaffolds to be used are mentioned in the paragraphs above. ES cells isolated with monoclonal antibodies according to the invention or fragments thereof, such as the antibody 365, may also be directly injected back into the damaged site of the skeletal defect.

In still a further embodiment, injected cells are, after injection, captured and immobilized in a biomaterial scaffold conjugated to a monoclonal antibody according to the invention and further placed into the damaged area. The cells are thus captured and held in place at a correct position in a damaged site.

A Method for Identifying a Mammalian MSC

A method for identifying a MSC in a sample is disclosed. The method comprises the steps of
a) providing a sample cell suspension comprising of a mesenchymal stem cell,
b) contacting said sample cell suspension with a monoclonal antibody or a fragment thereof according to the invention binding to the extracellular domain of integrin alpha10beta1 produced by a cell line according to the invention,
c) incubating the sample cell suspension and the monoclonal antibody or a fragment thereof under conditions wherein said monoclonal antibody or a fragment thereof forms an antibody-antigen complex with the extracellular domain of integrin alpha10beta1 on a mesenchymal stem cell,
d) optionally adding a second labelled antibody or a fragment thereof to the sample, wherein the second antibody or a fragment thereof binds to the monoclonal antibody according to the invention or a fragment thereof in b)
e) detecting the monoclonal antibody or a fragment thereof bound to the extracellular domain of integrin alpha10beta1 of the sample b), or optionally detecting the second labelled antibody or a fragment thereof in c) bound to the monoclonal antibody or a fragment thereof.

Mammalian MSCs may be isolated from bone marrow, peripheral blood, cord blood, liver, bone, cartilage, muscle, perichondrium, periosteum, fat or any tissue comprising MSCs. The cell suspension may further be isolated from mammalian iliac crest, femora, tibiae, spine, rib or other medullary spaces. Other sources of human MSCs include embryonic yolk sac, placenta, umbilical cord, foetal and adolescent skin.

The sample cell suspension is provided from different mammals, such as a human being, a rodent, including all members of the phylogenetic *Rodentia*, such as a mouse, or a rat.

The contacting of said sample cell suspension with a monoclonal antibody according to the invention or a fragment thereof may be in any suitable cell culturing media, such as Dulbecco's Modified Eagle's Medium (DMEM), Hams F12 Nutrient Mixture, or in any physiological saline solution, preferably buffered, such as phosphate buffer saline (PBS), optionally with foetal calf serum (FCS) or bovine serum albumin (BSA) present.

The incubation of the cell suspension and the monoclonal antibody or a fragment thereof should be under conditions wherein said monoclonal antibody or a fragment thereof forms an antibody-antigen complex with the extracellular domain of integrin alpha10beta1 on a mesenchymal stem cell.

A second labelled antibody or a fragment thereof optionally added to the sample may be antibodies binding to molecules known to be expressed by MSCs. Such other molecules, or markers, are SH-2, SH-3, CD29, CD44, CD71, CD90, CD106, CD120a, CD124, CD105, and Stro-1 that MSCs may express. Markers that are not expressed on MSCs are CD14, CD34 and CD45 and their expression may in further embodiments also be evaluated in combination with the binding of the antibody according to the invention or a fragment thereof.

A Method for Identifying a Mammalian Chondrocyte

A method for identifying a chondrocyte in a sample is further disclosed. The method comprises the steps of
a) providing a sample cell suspension comprising of a chondrocyte,
b) contacting said sample cell suspension with monoclonal antibody according to the invention or a fragment thereof binding to the extracellular domain of integrin alpha10beta1 produced by a cell line according to the invention,
c) incubating the sample cell suspension and the monoclonal antibody or a fragment thereof under conditions wherein said monoclonal antibody or a fragment thereof forms an antibody-antigen complex with the extracellular domain of integrin alpha10beta1 on a chondrocyte,
d) optionally adding a second labelled antibody or a fragment thereof to the sample, wherein the second antibody or a fragment thereof binds to the monoclonal antibody according to the invention or a fragment thereof in b)
e) detecting the monoclonal antibody according to the invention or a fragment thereof bound to the extracellular domain of integrin alpha10beta1 of the sample b), or optionally detecting the second labelled antibody or a fragment thereof in c) bound to the monoclonal antibody or a fragment thereof.

The sample cell suspension may be isolated from cartilage.

The sample cell suspension is provided from different mammals, such as a human being, a rodent, including all members of the phylogenetic *Rodentia*, such as a mouse, or a rat.

The contacting of said sample cell suspension with a monoclonal antibody according to the invention or a fragment thereof may be in any suitable cell culturing media, such as Dulbecco's Modified Eagle's Medium (DMEM), Hams F12 Nutrient Mixture, or in any physiological saline solution, preferably buffered, such as phosphate buffer saline (PBS), optionally with foetal calf serum (FCS) or bovine serum albumin (BSA) present.

The incubation of the cell suspension and the monoclonal antibody or a fragment thereof should be under conditions wherein said monoclonal antibody or a fragment thereof forms an antibody-antigen complex with the extracellular domain of integrin alpha10beta1 on a chondrocyte A second labelled antibody or a fragment thereof optionally added to the sample may be antibodies binding to molecules known to be expressed by cartilage matrix antibody according to the invention as previously mentioned.

A Method for Identifying a Sub Population of Mammalian ES Cells

A method for identifying a sub-population of mammalian ES cells in a sample is disclosed. The method comprises the steps of
a) providing a sample cell suspension comprising of a differentiated ES cell,
b) contacting said sample cell suspension with a monoclonal antibody or a fragment thereof according to the invention binding to the extracellular domain of integrin alpha10beta1 produced by a cell line according to the invention,
c) incubating the sample cell suspension and the monoclonal antibody or a fragment thereof under conditions wherein said monoclonal antibody or a fragment thereof forms an antibody-antigen complex with the extracellular domain of integrin alpha10beta1 on a differentiated ES cell,
d) optionally adding a second labelled antibody or a fragment thereof to the sample, wherein the second antibody or a fragment thereof binds to the monoclonal antibody according to the invention or a fragment thereof in b)
e) detecting the monoclonal antibody or a fragment thereof bound to the extracellular domain of integrin alpha10beta1 of the sample b), or optionally detecting the second labelled antibody or a fragment thereof in c) bound to the monoclonal antibody or a fragment thereof.

The sample cell suspension may be isolated from the inner cell mass (ICM) of the blastocyst of a 4-6 day old human embryo.

The sample cell suspension is provided from different mammals, such as a human being, a rodent, including all members of the phylogenetic *Rodentia*, such as a mouse, or a rat.

The contacting of said sample cell suspension with a monoclonal antibody according to the invention or a fragment thereof may be in any suitable cell culturing media, such as Iscove's modified Dulbecco's medium (IMDM), or in any physiological saline solution, preferably buffered, such as phosphate buffer saline (PBS), optionally with foetal calf serum (FCS) or bovine serum albumin (BSA) present.

The incubation of the cell suspension and the monoclonal antibody or a fragment thereof should be under conditions wherein said monoclonal antibody or a fragment thereof forms an antibody-antigen complex with the extracellular domain of integrin alpha10beta1 on a differentiated ES cell.

A second labelled antibody or a fragment thereof optionally added to the sample may be antibodies binding to molecules known to be expressed by ES cells. Such other molecules, or markers, include Stage-specific Embryonic Antigen-3 (SSEA-3), SSEA-4, GCTM-2, alkaline phosphatase, TRA-1-60, TRA-1-81.

Markers that are not expressed on ES cells are CD14, CD34 and CD45 and their expression may in further embodiments also be evaluated in combination with the binding of the antibody according to the invention or a fragment thereof.

A Method for Detecting the Expression of Integrin Alpha10Beta1 in a Tissue Sample A method for detecting the expression of integrin alpha10beta1 in a tissue sample is disclosed. The method comprises the steps of
- a) providing a tissue sample,
- b) providing monoclonal antibody according to the invention or a fragment thereof binding to the extracellular domain of integrin alpha10beta1 produced by a cell line according to claim 1,
- c) incubating the tissue sample and the monoclonal antibody or a fragment thereof under conditions wherein said monoclonal antibody or a fragment thereof forms an antibody-antigen complex with the extracellular domain of integrin alpha10beta1,
- d) optionally adding a second labelled antibody or a fragment thereof to the sample, wherein the second antibody or a fragment thereof binds to the monoclonal antibody according to the invention or a fragment thereof in b),
- e) detecting the monoclonal antibody according to the invention or a fragment thereof bound to the extracellular domain of integrin alpha10beta1 of the sample b), or optionally detecting the second labelled antibody or a fragment thereof in c) bound to the monoclonal antibody or a fragment thereof.

A Method for In Vivo Imaging the Expression of Integrin Alpha10Beta1 in a Mammal A method for in vivo imaging the expression of integrin alpha10beta1 in a mammal is disclosed. By imaging the expression, distribution and quantification of alpha10beta1 can be determined The method comprises the steps of
- a) providing a mammal,
- b) providing a monoclonal antibody or a fragment thereof binding to the extracellular domain of integrin alpha10beta1 produced by a cell line according to claim 1,
- c) administering the monoclonal antibody or a fragment thereof to the mammal so as to allow the antibody or a fragment thereof to bind to the extracellular domain of integrin alpha10beta1 of cells in said mammal,
- d) optionally adding a second labelled antibody or a fragment thereof to the sample, wherein the second antibody or a fragment thereof binds to the monoclonal antibody or a fragment thereof in c),
- e) detecting the monoclonal antibody or a fragment thereof bound to the extracellular domain of integrin alpha10beta1 of said cells in c), or optionally detecting the second labelled antibody or a fragment thereof in d) bound to the monoclonal antibody or a fragment thereof, and
- f) creating an image of the detected antibody or a fragment thereof, thereby imaging the expression of integrin alpha10beta1 on cells in a mammal in vivo.

In one embodiment, said monoclonal antibody or a fragment thereof is labelled with a detectable moiety, such as a radio-opaque agent or radioisotope.

The monoclonal antibody or a fragment thereof in c) above must be administered so as to allow the antibody or a fragment thereof to bind to the extracellular domain of integrin alpha10beta1 of cells in said mammal. Administration may be performed by injection into the bloodstream, e.g. intravenous, into synovial fluid, intramuscular, intraperitoneal, intra-articular, subcutaneous, into the cavity surrounding the tendon or directly into a plaque formed in a blood vessel. The presence and location of a labelled antibody or a fragment thereof in a host is assayed by e.g. imaging.

Information obtained by imaging, using the method described above, is useful when studying the progression, regression or repair during a medical treatment of e.g. a joint disease, such as e.g. arthritis including osteoarthritis and rheumatoid arthritis. Other diseases are tendinitis, e.g. peritendinitis, tenosynovitis, insertitis, tendinous bursitis and apophysitis, and in atherosclerosis e.g. the detection of atherosclerotic plaque in blood vessels.

The antibody according to the invention, such as the antibody 365, or a fragment thereof may be labelled with any moiety or means that is detectable in a host. Suitable means for detection are any non-invasive methods in vivo, such as any imaging method. Examples of such methods are Magnetic Resonance Imaging (MRI), Ultrasound, such as intravascular ultrasound (IVUS), Computed tomography, such as Electron Beam Computed Tomography (EBCT) and multislice tomographic scanning, as well as angiography. Any other suitable means known to the skilled man in the art may also be used such as means described in Narayanan et al 2000, included herein by reference.

A Composition

According to the invention, a composition comprising a monoclonal antibody binding to the extracellular part of the I-domain of integrin alpha10beta1 or a fragment thereof, such as e.g. the antibody 365 or a fragment thereof produced by a hybridoma cell line according to the invention is disclosed.

In a further embodiment, the monoclonal antibody according to the invention or a fragment thereof is conjugated. Any known method in the art for separately conjugating the antibody or a fragment thereof to the detectable moiety may be employed including those methods described by David et al (1974), Pain et al (1981) and Nygren et al (1982).

For diagnostic applications, the monoclonal antibody according to the invention or a fragment thereof will typically be conjugated and labelled with a detectable moiety. The detectable moiety can be any one that is capable of producing, either directly or indirectly, a detectable signal.

In one embodiment, said monoclonal antibody or a fragment thereof is further conjugated and comprises a detectable label, such as a fluorescent or chemiluminescent compound, such as fluorochromes, e.g. fluorescein isothiocyanate, rhodamine, or luciferine, or any fluorochrome which may find use in a multi-colour analysis including phycobiliproteins, e.g., phycoerythrin and allophycocyanins, fluorescein, Texas red, etc. well known to a person skilled in the art. Fluorochromes can be used with a fluorescence activated cell sorter; or the like, to allow for ease of separation of the particular cell type.

In a further embodiment the monoclonal antibody or a fragment thereof can be conjugated, or labelled, with a suitable radioactive or enzymatic label by conventional methods and/or bound to suitable solid phases known to the skilled man in the art. Examples of enzymes are alkaline phosphatase, beta-galactosidase or horseradish peroxidase, a radioisotope, such as $^{3}$H, $^{14}$C, $^{32}$P, $^{35}$S, $^{125}$I or radioactive isotopic labels that are useful within the body of a human subject and include $^{111}$I, $^{99}$Tc, $^{67}$Ga, $^{186}$Re, and $^{132}$I.

In a further embodiment, said monoclonal antibody or a fragment thereof further comprises means for separation of a cell, which allows for direct or indirect separation e.g. biotin, binding to avidin; or streptavidin. The means for separation may be bound to a solid support such as beads, e.g. magnetic beads, agarose or other similar types of beads known to the skilled man in the art. Any means suitable for separation of cells may be employed on the condition that the separation is not unduly detrimental to the viability of a cell.

In a further embodiment the monoclonal antibody or a fragment thereof can be used in combination with, or coupled to, an immunochemical such as biotin and its analogues (e.g. iminobiotin), avidin and its analogues (streptavidin), alkaline phosphatases or other such markers for the identification and/or quantification of MSCs, ES cells or chondrocytes and the direct/indirect separation of said cells.

Medical Use

A use of a monoclonal antibody or a fragment thereof binding to the extracellular domain of integrin alpha10beta1 produced by a cell line according to the invention, such as the antibody 365, for the preparation of a pharmaceutical composition for the treatment of joint diseases, such as e.g. arthritis including osteoarthritis and rheumatoid arthritis in a mammal in the need thereof is disclosed. Other diseases are tendinitis, e.g. peritendinitis, tenosynovitis, insertitis, tendinous bursitis and apophysitis, and atherosclerosis.

In a further embodiment, an additional pharmaceutically acceptable drug affecting joint diseases, such as e.g. arthritis including osteoarthritis and rheumatoid arthritis is included to the pharmaceutical composition. Other diseases are tendinitis, e.g. peritendinitis, tenosynovitis, insertitis, tendinous bursitis and apophysitis, and atherosclerosis.

A monoclonal antibody binding to the extracellular part of the I-domain of integrin alpha10beta1 or a fragment thereof, such as e.g. the antibody 365 or a fragment thereof is characterized as having the ability to specifically immunoreact with the I-domain of the alpha subunit of the integrin alpha10beta1 and thereby inhibit the capacity of the integrin to specifically bind to its ligand by an interaction with a ligand-containing protein. Thus the antibody or fragment thereof is useful to inhibit and stimulate, and thereby modulate, either in vivo or in vitro, the functionality of the cells that contain integrin alpha10beta1 with which the antibody or a fragment thereof immunoreacts.

For treatment and therapeutic applications, the antibody or a fragment thereof is administered to a mammal, preferably human, in a pharmaceutically acceptable dosage form. The antibody or a fragment thereof may be administered intravenously as a bolus, or by continuous infusion over a period of time, by intramuscular, subcutaneous, intra-articular, intrasynovial, intrathecal, oral, topical or inhalation routes.

An administration vehicle comprising a monoclonal antibody or a fragment thereof in a dosage form binding to the extracellular domain of integrin alpha10beta1 produced by a cell line according to the invention, pharmaceutical acceptable carrier, and a pharmaceutical acceptable drug affecting joint diseases, such as e.g. arthritis including osteoarthritis and rheumatoid arthritis is disclosed. Other diseases are tendinitis, e.g. peritendinitis, tenosynovitis, insertitis, tendinous bursitis and apophysitis, and atherosclerosis.

The dosage forms encompass pharmaceutically acceptable carriers that are inherently non-toxic and non-therapeutic. Examples of such carriers include ion exchangers, alumina, aluminium stearate, lecithin, serum proteins such as human serum albumin, buffers such as phosphate or glycine, sorbic acid, potassium sorbate, partial glyceride mixtures of saturated vegetable fatty acids, water, salts, or electrolytes such as protamine sulphate, sodium chloride, metal salts, colloidal silica, magnesium trisilicate, polyvinyl pyrrolidone, cellulosic polymers and polyethylene Glycol. Carriers for topical or gel-based forms of antibody or a fragment thereof include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. Conventional depot forms include, for example, liposomes, microcapsules, nano-capsules, plasters, sublingual tablets, and polymer matrices such as poly(orthoesters), polylactide:polyglycolide polymers.

When the antibody or a fragment thereof is present in an aqueous dosage form, rather than being lyophilised, the antibody or a fragment thereof typically may be formulated at a concentration of about 0.1 mg/ml to 100 mg/ml, although a wide variation outside of these ranges is permitted.

For the prevention or treatment of disease, the appropriate dosage of the antibody 365 will depend on the type of disease to be treated, the severity and course of the disease, whether the antibody or a fragment thereof is administered for preventative or therapeutic purposes, the course of previous therapy and the patient's clinical history and response to the antibody or a fragment thereof. The antibody or a fragment thereof is suitably administered to the patient at one time or over a series of treatments.

Depending on the type and severity of the disease, about 0.015 to 15 mg of antibody or a fragment thereof/Kg of patient weight is an initial candidate dosage for administration to the patient. Administration may be, for example, by one or more separate administrations, or by continuous infusion. For repeated administrations over several days or longer, depending on the condition, the treatment is repeated until a desired suppression or alleviation of the disease symptoms occurs. However, other dosage regimens may be useful and are not excluded.

According to a further embodiment of the invention, the effectiveness of the monoclonal antibody or a fragment thereof in alleviating the symptoms, preventing or treating disease may be improved by administering an antibody or fragment thereof according to the invention serially or in combination with another agent that is effective for the same clinical objective, such as another antibody or a fragment thereof directed against a different epitope than that of the antibody according to the invention, or one or more conventional therapeutic agents known for the intended therapeutic indication, e.g. arthritis including osteoarthritis and rheumatoid arthritis. Other diseases are tendinitis, e.g. peritendinitis, tenosynovitis, insertitis, tendinous bursitis and apophysitis, and atherosclerosis.

Suitable pharmaceutically acceptable agents affecting such indications may be anti-inflammatory drugs such as non steroidal anti-inflammatory drugs (NSAIDS) for the treatment of joint diseases e.g. osteoarthritis, rheumatoid arthritis; anti-cytokine agents e.g. anti-TNF antibodies, interleukin receptor antagonist, matrix metalloproteinase (MMP) inhibitors or bone morphogenic proteins (BMP); local anaesthetics for use post-operatively following orthopaedic surgery for the treatment of pain management or hypolipidemic drugs for treatment of atherosclerotic plaque, matrix metalloproteinase (MMP's) inhibitors or bone morphogenic proteins (BMP's).

Combination of Possible Drugs with Ab for Delivery

In another embodiment of the invention, a monoclonal antibody binding to the extracellular part of the I-domain of integrin alpha10beta1 or a fragment thereof, such as e.g. the antibody 365 or a fragment thereof, or a pharmaceutical composition thereof, will be used as a vehicle to enable the targeted the delivery of other known therapeutic agents to alpha10beta1 expressing cells. Such cells include chondrocytes, MSCs, macrophages, monocytes, synovial cells, tenocytes, myoblasts, osteoblasts, and fibroblasts.

The expression of the exogenous genetic material in vivo, is often referred to as "gene therapy". Disease states and procedures for which such treatments have application include genetic disorders and diseases of joints. Cell delivery of the transformed cells may be effected using various methods and includes infusion and direct depot injection into joints, periosteal, bone marrow and subcutaneous sites.

In one embodiment, the pharmaceutical composition is administered as an administration vehicle, comprising said monoclonal antibody or a fragment thereof combination with other gene or bio delivery systems. The combined administration vehicle comprising said monoclonal antibody or a fragment thereof is used in combination with other gene or bio delivery systems to selectively target integrin alpha10beta1 expressing cells.

Such a vehicle would involve coupling the antibody or a fragment thereof to a delivery vehicle which would include, for example, virus, liposomes, microcapsules, nano-capsules, plasters, sublingual tablets, and polymer matrices such as poly(orthoesters), polylactide:polyglycolide polymers, and coupling the treatment agent either to the antibody or a fragment thereof, or to the delivery vehicle. Examples of agents that could be coupled are non-steroidal anti-inflammatory drugs (NSAIDS), local anaesthetics, cytokine antagonists such interleukins-1 receptor antagonist, type II soluble receptor of interleukins-1, anti-TNF-α monoclonal antibodies, soluble TNF-α receptor, anti-inflammatory cytokines such as IL-4, IL-10, IL-11, growth factors such as fibroblast growth factor, insulin growth factor, transforming growth factor-beta, hepatocyte growth factor, platelet-derived growth factor, parathyroid hormone-related peptide, bone morphogenic proteins, Indian hedgehog, sonic hedgehog, SOX proteins such as SOX5-6, and SOX9, BMP's such as BMP 2 and 7, or inhibitors of metalloproteinases.

In a further embodiment, the antibody or a fragment thereof will be used as a vehicle to enable targeted gene-delivery of agents to alpha10beta1 expressing cells. Cells to be targeted for gene-delivery include those cells of the skeletal system comprising, cartilage, bone, tendon, ligament and muscle, or cells in an atherosclerotic plaque.

One drawback of the currently available vectors for gene therapy is the lack of a specific cell surface target on cells such as chondrocytes, MSCs and ES cells in gene delivery. It is therefore of great advantage to be able to target the cell of interest e.g. a chondrocyte, by use of an antibody or a fragment thereof such as an antibody, or a fragment thereof, of the present invention, e.g. the antibody 365.

In one embodiment the antibody or a fragment thereof may be used in conjunction with a viral or non-viral delivery system for the in vivo delivery of a gene or a part thereof directly to the target tissue or cell of interest, e.g. alpha10 expressing cells of cartilage.

In another embodiment a gene is delivered into a alpha 10beta1 expressing cell, preferably MSCs or chondrocyte using a virus, viral vectors include retroviruses, adenoviruses, adeno-associated viruses (AAV), herpes simplex virus and lentivirus.

Especially genes may be transferred to chondrocytes via the integrin alpha10beta1 using adenovirus and the monoclonal antibodies according to the inventions, such as the mAb365 antibody. This may be done as described in Barry et al 2003 and Parrott et al 2003.

In one embodiment a gene or a combination of genes are delivered into a MSCs or chondrocyte by a non-viral method. Non-viral delivery systems include the use of naked DNA, cationic liposomes, cationic lipids and polymers as well as DNA/cationic liposome/polycation complexes.

Suitable Genes of Interest to be Delivered Examples of suitable genes to be delivered include growth factors such as insulin-like growth factor-1 (IGF-1), transforming growth factor-beta (TGF-β), fibroblast growth factors, and bone morphogenic proteins, transcription factors such as SOX-9, SOX-5, SOX-6, certain signalling molecules such as SMADs and molecules that inhibit apoptosis such as BCL-2, enzyme inhibitors such as metalloproteinase inhibitors, promoters for genes of extracellular matrix molecules such as collagens e.g. collagen type II.

Methods are applicable to rodents including mice, rats, rabbits, as well as humans.

In another embodiment cells expressing alpha10beta1 isolated using the antibody according to the invention or a fragment thereof, e.g. the antibody 365 or a fragment thereof, such as chondrocytes, are for use in autologous chondrocyte transplantation. The cells are then genetically modified while undergoing expansion in culture. Viral vectors such as retrovirus, adenovirus, AAV, and lentivirus can readily transduce these cells. The antibody according to the invention or a fragment thereof in conjunction with a viral delivery system may be used to target chondrocytic cells expressing alpha10beta1.

In yet another embodiment mesenchymal stem cells isolated with the monoclonal antibody according to the invention or a fragment thereof, for use in tissue repair are genetically modified using viral vectors such as retrovirus, adenovirus, AAV, and lentivirus and other viral vectors known to the skilled man in the art. Antibody 365 in conjunction with a viral delivery system can used to target MSCs expressing alpha10beta1.

In one embodiment the antibody or a fragment thereof may be used in conjunction with a viral or non-viral delivery system for the in vivo transfer of a gene(s) directly to the damaged tissue, e.g. of cartilage, tendon, bone, ligament, muscle etc. The antibody 365 or a fragment thereof and the gene(s) of interest may be delivered locally to the site of tissue damage.

In another embodiment the chondrocytes isolated with an antibody according to the invention or a fragment thereof for use in autologous chondrocyte transplantation are genetically modified while undergoing expansion in culture, i.e. ex vivo gene transfer. An antibody or a fragment thereof is then used in conjunction with a viral/non-viral delivery system and can used to target those cells that have not de-differentiated and thus lost their chondrocytic phenotype. These cells are then injected intraarticularly back into the joint of the patient from which they were harvested.

In still another embodiment, MSCs with an antibody according to the invention or a fragment thereof coupled to a gene of interest or modified using viral/non-viral vectors can be transplanted together with a suitable tissue scaffold or matrix. Suitable tissue scaffolds are described above.

In yet another embodiment, MSCs with an antibody according to the invention or a fragment thereof coupled to the gene of interest can be transplanted directly into the damaged tissue, e.g. damaged tissues including those mentioned previously.

In yet another embodiment, MSCs with an antibody according to the invention or a fragment thereof coupled to the gene of interest can be transplanted together with a suitable tissue scaffold or matrix. Suitable scaffolds are mentioned above.

In still another embodiment, non-viral methods using an antibody according to the invention or a fragment thereof for gene transfer are used. Such methods may be based on e.g. cationic lipids, or polyplex conjugates.

Various types of synthetic vectors have been developed for gene transfer, such as cationic-lipid, and polymer-based systems. Cationic-lipid/DNA complexes, i.e. lipoplexes, may be used in which an antibody according to the invention or a fragment thereof may be complexed with the liposome containing the DNA of the gene of interest. Such genes are as mentioned previously, and include e.g. growth factors.

In one embodiment an antibody according to the invention or a fragment thereof is incorporated into liposomes together with DNA of a gene of interest and injected locally into a joint in the form of polyplex, or molecular, conjugates.

Mammals in the Need Thereof

According to the invention, a mammal in the need thereof may be a human being in the need thereof. Examples of a human being in the need thereof is a human being with a bone or joint disease, e.g. arthritis including osteoarthritis and rheumatoid arthritis, osteoporosis or rachitis. Other diseases are tendinitis, e.g. peritendinitis, tenosynovitis, insertitis, tendinous bursitis and apophysitis and atherosclerosis.

Further, a mammal in the need thereof may be a any mammal such as a horse, a cow, a pig or piglet, dog, or primate.

Further, a mammal in the need thereof may be a rodent, including all members of the phylogenetic *Rodentia*, such as a rabbit, a mouse, guinea pig, or a rat.

Routes for Administration

The antibody or fragments thereof of the present invention can be administered to an individual by an appropriate route, either alone or in combination with—before, simultaneously with, or after—another drug or agent. For example, the antibody of the present invention can also be used in combination with other monoclonal or polyclonal antibodies, with existing products, such as commercially available products used in prophylactic or therapeutic treatments of joint diseases. The antibody or fragments of the present invention can be used as separately administered compositions given in conjunction with antibiotics and/or antimicrobial agents.

An effective amount of an antibody or fragments thereof is administered. An effective amount is an amount sufficient to achieve the desired therapeutic effect, including prophylactic, under the conditions of administration, such as an amount sufficient for inhibition or stimulation of alpha10beta1, and thereby, modulate, such as prevent, alleviate, or treat, a joint disease.

A variety of routes of administration are possible including, but not necessarily limited to, oral, dietary, topical, parenteral, e.g., intravenous, intraarterial, intramuscular, subcutaneous, intra-articular, or intraperitoneal, depending on the joint disease or condition to be treated. Other suitable methods of administration can also include rechargeable or biodegradable devices and slow release polymeric devices. The pharmaceutical compositions of this invention can also be administered as part of a combinatorial therapy with other agents.

Kit According to the Invention

The invention further discloses a kit, comprising the monoclonal antibody an antibody according to the invention or a fragment thereof or a fragment thereof.

Kits for use in detecting the presence of a mammalian integrin alpha10beta1 in a biological sample can also be prepared. Such kits will include an antibody according to the invention or a fragment thereof, such as antibody 365 or fragment thereof which binds to an I-domain of a mammalian integrin alpha10beta1, as well as one or more ancillary reagents suitable for detecting the presence of a complex between the antibody or fragment and integrin alpha10beta1 or portion thereof. The antibody compositions of the present invention may be provided in lyophilized form, either alone or in combination with additional antibodies specific for other epitopes.

The antibodies, which may be labelled or unlabelled, may be included in the kits with adjunct ingredients e.g., buffers, such as Tris, phosphate and carbonate, stabilizers, excipients, biocides and/or inert proteins, e.g., bovine serum albumin. For example, the antibodies can be provided as a lyophilized mixture with the adjunct ingredients, or the adjunct ingredients can be separately provided for combination by the user. Generally these adjunct materials will be present in less than about 5% weight based on the amount of active antibody, and usually will be present in a total amount of at least about 0.001% weight based on antibody concentration.

Where a second antibody capable of binding to the monoclonal antibody is employed, such antibody can be provided in the kit, for instance in a separate vial or container. The second antibody, if present, is typically labelled, and may be formulated in an analogous manner with the antibody formulations described above.

The kit includes, in an amount sufficient for at least one isolation, an monoclonal antibody of the present invention or a fragment thereof as a separately packaged reagent, or in one further embodiment as a reagent in combination with a solid phase support or bead. Instructions for use of the packaged reagent are also typically included.

In one embodiment the present invention relates to a kit for isolating ES cells, MSCs or chondrocytes from a human subject.

In a further embodiment, the monoclonal antibody or a fragment thereof comprises a detectable label.

In one further embodiment the kit comprises an antibody according to the invention or a fragment thereof and an anti-immunoglobulin labelled antibody or a fragment thereof, for example PE-labelled goat anti-mouse IgG, suitable for use in FACS analysis.

In one further embodiment the kit comprises an antibody according to the invention or a fragment thereof coupled to solid phase support or bead. Examples of solid supports of beads are given in the paragraphs above.

In one further embodiment, an antibody according to the invention is provided in a solution.

In one further embodiment, an antibody according to the invention is provided lyophilized to be dissolved upon usage.

Further, a kit for production of an antibody according to the invention or a fragment thereof, such as the antibody 365 or a fragment thereof, is disclosed, comprising a hybridoma cell line, such as the hybridoma cell line mAb365 according to the invention.

In one embodiment the kit for production of an antibody according to the invention or a fragment thereof, such as the antibody 365 or a fragment thereof, a cell culture medium for said hybridoma cell line is included.

While the invention has been described in relation to certain embodiments the skilled person may foresee other not mentioned embodiments, variations or combinations, that are still within the scope of the claims.

By the expression "comprising" as used herein we understand including but not limited to the stated items.

The invention will now be described by the following non-limiting examples.

EXAMPLES

Example 1

Generation of Clone 365

Objective

The objective with this example was to generate a monoclonal antibody against the I-domain of the extracellular domain of alpha10.

Materials and Methods

The Antigen

For the production of a monoclonal antibody specific for alpha10 integrin, alpha10 knockout mice were immunized with recombinant alpha10 I-domain purified from an alpha10 I-domain-expressing cell line. The cell line was generated by transfecting HEK 293-EBNA cells with the expression vector pCEP4 coding for His-tagged alpha10 I-domain alone or fused to alkaline phosphatase (AP).

The recombinant proteins have been designed so that they were secreted into the culture medium from where they were affinity purified on NiNTA agarose (Qiagen). Purity was confirmed by electrophoresis.

Immunisation

Mice were immunized intramuscularly with 2-10 μg alpha10 I-domain-alkaline phosphatase fusion protein mixed with the mouse adjuvant Immuneasy (Qiagen). Fifteen days later the mice were boosted with the same antigen. A further 2 or 3 boosts with alpha10 I-domain (4 μg) administered subcutaneously at the base of tail at 2-week intervals, was required to reach the desired specificity response in both ELISA and FACS.

Two days after the last immunization, spleen cells from the mice were fused with NSO myeloma cells using polyethylene glycol. Fused cells were seeded in a 96-well microplate and grown in DMEM/F12 (Invitrogen) medium containing BM Condimed H1 (Roche) and HAT (hypoxanthine, aminopterin, thymidine mixture Sigma) selection.

Hybridoma cell clone supernatants were tested for anti-alpha10 antibody production by their ability to bind to immobilized alpha10 I-domain by ELISA and by binding to a cell line expressing alpha10beta1 in FACS analysis.

A total of 29 alpha10 I-domain positive clones were identified by ELISA, and one of them named the antibody 365 was found to bind specifically to alpha10beta1 by FACS. Positive hybridoma cell lines were subcloned three times by limiting dilution techniques.

Isotyping of the antibody secreted by clone 365 by Isostrip, a mouse monoclonal antibody isotyping kit by Roche (Switzerland), identified the antibody to be an IgG2aκ

Results

One hybridoma clone, 365, was stable after subcloning. The monoclonal antibody produced by the hybridoma is further characterised below.

Example 2

Immunoprecipitation of Integrin Alpha10Beta1 with the Antibody 365

Objective

The objective with this example was to demonstrate the specificity of the antibody 365 for the whole integrin (alpha10beta1) by immunoprecipitation (IP).

Materials and Methods

In the following experiment, polyclonal antibodies against the cytoplasmic domains of integrin subunits alpha10 and alpha11 were used as control antibodies. These polyclonal antibodies had previously been shown to specifically immunoprecipitate integrins alpha10beta1 and. alpha11beta1 respectively from cell lysates.

C2C 12 cells transfected with integrin subunit alpha10 or alpha11 (negative control) were grown in DMEM medium with 10% FCS. Cells adherent on the plate were washed once with PBS and then surface biotinylated using 0.5 mg/ml Sulfo-NHS-LC-biotin (Pierce) in 4 ml PBS for 20 min on ice. Cells were then washed once with PBS and 10 ml 0.1M glycine/PBS were added for 5 min on ice. After washing once with PBS cells were lysed in 1 ml lysis buffer (1% NP-40, 10% glycerol, 20 mM Tris/HCl, 150 mM NaCl, 1 mM $MgCl_2$, 1 mM $CaCl_2$, protease inhibitor cocktail Roche, pH7.5) on ice. The cell lysate was collected with a plastic scraper and spun down at 15.000 g for 10 min. The supernatant was removed and incubated with 1 μl of α10 pre-immune serum and then 20 μl Prot G Sepharose (Amersham) in 100 μl lysis buffer were added. After rotating 1 h at 4° C. the lysate was centrifuged for 1 min at 8000 rpm and the supernatant removed. For each immunoprecipitation 150 μl cell lysate supernatant were pipetted into an eppendorf tube and 1 μl of antiserum or monoclonal antibody solution was added. The antibodies used were mouse the antibody 365, rabbit-anti-human α10 serum and rabbit-anti-human α11 serum, respectively (both sera against the cytoplasmic domains of the integrins). After 2 h rotating at 4° C., 20 μl prot G Sepharose (Amersham) in 100 μl lysis buffer were added and the mixture further rotated for another 45 min. The Sepharose-beads were then spun down briefly and washed three times with lysis buffer. 20 μl SDS PAGE sample buffer (including 100 mM DTT) were added to the Sepharose beads and the samples were boiled for 5 min. 5 μl of each sample were run on an 8% straight gel (Novex) and then electro-transferred onto a PVDF membrane. The membrane was blocked in 2% BSA/TBST for 1 h, washed once with TBST and then incubated with 2 μl Extravidin-peroxidase (Sigma) in 8 ml blocking buffer. After 1 h the Extravidin-peroxidase solution was removed and the membrane washed 3×20 min in TBST. Surface biotinylated proteins were then detected with ECL (Amersham) and visualised on a photographic film.

Results

Figure 2:
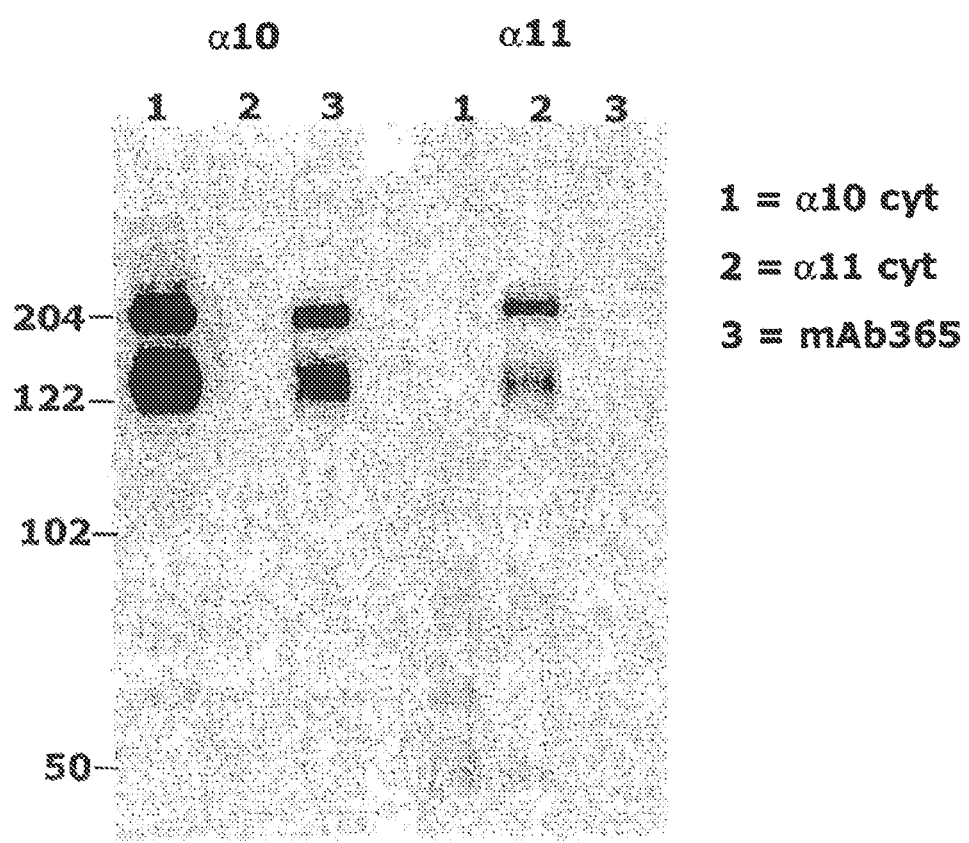

The results in FIG. 2 demonstrate that the antibody 365 is able to immunoprecipitate the whole integrin alpha10beta1 (lane 3); cytoplasmic polyclonal alpha10 antibody was used as a positive control to confirm the presence of integrin alpha10beta1 on the surface of the alpha10-transfected C2C12 cells (lane 1). The antibody 365 was specific for the alpha10beta1 integrin since it did not immunoprecipitate integrin alpha11beta1 from alpha11-transfected C2C12 cells (lane 6) or any other protein. Polyclonal serum against the cytoplasmic domain of integrin alpha11 subunit (lane 5) was used a positive control for alpha 11 transfected cells.

Example 3

ELISA

Objective

The objective with this example was to demonstrate the specificity of the antibody 365 for the I-domain of the integrin alpha10 chain by ELISA (enzyme linked immunosorbent assay).

Materials and Methods

Soluble recombinant I-domain (10 µg) of alpha10, alpha11, alpha1 or control protein (alkaline phosphatase) was coated in a 96 well ELISA plate (Maxisorp Nunc) overnight in PBS.

Hybridoma culture supernatant containing approximately 1 µg/ml of the antibody 365 was applied and specific binding of the antibody to alpha10 I domain was detected by horse-radish peroxidase-conjugated goat anti-mouse IgG and subsequently peroxidase substrate (OPD SigmaFast, Sigma). The absorbance of the colorimetric change was determined at 492 nm.

Results

Figure 3:
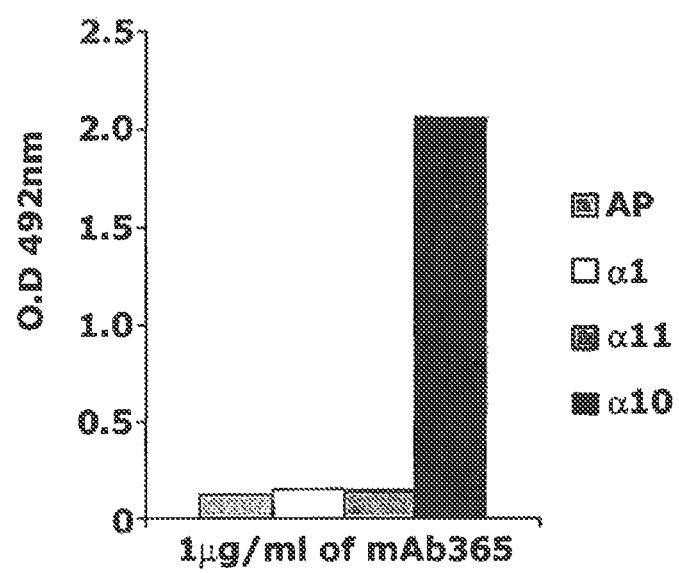

The results in FIG. 3 confirm that the antibody 365 specifically recognises the I-domain of the integrin subunit alpha10. No reactivity was observed with control (AP) or the I-domains of the integrin alpha1 and alpha11.

Example 4

Cell Adhesion Assay

Objective

The objective of example 4 is to show that the antibody 365 can modulate the binding of alpha10beta1 to collagen type II.

Materials and Methods 48-well plates (Nunc) were coated with collagen type II or BSA (10 µg/ml 150 µl/well) in PBS 4° C. overnight, followed by blocking with 2% BSA in PBS for 1 h at room temperature. Cells were trypsinized, washed and then seeded on collagen or BSA coated wells at specific ion-concentrations in the presence or absence of antibodies Cells were seeded at 50,000 cells/well, and were allowed to attach for 1 h 37° C. Wells were washed two times with PBS. Cell numbers of adherent cells were determined using the hexosaminidase test as follows:—Attached cells were lysed in 150 µl substrate solution (7.5 mM p-Nitrophenyl-N-Acetyl-β-D-Glucosamine, 0.05M sodium acetate pH 5, 0.25% Triton X-100). The plates were incubated at 37° C. for 2.5 h. 60 µl of the cell lysate were transferred to a microtiter plate (Nunc) and mixed with 90 µl developing buffer (5 mM EDTA, 50 mM Glycine pH 10.4)

The absorbance at 405 nm was read and used as a measure of cell number. For each cell line used, a cell number standard was made. Each experiment was performed in triplicates.

Results

Figure 4:
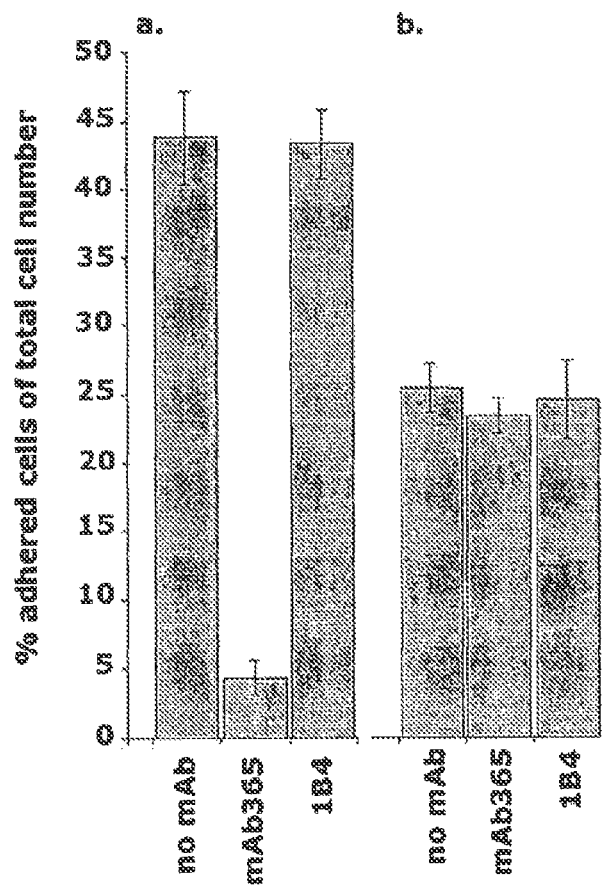

In FIG. 4a is shown that the antibody 365 inhibits binding of alpha10beta1-expressing C2C12 cells to collagen II in the presence of 1 mM $Mg^{2+}$ and 1 mM $Ca^{2+}$ Control (no Ab) and 1B4 (isotype control) showed no inhibition of binding.

In FIG. 4b is shown that binding of alpha11beta1-expressing C2C12 cells to type II collagen is not inhibited by the antibody 365. Control (no Ab) and 1B4 (isotype control) showed no inhibition of binding.

Example 5

Identification of Cells Expressing Alpha10 Integrin by FACS

Objective

The objective with this example is to use the antibody 365 to identify cells expressing human alpha10beta1 integrin.

Materials and Methods

Alpha10 and alpha11-transfected C2C12 and non-transfected C2C12 were trypsinized, washed with PBS and then incubated for 20 min with the antibody 365 1 µg/ml in PBS supplemented with 1% BSA. Labelled cells were washed twice with PBS/1% BSA and then incubated for 20 min with PE labelled goat-anti-mouse Ig (Pharmingen, BD Biosciences) at a concentration of 1 µg/ml in PBS/1% BSA. Cells were thereafter washed twice in PBS/1% BSA and were analysed on a FACSort® (Becton-Dickinson) by collecting 10,000 events with the Cell Quest® software program (Becton-Dickinson).

Results

Figure 5:
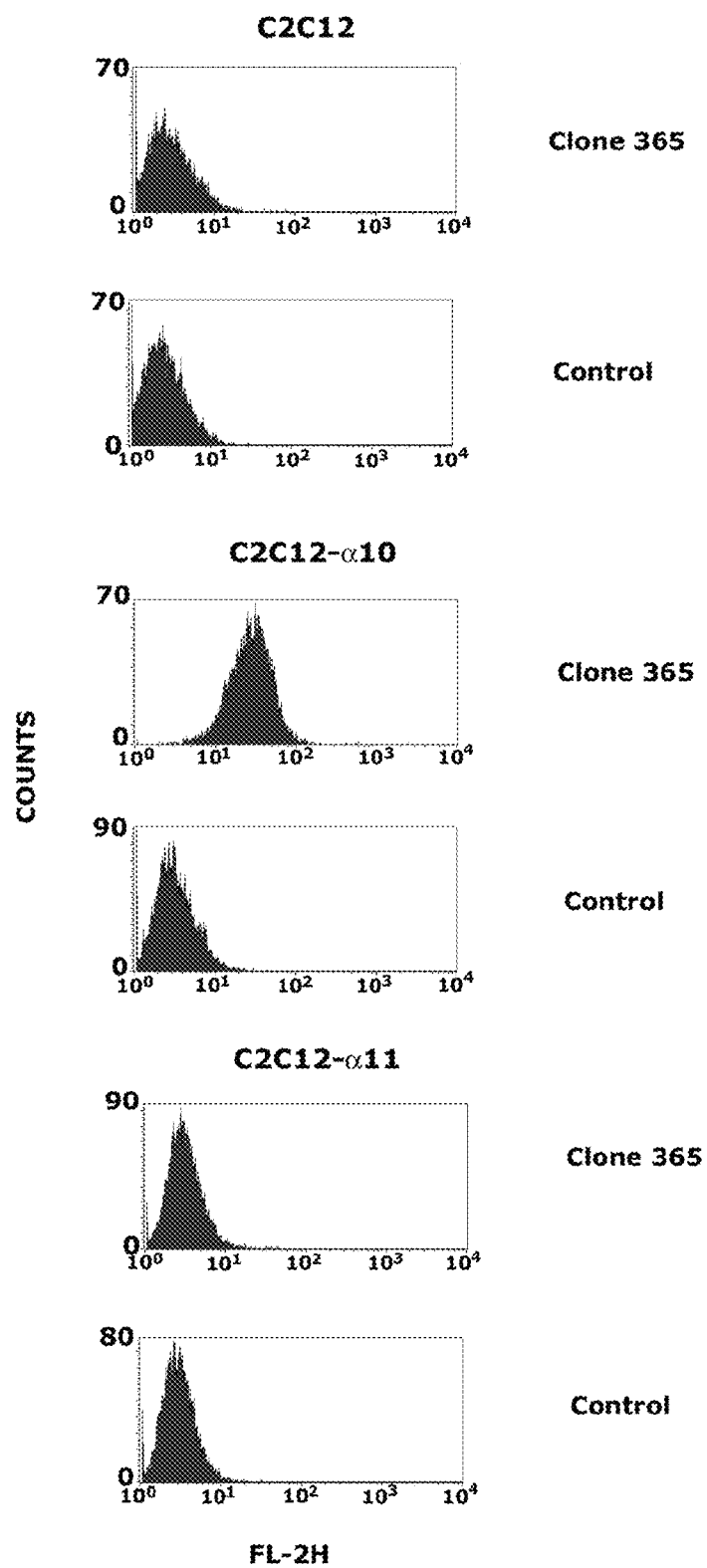

FIG. 5 shows the identification of cells expressing alpha10 using the antibody 365 in FACS analysis. In the FACS assay, the antibody 365 bound to C2C12 cells transfected with human alpha10 integrin-subunit, shown in the upper middle panel. This was seen as a displacement in the FACS histogram to the right. The antibody the antibody 365 did not bind to C2C12 cells transfected with human alpha11 integrin-subunit, as shown in the upper right panel, or untransfected C2C12 cells, as shown in the upper left panel. The lower panels represent secondary antibody, alone which did not bind to any of the cells tested.

Example 6

Selection of Cells Binding to the Antibody 365 by MACS®

Objective

The objective with this example is to positively select cells expressing alpha10beta1 by MACS® beads.

Materials and Methods

A mixed cell population containing alpha10beta1 expressing and non-expressing HEK 293-EBNA cells was subjected to positive selection for alpha10-expressing cells by using magnetic bead separation, MACS Cells were trypsinized, washed in PBS and then incubated with the antibody 365 at 1 µg/ml in PBS supplemented with 2 mM EDTA and 0.5% BSA (MACS buffer) for 15 min on ice. Incubated cells were thereafter washed twice with PBS and then resuspended in 80 µl MACS buffer and 20 µA goat-anti-mouse IgG Microbeads (Miltenyi Biotec Germany). After been incubated for 15 min on ice, the labelled cells were washed twice in MACS buffer and resuspended in 500 µl MACS buffer. The suspension were passed over a LS separation column containing a magnet (Miltenyi Biotec, Germany) and the column was washed with 3 ml MACS buffer three times to remove non-labelled cells.

The column was removed from the magnet and the labelled cells were eluted with MACS buffer and collected by centrifugation.

The three different cell fractions (cells before selection, flow through and positively selected cells) were incubated for 20 min with the antibody 365 1 µg/ml in PBS supplemented with 1% BSA. The cells were then washed twice with PBS/1% BSA and then incubated for 20 min with PE labelled goat-anti-mouse Ig (Pharmingen, BD Biosciences) at a concentration of 1 µg/ml in PBS/1% BSA. Cells were thereafter washed twice in PBS/1% BSA and then analysed on a FACSort® (Becton-Dickinson).

Results

Figure 6:
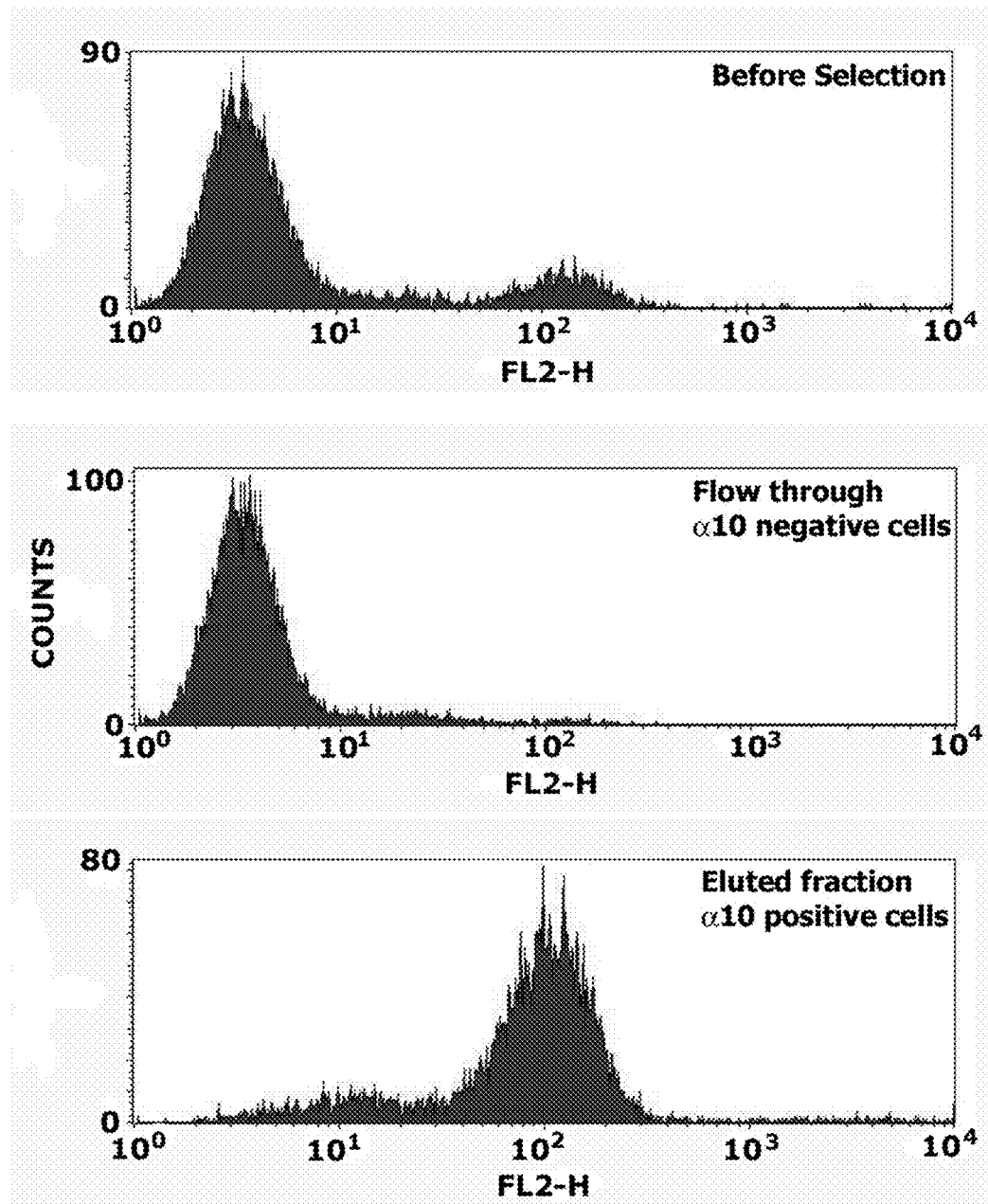

The effectiveness of the selection was determined by flow cytometry analysis, FACS, and is shown in FIG. 6. Cells before selection, flow through and eluted cells were stained with the antibody 365. The alpha10 positive populations are shifted to the right as displayed in the histograms. Out of 13 million of cells in the starting population, 1.48 million i.e. equivalent to 11% were positively selected. The positively selected cell fraction contained almost no alpha10beta1-negative cells. The flow-through fraction contained almost no alpha10-positive cells, confirming that the MACS-separation had efficiently removed alpha10-positive cells from the mixed cell population that had been used as starting material.

Example 7

Identification of a Population of hMNC Binding to the Antibody 365

Objective

The objective of this example is to identify a sub-population of human mononuclear cells using the antibody 365.

Materials and Methods

Human mononuclear cells (hMNC) were isolated from the bone marrow of the iliac crest of normal adults. About 20 to 30 ml of marrow aspirate was collected into a syringe containing 6000 units of heparin to prevent clotting. The marrow sample was diluted 1:1 with Iscove's modified Dulbecco's medium (IMDM)+5% FCS. The bone marrow suspension was the filtered through a 50 µm pore size mesh and 15 ml of Lymphoprep (Roche) added into 50 ml tubes. Bone marrow cells (25 ml) were carefully layered on the top of the Lymphoprep layer, avoiding mixing. The cells were then centrifuged for 30 min at room temperature at 400×g. The cells from the interface were then transferred into a 50 ml tube containing 25 ml of IMDM+5% FCS before centrifugation at 500×g for 15 min at 4° C. The supernatant was removed and 5.0 ml of buffer added (sterile PBS without $Ca^{2+}$ and $Mg^{2+}$ supplemented with 2 mM EDTA containing 5% FCS).

Identification of a Population of hMNCs by Flow Cytometry

Purified mononuclear cells from above were divided in two tubes and incubated for 20 min on ice with or without the antibody 365 (1 µg/ml) in PBS containing 1% foetal calf serum (FCS).

Labelled cells were washed once with PBS/1% FCS and then incubated for 20 min on ice with PE labelled goat-anti-mouse IgG (1 µg/ml Pharmingen BD Biosciences) this was followed by another wash with PBS/1% FCS. The cells were then incubated 20 min on ice with FITC labelled mouse-anti-human CD45 (1.2 µg/ml, BD Biosciences) for the identification of lymphocytes in the mononuclear preparation, and followed by a wash with PBS/1% FCS Labelled cells were analysed on a FACSCalibur® (Becton-Dickinson) by collecting a total of 1,000,000 events with the Cell Quest® software program (Becton-Dickinson).

Results

Figure 7:
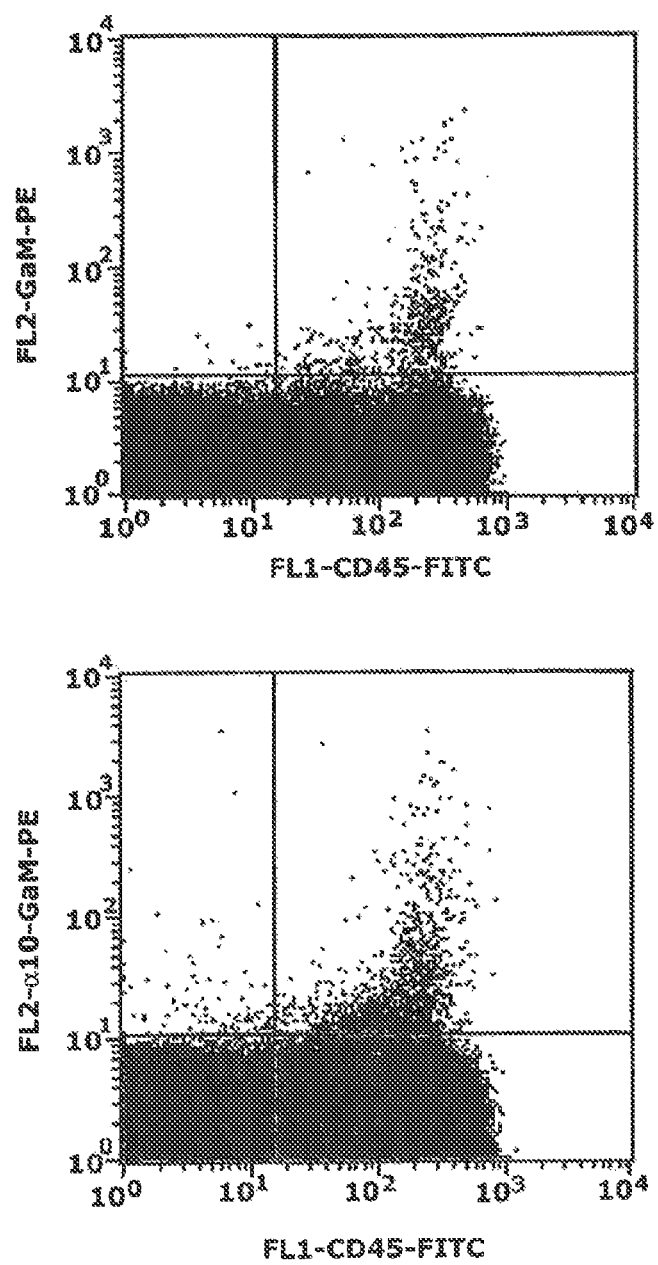

FIG. 7 shows identification of a population of integrin alpha10-expressing hMNCs using the antibody 365 in MACS analysis (lower panel). The upper panel shows MACS analysis in the absence of the antibody 365.

Example 8

Immunohistochemistry

Objective

The objective with this example is to show the binding in situ of the antibody 365 to human articular cartilage.

Materials and Methods

Tissue sections were warmed for 30 min at room temperature before the tissue was surrounded with PAP pen (Histolab) and fixed in acetone (Merck) for 10 min at −20° C. The tissue was then washed in PBS (Gibco/Invitrogen) at room temperature for 15 min, with one change of PBS, followed by digestion in 2 mg/ml hyaluronidase (Sigma EC 3.2.1.35) at 37° C. for 30 min. The digested tissue was washed twice in PBS under a 15 min incubation before blocking for 30 min at room temperature with 2% donkey serum (Jackson ImmunoResearch Laboratories, Inc.) in PBS. Primary antibody the antibody 365 was diluted 1:400 in 2% donkey serum in PBS and samples incubated for 75 min at room temperature. Samples were washed twice in PBS at room temperature during a 15 min incubation before addition of secondary antibody donkey-anti-mouse Cy3 (Jackson ImmunoResearch Laboratories, Inc.) for 60 min at room temperature. Samples were washed twice in PBS at room temperature during a 15 min incubation and slides were mounted with Vectashield Mounting Medium (Vector Laboratories). Tissue sections were viewed using a microscope equipped with a Cy3 filter.

Results

Figure 8:
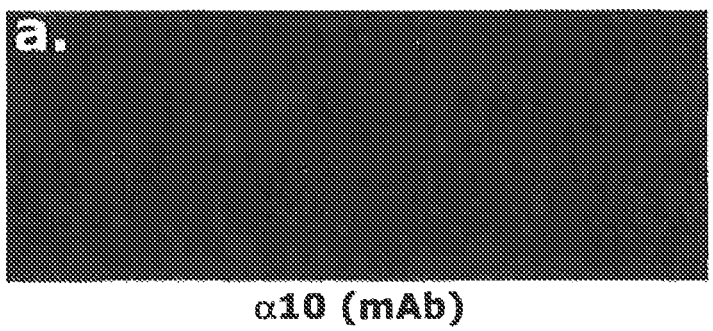
Figure 8:
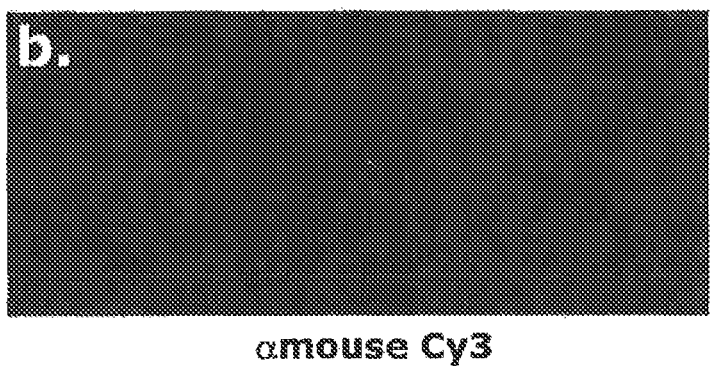

FIG. 8 shows immunolocalisation of integrin alpha10beta in human articular cartilage using the antibody 365 (upper panel). The secondary antibody only did not bind to the chondrocytes (lower panel).

Example 9

Use of mAb365 for Identification of a Population of Alpha10$^+$-Chondrocytes

Objective

The objective with this example is to identify a population of alpha10$^+$-chondrocytes.

Materials and Methods

Human chondrocytes were isolated from human normal cartilage by collagenase digestion (see protocol below).

Extraction of Human Chondrocytes

Extraction of human chondrocytes from human articular cartilage is performed in the following manner. The protocol is described by Brittberg et al in (1994) N. Engl. J. Med 331:889-895.

1. Upon receiving the human cartilage, wash 3× in PBS (−/−)+1:100 Penicillin/Streptomycin (PEST)+1:250 fungizone.
2. Place cartilage that is not to be dissected into culture media (DMEM at 37° C. in a 15 cm dish.
3. Dice the cartilage into 1-2 mm³ pieces.
4. Weigh out pronase (7001 U/ml=10 mg/ml), dissolve in medium (+1:100 PEST+1:250 fungizone) without serum, sterile filter and prewarm solution to 37° C. before using.
5. Incubate in pronase for no more than 30 mins at 37° C. with very gentle rolling.
6. Allow pieces to settle, remove the supernatant and discard.
7. Wash pieces three times in PBS−/− (+1:100 PEST+1:250 fungizone) to remove all pronase.
8. Weigh out collagenase (3501 U/ml) and dissolve in media without serum (+1:100 PEST+1:250 fungizone), sterile filter, and prewarm (37° C.) solution.
9. Digest the cartilage at 37° C. overnight with rolling.
10. Allow any remaining pieces to settle and then pipette supernatant through a 70 µm cell strainer and centrifuge at 1500 rpm for 10 mins.
11. Check the supernatant for cells after spinning and respin if necessary. If there are many pieces left, redigest in new collagenase (as above) at 37° C. with rolling.
12. To remove all collagenase, wash the cells three times in PBS (−/−)+PEST (1:100)+fungizone (1:250)+10% serum) (resuspend cells in PBS, then spin at 1500 for 10 minutes).
13. Resuspend in medium containing 10% serum and count—use Trypan blue exclusion.
14. Spin down and plate out at the required density or prepare for freezing.

Plating of Cells

The isolated cells were plated out using the following method:
1. Resuspend cells after counting in serum-free medium and plate out for 2-3 hrs.
2. Remove medium from cells and add medium containing 10% serum
3. Plating density:—T75 high density 8–10×10$^6$ cells/12 ml: low density 5-6×10$^6$ cells/12 ml.
4. Change medium every 2-3 days, depending on density of cells.

Cells were cultured in DMEM/F12 medium supplemented with 10% FCS, PEST and ascorbic acid 50 µg/ml. Cells were detached by day 1, or after 1, 2 and 6 weeks with trypsin/EDTA, and washed in PBS containing 1% BSA by centrifugation at 1200 rpm for 5 minutes.

FACS-Analysis of Cultured Cells

Cells were stained with mAb365 (1 µg/ml), or isotype control IgG. At the end of the incubation cells were washed again as described above, and the bound antibodies were detected by incubating cells with PE conjugated goat-anti mouse antibody (Pharmingen) for 20 minutes followed by another wash as above.

Cells were resuspended and analyzed by flow cytometry with FACSort (Becton Dickinson FACS system).

Results

Figure 9:
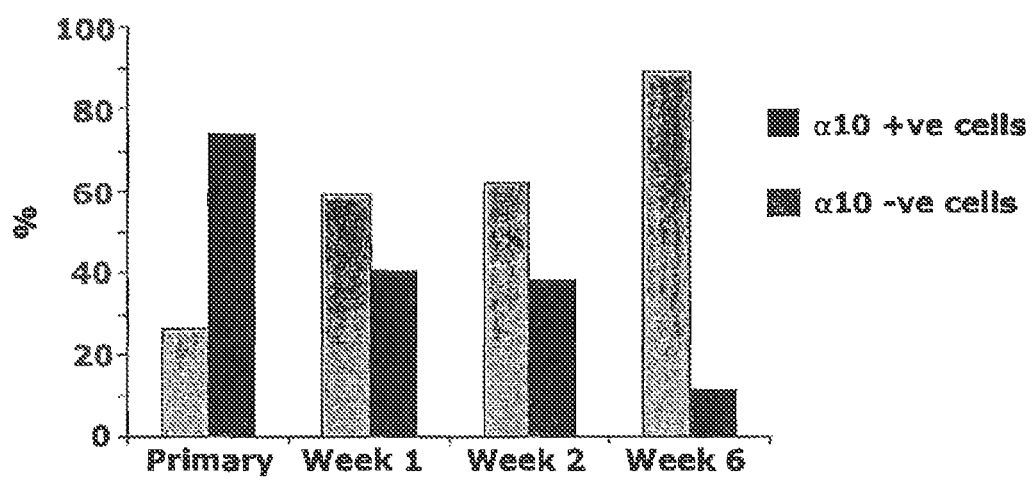

The results in FIG. 9 show a summary of the FACS data collected after analysis and indicate the percentage alpha10 positive cells identified by the mAb365 antibody in FACS analysis.

FACS analysis of cells was performed on cells that were detached on day 1, or after 1, 2 and 6 weeks. Cells were detected by incubating with PE conjugated goat-anti mouse antibody. Under the period of culture, the percentage alpha10 positive cells decreased from approx 70% at day 1 to 10% after 6 weeks in culture.

Example 10

Isolation of Alpha10-Positive Chondrocytes Using Magnetic Cell Sorting with mAb365

Objective

The objective of this example is to show that mAb365 can be used for solid phase cell sorting, for separation of alpha10-positive cells.

Materials and Methods

The human chondrocyte-fraction isolated in Example 9 was further fractionated into alpha10 positive and alpha10 negative cells by using magnetic cell sorting.

The human chondrocytes were labelled with 10 µg/ml mAb365 (anti-1-domain of alpha10 integrin receptor) for 20 minutes at 4° C., washed and labelled with goat anti-mouse IgG micro beads (Miltenyi Biotec, Germany) for 20 minutes in 4° C.

Alpha10 positive cells were isolated by positive selection with an LS midiMACS column (Miltenyi Biotec, Germany). This procedure is performed according to the manufacturers' instructions.

Remaining positive cells in the alpha10 negative fraction, from after the positive selection were depleted with an LD depletion column (Miltenyi Biotec, Germany).

1.6×10$^5$ cells of the positive and negative fraction were used for mRNA isolation. These cells were then used for a cDNA synthesis.

The cDNA was used for Quantitative PCR, which was performed on a Light Cycler (Roche) using FastStart DNA Master SYBR Green I using the following conditions: Denaturation for 10 min at 95° C., followed by 40 cycles with an annealing temperature of 65° C. with specific primers for each transcript (GAPDH, collagen I and collagen II). All PCR data were normalised against GAPDH.

Collagen Primers used:

```
Human Collagen I
                                            (SEQ ID NO: 1)
    COL I forward 3'-5' gCTTCCCTggTCTTCCTg (SEQ ID NO: 2)
    COL I reverse 3'-5' TCTCACCACggTCACCCT Human Collagen II
                                            (SEQ ID NO: 3)
    COL II forward 3'-5' CAggggTgAACgAggTTT (SEQ ID NO: 4)
    COL II reverse 3'-5' gAggTCCAACTTCTCCCTTCT
```

Measurement of Collagen Type II Production

For measurements of collagen content, either the total amount of collagen can be determined using the hydroxyproline assay (Woessner J. F 1976 In: The Methodology of Connective Tissue Research. Ed: Hall D pp 227-233) or collagen synthesis can be measured by radiolabelling with $^3$H Proline (Scutt et al (1992) Anal. Biochem 203:290-294).

As an example, measurement of hydroxyproline content is performed in the following manner: Samples containing collagen (typically collagen type II) are hydrolysed in 6.0 M HCl for 16 hours at 110° C. to liberate hydroxyproline.

After neutralization each sample is diluted at least 15 times to prevent the salt concentration from influencing the assay.

The samples are then dried under vacuum.

Method:
a. Samples (1-5 µg of hydroxyproline) are made up to 2.0 ml with assay buffer.
b. Add 1.0 ml of Chloramine-T reagent and stand for 20 minutes at room temperature.
c. Add 1.0 ml of freshly prepared dimethylaminobenzaldehyde reagent and mix thoroughly.
d. Incubate the tubes at 60° C. for 15 minutes and cool in tap water for 5 minutes.
e. Measure the absorbance at 550 nm within 45 minutes.

Note: The hydrolysate may be passed over short columns of Dowex-50-x-8 (H+ form, 200-400 mesh) to remove coloured material and impurities if necessary.

Reagents:
1. Stock buffer contains 50 g of citric acid (H$_2$O), 12 ml of glacial acetic acid, 120 g of sodium acetate, 3H$_2$O and 34 g of NaOH in 1.0 liter of solution. A few drops of toluene are added as preservative.
2. Assay buffer: The stock buffer solution is diluted tenfold with H$_2$O.
3. Chloramine-T reagent. 1.41 g of chloramine-T is dissolved in 20.7 ml of H$_2$O and mixed with 26 ml of n-propanol and 53.3 ml of stock buffer. (This reagent is stable at 4° C. for 2 weeks)
4. Dimethylaminobenzaldehyde reagent. 15 g of p-dimethylaminobenzaldehyde is suspended in 60 ml of n-propanol and 26 ml of perchloric acid (60%) is added slowly (N.B. Use a fume hood with protective goggles.) This reagent must be freshly prepared.

Results

Figure 10:
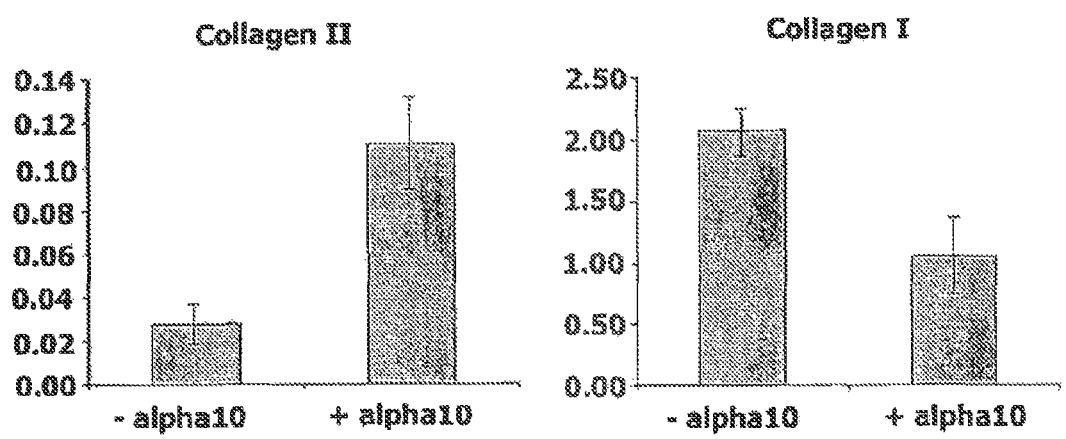

The results in FIG. 10 demonstrate the levels of collagen type II and collagen type I RNA in human chondrocytes separated by magnetic cell separation using mAb365 upon the basis of expression of the integrin alpha10beta1. The results show that:

i) The expression of collagen type II is greater than the expression of collagen type I in those cells that express the integrin alpha10beta1 i.e. are alpha10 positive.

ii) The expression of collagen type I is greater than the expression of collagen type II in those cells that do not express the integrin alpha10beta1 i.e. are alpha10 negative.

Discussion

This result indicates that alpha10-expressing cells produce mRNA coding for an extracellular matrix component, namely collagen type II, that is conducive to a cartilage-like matrix.

Conversely, cells lacking alpha10 produce more collagen type I mRNA, an extracellular matrix component associated with a more 'fibrocartilage-like' matrix.

Example 11

Identification of Murine Alpha10 by mAb365

Objective

The objective of this example is to test whether it identifies murine alpha10 expressed on chondrocytes.

Materials and Methods

Chondrocytes were isolated from rib cartilage from newborn wild-type or alpha10 knockout mutant mice using the following protocol described by Bengtsson et al. (Matrix Biology 2001 20(8):565-76)).

1. Dissect out the entire ribcage from the mouse.
2. Place the tissue in DMEM-PS (DMEM+1:50 PEST) in a Petri dish on ice.
3. Move the ribs (from ~3 mice/dish) to a small Petri dish with 3 ml DMEM-PS containing 2 mg/ml collagenase+2% FCS.
4. Incubate at 37° C. for 30 minutes, one dish at a time.
5. Remove the perichondrium from ribs and move the ribs to a new small Petri dish with DMEM-PS+2 mg/ml collagenase+2% FCS.
6. Incubate at 37° C. until the cells are resuspended.
7. Put the cell suspension through a 70 µm cell strainer into a 50 ml Falcon.
8. Inactivate collagenase with DMEM-PS+20% FCS.
9. Spin 2000 rpm for 10 minutes.
10. Wash again with 10 ml DMEM-PS+20% FCS; count cells while spinning
11. Freeze in cell culture freezing medium at about $1 \times 10^6$ cells/tube. Store at −80° C.

Chondrocytes were grown overnight in culture medium DMEM/F12 supplemented with 10% FCS, PEST and ascorbic acid 50 µg/ml before FACS analysis.

Cells were detached with trypsin/EDTA, and washed in PBS containing 1% BSA by centrifugation at 1200 rpm for 5 minutes.

Cells were incubated with mAb365, isotype control IgG at a concentration of 1 µg/ml, or FITC conjugated anti-CD29, an antibody that recognises the mouse beta 1 integrin.

At the end of the incubation cells were washed again as described above, and further incubated with isotype control or mAb365 and counterstained with PE conjugated goat-anti mouse antibody (Pharmingen) for 20 minutes followed by a subsequent wash.

Cells were resuspended and analyzed by flow cytometry with FACSort (Becton Dickinson FACS system)

Results and Discussion

Figure 11:
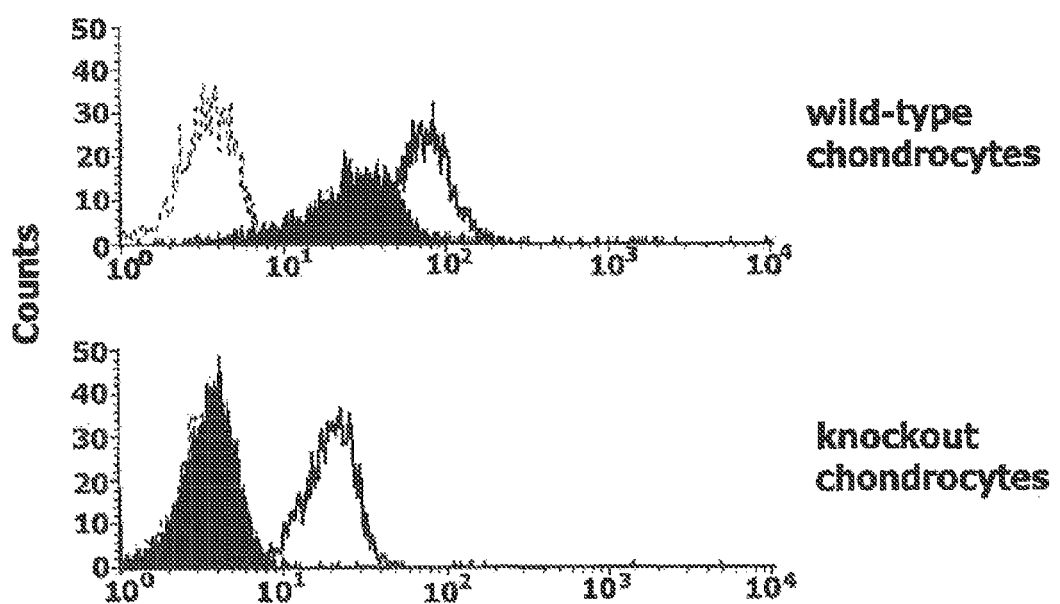

FIG. 11 shows the identification of integrin alpha10-expressing mouse chondrocytes using the antibody mAb365 in FACS analysis (upper figure panel).

The lower panel shows a control FACS analysis performed on mouse chondrocytes isolated from a integrin alpha10 knockout mouse (described in WO 03/101497 as well as in Bengtsson et al. Matrix Biology 2001 20(8):565-76).

The results show that mAb365 binds to murine alpha10 as well.

Example 12

Presence of Alpha10 on Human Mesenchymal Stem Cells

Objective

The objective with this example is to show the presence of alpha10 on human mesenchymal stem cells using mAb365.

Materials and Methods

Human mesenchymal stem cells may be obtained from Poietics or alternatively one may isolate them from bone marrow.

An alpha10 +ve population may then be isolated and further differentiated to see whether they are capable of becoming chondrocytes through different differentiating conditions as outlined below. Human mesenchymal stem cells obtained from adult normal bone marrow were purchased from Poietics/Cambrex (Cat no PT-2501). MAb365 was analysed in combination with other less specific markers for stem cells, such as CD105, CD166, CD44, CD14, CD34, and CD45 (Pieternella et al (2003) J. Haematol 88(08):845-852; Kirschstein, R and Skirboll, L. R (2001) Stem Cells: Scientific Progress and Future Directions. NIH Report. Department of Health and Human Services).

Purchased cells were thawed and cultured according to Poietics recommendation in defined medium (Cat no PT-3001) for 6 days. Cells were detached with trypsin/EDTA, and washed in PBS containing 1% BSA by centrifugation at 1200 rpm for 5 minutes.

Cells were typically stained with mAb365 (1-10 µg/ml), isotype control IgG or P4C10, an antibody recognising the beta1 chain of the integrin. At the end of the incubation cells were washed again as described above, and bound antibodies were detected by incubating cells with PE conjugated goat-anti mouse antibody (Pharmingen) for 20 minutes followed by another wash as above.

Cells were resuspended and analyzed by flow cytometry with FACSort (Becton Dickinson FACS system). The cells were also investigated for the presence for CD105, CD44, CD14 and CD45 (all antibodies from BD Biosciences/Pharmingen) to determine the mesenchymal stem cell phenotype.

Isolation of MSCs from Human Bone Marrow

As an alternative to using Poietics Mesenchymal Stem Cells, mesenchymal stem cells is isolated from human bone marrow by standard methods (Quirici et al (2002) Exp. Hematol 30(7):783-791). Bone marrow is taken from healthy allogeneic bone marrow transplantation donors, collected in heparinized tubes and layered onto Lymphoprep™ (density 1.077 g/ml, Nycomed, Norway) according to the manufactures' description.

The low-density mononuclear cells (LD-MNC) are then isolated from the human bone marrow cells by centrifugation. The LD-MNCs are washed twice in PBS and resuspended in MSCGM (mesenchymal stem cell growth medium) (Poetics, Cambrex Bio Science Walkersville, Inc.).

Mesenchymal Stem Cells is then purified from LD-MNCs by the following standard methods: by adhesion to plastic (Pittenger et al (1999) *Science* 184:143), CD45⁻/α-glycophorin A⁻ (Reyes et al (2001) *Blood*. 98(9):2615-25), CD105⁺ (Conrad et al. (2002). *Exp Hematol*. 30(8):887-95) and NGFR⁺ isolation (Quirici et al. (2002) *Exp Hematol*. 30(7): 783-91).

Isolation of Integrin Alpha10 Positive Cell Population

Integrin alpha10 positive cells is isolated by the following methods: Cells are labelled with a concentration ranging from 1-10 µg/ml mAb365 (α10 integrin receptor) for 20 minutes at 4° C., washed and labelled with goat anti-mouse IgG micro beads (Miltenyi Biotec, Germany) for 20 minutes in 4° C. The α10 positive cells are then isolated by positive selection with an LS midiMACS column (Miltenyi Biotec, Germany). This procedure is performed according to the manufacturers' instructions. Integrin alpha10 negative cells are retained as a control.

Differentiation of Integrin Alpha10 Positive (and Negative) Cells

After identification of an alpha10 positive cell population by any of the above methods (and corresponding negative population), it is desirable to be able to differentiate these cells to a chondrogenic phenotype (and be able to distinguish between the other known phenotypes by e.g. Yoo et al (1998) J. Bone J. Surgery Am 80:1745-1757).

The following methods, known to a man skilled in the art, (Tallheden et al J. Bone. J. Surgery 85A (Suppl2):93-100) may therefore be used to determine if the alpha10 positive cells identified using the mAb365 antibody may be differentiated to a chondrocytes phenotype. Other differentiation conditions will be used as a control. Examples of dedifferentiation protocols are given below:

Chondrogenic Differentiation

The cells are cultured as pellet mass in DMEM (Gibco-BRL, Paisley, UK), insulin transferrin sodium selenite (Sigma, Sweden), 0.1 µM dexamethasone (Sigma, Sweden), 80 µM ascorbic acid-2-phosphate (Sigma, Sweden), 1 mg/ml linoleic acid-bovine serum albumin (Sigma, Sweden), 100 U/ml Penicillin, 100 µg/ml Streptomycin (GibcoBRL, Paisley, UK) and 10 ng/ml TGF-ß3 (R&D Systems Europe Ltd., United Kingdom). To determine the chondrogenic differentiation the pellet cultures are tested for collagen type I and II, aggrecan and versican expression using Q-PCR.

Osteogenic Differentiation

To induce osteogenic differentiation the cells are cultured in DMEM-LG (GibcoBRL, Paisley, UK), 10% FCS (Sigma, St. Louis, Mo.), 50 µM ascorbic acid-2-phosphate (Sigma, Sweden), 0.10 µM dexamethasone (Sigma, Sweden), 100 U/ml Penicillin and 100 µg/ml Streptomycin (GibcoBRL, Paisley, UK). At day 11, 2 mM β-glycerophosphate (Sigma, Sweden) is added to the culture. The control cells are cultured without dexamethasone and β-glycerophosphate. The medium is changed every fourth day, during the 21 or 28 days of culture. The mineralization potential of the osteogenic differentiated cells are visualised by Von Kossa staining Adipogenic Differentiation To induce adipogenic differentiation the cells are cultured in DMEM-LG (GibcoBRL, Paisley, UK), 10% FCS (Sigma, St. Louis, Mo.), 1 µM dexamethasone (Sigma, Sweden), 60 µM indomethacin (Sigma, Sweden), 0.5 mM 3-isobutyl-methyl-xanthine (Sigma, Sweden), 5 µg/ml insulin (Sigma, Sweden), 100 U/ml Penicillin and 100 µg/ml Streptomycin (Gibco, Invitrogen). Every fourth day the cells are cultured during one day in DMEM-LG, 10% FCS (Sigma, St. Louis, Mo.), 100 U/ml Penicillin, 100 µg/ml Streptomycin (Gibco-BRL, Paisley, UK) and 5 µg/ml insulin (Sigma, Sweden). The negative control cells are cultured in DMEM-LG (Gibco-BRL, Paisley, UK) 10% FCS, 100 U/ml Penicillin and 100 µg/ml streptomycin (GibcoBRL, Paisley, UK). The cells are cultured for 14 days in differentiation media, the differentiated cells contain lipid vacuoles that can visualised with Oil Red 0 staining Results All the cells were positive for CD105, CD166 and CD44, and negative for CD14 and CD45 as determined by flow cytometry, indicating a mesenchymal stem cell phenotype.

Figure 12:
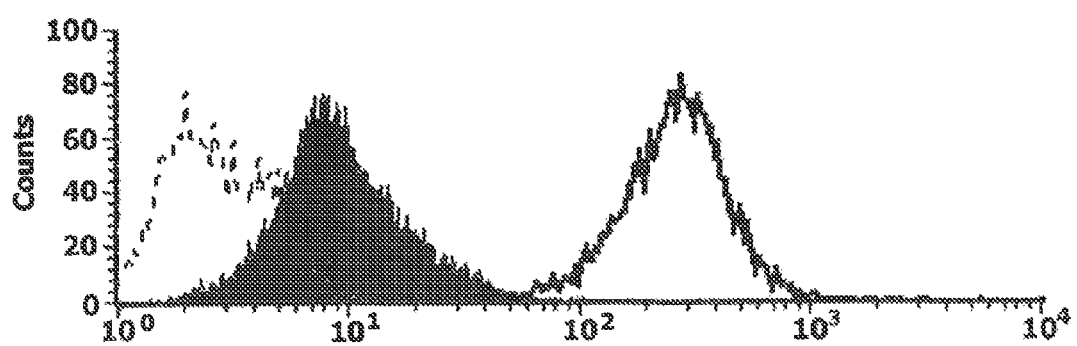

Upon investigating the expression of the integrin alpha10 on these stem cells by FACS analysis with the mAb365 antibody, approx 30% of the cells were shown to be alpha10 positive. The results are shown in FIG. 12.

These results indicate a subpopulation of human mesenchymal stem cells express the integrin alpha10.

Example 13

MAb 365 Stimulates Collagen Type II Production in Mouse Chondrocytes

Objective

The objective with the present example is to study signalling function of mAb365 via alpha10.

Materials and Methods

Mouse rib chondrocytes from C57 bl6 mouse were isolated using the protocol described previously in example 11 and cultured for two days in DMEM/F12 supplemented with 10% FCS, PEST and ascorbic acid 50 µg/ml. The cells were trypsinized and seeded into 15 ml tubes. Cells were spun down 150×g for 5 min and treated in the following manner: Control (no antibody), mAb365 (10 µg/ml) and control antibody (IgG2akappa) (10 µg/ml).

Cells with antibody treatments were placed in a cell incubator at 37° C., 5% $CO_2$, for 4 days to form pellet cultures. Cells were then treated again for 24 hrs with Control (no antibody), mAb365 (10 µg/ml) and control antibody (IgG2akappa) (10 µg/ml).

RNA was extracted from all pellets using an RNeasy kit (Qiagen). cDNA syntheses were made with Superscript™ II Rnase if Reverse Transcriptase (Invitrogen)

Quantitative PCR was performed in a Light Cycler (Roche) using FastStart DNA Master SYBR Green I with the following conditions: 10 min denaturation 95° C., followed by 40 cycles with an annealing temperature of 65° C. with specific primers for each transcript.

Results

Figure 13:
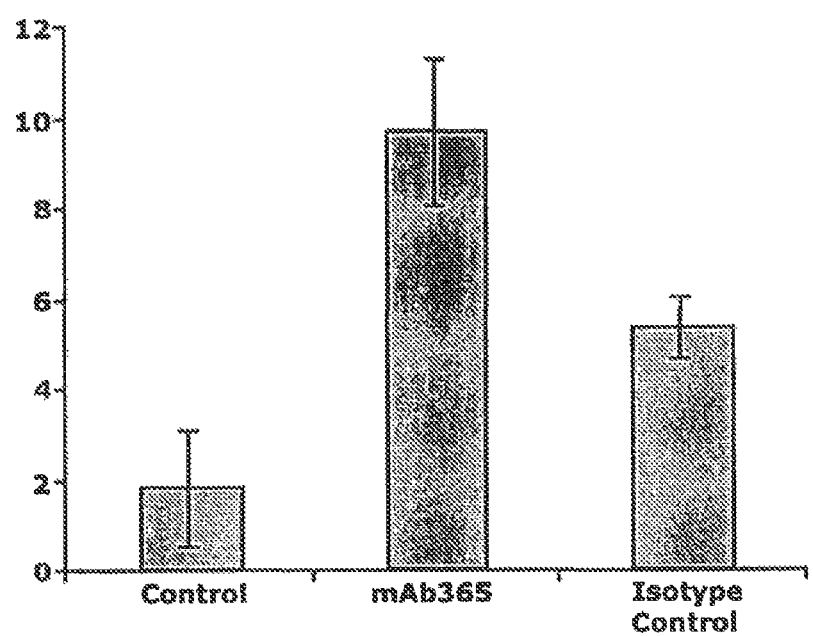
FIG. 13 shows that Collagen type II mRNA levels are stimulated in the presence of mAb365. Samples represent Control (no antibody), mAb365, and isotype control (IgG2akappa).

FIG. 13 demonstrates that mAb365 antibody stimulates the expression of collagen type II mRNA. The control medium or control antibody (IgG2akappa) did not affect collagen mRNA synthesis.

Example 14

MAb365 Detects the Integrin Alpha10Beta1 in Human Tissue Samples

Objective

The objective with this example is to show that the mAb365 can be used to detect the expression of the integrin alpha10beta1 in a tissue sample, for example, articular cartilage or atherosclerotic plaque.

Materials and Methods

In order to detect the presence of the integrin alpha10beta1 in tissue samples, for example, articular cartilage or atherosclerotic plaque, the following method is used:

1. Tissue is embedded in OCT, and 5 µm sections cut.
2. Sections are allowed to warm up to room temperature, surrounded by PAP pen, and are then fixed in acetone for 10 minutes at −20° C.
3. Slides are washed in PBS for 15 minutes, and then incubated with hyaluronidase (2 mg/ml in PBS; Sigma), at 37° C. for 30 minutes.
4. A second 15 minute wash in PBS is performed before incubating sections with 2% donkey serum (Jackson, West Grove, Pa.) diluted in PBS for 30 minutes to block. Sections are then incubated with mAb365 diluted 1:400 in 2% donkey serum in PBS, for 60 minutes at room temperature, and then washed in PBS for 15 minutes.
5. Incubation with the donkey-anti-mouseCy3 (Jackson) diluted in PBS is performed for 60 minutes at room temperature, followed by a final 15 minute wash in PBS. Slides can then be mounted with Vectashield, and observed under a fluorescence microscope.

Results

Figure 14:
FIG. 14 shows the results after staining normal human articular cartilage by immunohistochemistry using the mAb365 antibody. Integrin alpha10beta1 can be detected in the tissue, here represented by two different human specimens of 19 years and 53 years of age.

Analysis of normal human articular cartilage by immunohistochemistry using the mAb365 antibody shows that the integrin alpha10beta1 can be detected in the tissue, in FIG. 14 represented by two different human specimens of 19 years and 53 years of age.

Example 15

Labelling the mAb365 with Biotin for Detection of the Antibody In Vivo

Objective:
The objective with this example is to label the mAb365 with, for example, biotin. Labelled antibody is then used in a method for detecting the antibody in vitro and in vivo.

Materials and Methods

Biotinylation of mAb365:
mAb365 is reacted with 4 µl 5 mg/ml biotin NHS (Vector Labs), plus 10 µg of mAb365 antibody in a total volume of 50 µl with 100 mM Hepes (pH 8.5) for 2 hrs at room temp.

The sample is then dialysed in a volume of 500 ml for 30 mins with one change of 100 mM Hepes. Dialysis is performed in a slide-a-lyzer mini dialysis unit from Pierce (10,000 MWCO). The mAb365 is then collected and ready for use.

Injection of Biotinylated mAb365

One-week-old C57 mice are injected intraperitoneally (25 G needle) with 60 µl (=60 µg) mAb-BIOT (biotinylated mAb365) followed by a second injection after 6-8 hours with 50 µl (=50 µg) mAb-BIOT. Antibody titre is checked in serum by ELISA.

Back limbs are dissected out and embedded in OCT using standard methods such as Current Protocols in Molecular Biology. Vol2 Ch14. Ed: Ausubel et al (1991). Tissue is placed in a plastic mold with either the medial side down or plantar side down. The mold is then filled with OCT so that the tissue is completely covered, prior to placing on a copper plate on dry ice to freeze the tissue. Tissue blocks are stored at −20° C. Sections (5 µm) are cut on a cryostat, and slides are stored at −20° C.

Staining

Slides are allowed to come to room temperature for 30 minutes, and are then fixed in acetone for 10 mins at −20° C. After washing in PBS for 7+8 mins, sections are blocked in 2% donkey serum (diluted in PBS) for 30 minutes at room temperature. The sections were then incubated with SA-Cy3 (diluted 1:200 in 2% donkey serum) for 60 mins at room temperature. The slides are washed 7+8 mins in PBS, and coverslips mounted with Vectashield.

REFERENCES

Armulik, A. (2000) Studies on the transmembrane signalling of beta1 integrins. Doctoral Thesis (ISBN 91-544-4832-1). Uppsala University, Sweden.

Barry M A, Campos S K, Ghosh D, Adams K E, Mok H, Mercier G T, Parrott M B (2003). Biotinylated gene therapy vectors. Expert Opin Biol Ther. 2003 September; 3(6): 925-40. Rice University, USA, Boudreau, N. J. and Jones, P. L. (1999) Extracellular matrix and integrin signalling: the shape of things to come. Biochem. J. 339:481-488.

Boulianne G. L, Hozumi N, Shulman M. J. (1984) Production of functional chimaeric mouse/human antibody. Nature. 312(5995):643-6.

Brittberg, M, Lindahl, A, Nilsson, A, Ohlsson C, Isaksson, O, Peterson, L. (1994) Treatment of deep cartilage defects in the knee with autologous chondrocyte transplantation. N Engl J. Med. 331(14):889-95.

Brittberg M. (1999) Autologous chondrocyte transplantation. Clin Orthop October; (367 Suppl): S147-55.

Bruder, S. P, Jaiswal, N, Haynesworth, S. E. (1997) Growth kinetics, self-renewal, and the osteogenic potential of purified human mesenchymal stem cells during extensive subcultivation and following cryopreservation. J Cell Biochem. 64(2):278-94.

Camper, L, Hellman, U, Lundgren-Åkerlund E. (1999) Isolation, cloning, and sequence analysis of the integrin subunit alpha10, a beta1-associated collagen binding integrin expressed on chondrocytes. J Biol Chem 1998 273(32): 20383-9.

Caplan, A. and Bruder, S. P. (2001) Mesenchymal stem cells: building blocks for molecular medicine in the 21st century. Trends Mol. Med. 7(6):259-64.

David, G. S, Reisfeld, R. A. (1974) Protein iodination with solid state lactoperoxidase. Biochemistry. 13(5):1014-21.

Emsley, J, Knight, C. G, Farndale, R. W, Barnes, M. J, Liddington, R. C. (2000) Structural basis of collagen recognition by integrin alpha2beta1. Cell. 101(1):47-56.

Fong, C. Y., and Bongso, A. (1999) Comparison of human blastulation rates and total cell number in sequential culture media with and without co-culture. Hum. Reprod. 14, 774-781.

Fong, C. Y. Bongso, A, Ng, S. C, Anandakuma, r C, Trounson, A, Ratnam, S. (1997) Ongoing pregnancy after transfer of zona-free blastocysts: implications for embryo transfer in the human. Hum. Reprod. 12, 557-560.

Funaro, A, Horenstein, A. L, Malavasi, F. (1996) Monoclonal antibodies in clinical applications. J Biol Regul Homeost Agents. 10(4):72-82.

Gullberg, D. E and Lundgren-Åkerlund E. (2002) Collagen-binding I Domain Integrins—what do they do?. Prog. Histochem. Cytochem. 37(1):3-54.

Harlow, E and Lane, D (1988) Antibodies—A laboratory manual. Cold Spring Harbor Laboratory. New York.

Harlow, E and Lane, D (1999) Using Antibodies—A laboratory manual. Cold Spring Harbor Laboratory. New York.

Heino, J (2000) The collagen receptor integrins have distinct ligand recognition and signalling functions. Matrix Biology. 19:319-323.

Hering, T (1999) Regulation of chondrocyte gene expression. Frontiers in Bioscience. 4:743-761.

Jarrin, A and Andrieux, A (1999) Sequencing Antibodies. Meth. Mol. Biol. 96:21-28.

Jobanputra, P, Parry, D, Fry-Smith, A. and Burls, A (2001) Effectiveness of autologous chondrocyte transplantation for hyaline cartilage defects in knees: a rapid and systematic review. Health Technology Assessment 5(11):1-57.

Johnstone, B. and Yoo, J (2001) Mesenchymal cell transfer for articular cartilage repair. Expert Opin Biol Ther. 2001 1(6):915-21.

Jones, P. T, Dear, P. H, Foote, J, Neuberger, M. S, Winter, G (1986) Replacing the complementarity-determining regions in a human antibody with those from a mouse. Nature. 321(6069):522-5.

Jorgensen, C, Noel, D, Apparailly, F, Sany, J (2001) Stem cells for repair of cartilage and bone: the next challenge in osteoarthritis and rheumatoid arthritis. Ann Rheum Dis. 60(4):305-9.

Kirschstein, R and Skirboll, L. R (2001) Stem Cells: Scientific Progress and Future Directions. NIH Report. Department of Health and Human Services.

Luyten, F. P, Dell'Accio, F and De Bari, C (2001) Skeletal tissue engineering: opportunities and challenges. Best Prac & Res. Clin. Rheum. 15(5):759-770.

Morrison, S. L, Johnson, M. J, Herzenberg, L. A, Oi, V. T. (1984) Chimeric human antibody molecules: mouse antigen-binding domains with human constant region domains. Proc Natl Acad Sci USA. 81(21):6851-5.

Neuberger, M. S, Williams, G. T, Mitchell, E. B, Jouhal, S. S, Flanagan, J. G, Rabbitts T H. (1985) A hapten-specific chimaeric IgE antibody with human physiological effector function. Nature. 314(6008):268-70.

Nygren, H. (1982) Conjugation of horseradish peroxidase to Fab fragments with different homobifunctional and heterobifunctional cross-linking reagents. A comparative study. J Histochem Cytochem. 30(5):407-12.

Pain, D, Surolia, A. (1981) Preparation of protein A-peroxidase monoconjugate using a heterobifunctional reagent, and its use in enzyme immunoassays. J Immunol Methods. 40(2):219-30.

Parrott, M. Brandon, Kristen E. Adams, George T. Mercier, Hooyin Mok, Samuel K. Campos and Michael A. Barry (2003), Metabolically biotinylated adenovirus for cell targeting, ligand screening and vector purification, Molecular Therapy vol. 8, No. 4.

Pera, M A, Reubinoff, B and Trounson A (2000) Human embryonic stem cells. J. Cell Science. 113:5-10.

Pittenger, M. F, Mackay, A. M, Beck, S. C, Jaiswal, R. K, Douglas, R, Mosca, J. D, Moorman, M. A, Simonetti, D. W, Craig, S, Marshak, D. R. (1999) Multilineage potential of adult human mesenchymal stem cells. Science 284(5411): 143-7.

Plow E F, Haas T A, Zhang L, Loftus J, Smith J W. Ligand binding to integrins. J Biol. Chem. 2000 Jul. 21; 275(29): 21785-8.

Riechmann, L, Clark, M, Waldmann, H, Winter, G (1988) Reshaping human antibodies for therapy. Nature. 332(6162):323-7.

Scouten, W. H (1987) A survey of enzyme coupling techniques. Methods Enzymol. 135: 30-65.

Sites, D. P (1982) Basic and Clinical Immunology (Lange Medical Publications, Los Altos, Calif.)

Solter, D., and Knowles, B. (1975) Immunosurgery of mouse blastocyst. Proc. Natl. Acad. Sci. U.S.A. 72, 5099-5102

Talts J F., Brakebusch C., Fassler, R (1999) Integrin gene targeting. Methods Mol. Biol. 129, 153-187

Tulla, M, Pentikäinen, O. T, Viitasalo, T, Kapyla, J, Impola, U, Nykvist, P, Nissinen, L, Johnson, M. S, Heino, J (2001) Selective binding of collagen subtypes by integrin. all, a 21, and α10I domains. J Biol. Chem. 276(51):48206-48212.

Vaughan, T. J, Osbourn, J. K, Tempest, P. R. (1998) Human antibodies by design. Nat. Biotechnol. 16(6):535-9.

Velling, T, Kusche-Gullberg, M, Sejersen, T, Gullberg, D. (1999) cDNA cloning and chromosomal localization of human alpha(11) integrin. A collagen-binding, I domain-containing, beta(1)-associated integrin alpha-chain present in muscle tissues. J. Biol. Chem. 1999 274(36):25735-42.

Verhoeyen, M, Milstein, C, Winter G. (1988) Reshaping human antibodies: grafting an antilysozyme activity. 239 (4847):1534-6.

Zola. (1987) Monoclonal Antibodies: A manual of techniques. (CRC Press, Inc)

The invention claimed is:

1. A method for stimulating of the expression of collagen type II mRNA in a mammalian cell expressing integrin alpha10beta1, the method comprising the steps of:
   a) providing a mammalian cell expressing integrin alpha10beta1,
   b) contacting the cell with a monoclonal antibody or a fragment thereof under conditions wherein said monoclonal antibody or fragment thereof forms an antibody-antigen complex with an extracellular domain of integrin alpha10beta1 on said cell, wherein said antibody or fragment thereof binds specifically to an extracellular I-domain of an integrin alpha10 chain, and
   c) incubating said antibody-antigen complex, thereby stimulating the expression of collagen type II mRNA.

2. The method of claim 1, wherein said cell is a mesenchymal stem cell.

3. The method of claim 1, wherein said cell is an embryonic stem (ES) cell.

4. The method of claim 1, wherein said cell is a chondrocyte.

5. The method of claim 1, wherein said cell is a fibroblast.

6. The method of claim 1, wherein said monoclonal antibody or fragment thereof is the antibody produced by the hybridoma cell line deposited at the Deutsche Sammlung von Mikroorganismen and Zellkulturen GmbH under the accession number DSM ACC2583 or a fragment of the antibody produced by said hybridoma cell line.

* * * * *